(12) United States Patent
Greenberg et al.

(10) Patent No.: US 9,125,733 B2
(45) Date of Patent: Sep. 8, 2015

(54) BRANCHED VESSEL ENDOLUMINAL DEVICE

(75) Inventors: Roy K. Greenberg, Bratenahl, OH (US);
Karl J. West, Geneva, OH (US);
Davorin K. Skender, San Jose, CA (US); James C. Foster, Independence, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1555 days.

(21) Appl. No.: 12/174,451

(22) Filed: Jul. 16, 2008

(65) Prior Publication Data

US 2009/0043377 A1 Feb. 12, 2009

Related U.S. Application Data

(63) Continuation-in-part of application No. 11/403,605, filed on Apr. 13, 2006, now Pat. No. 7,407,509, which (Continued)

(51) Int. Cl.
*A61F 2/06* (2013.01)
*A61F 2/07* (2013.01)
*A61F 2/89* (2013.01)

(52) U.S. Cl.
CPC ... *A61F 2/07* (2013.01); *A61F 2/89* (2013.01); *A61F 2002/061* (2013.01); *A61F 2002/065* (2013.01); *A61F 2002/067* (2013.01); *A61F 2002/068* (2013.01); *A61F 2002/075* (2013.01);

(Continued)

(58) Field of Classification Search
CPC .......................................................... A61F 2/06
USPC .................. 623/1.35, 1.1, 1.16, 1.15; 606/198
See application file for complete search history.

(56) References Cited

U.S. PATENT DOCUMENTS

| 4,501,263 | A | * | 2/1985 | Harbuck .................... 128/898 |
| 4,592,754 | A | | 6/1986 | Gupte et al. |
| 4,762,130 | A | | 8/1988 | Fogarty et al. |

(Continued)

FOREIGN PATENT DOCUMENTS

| EP | 0 461 791 B1 | 6/1991 |
| EP | 0 646 365 B1 | 9/1994 |

(Continued)

OTHER PUBLICATIONS

Greenberg et al., "Beyond the Aortic Bifurcation: Branched Endovascular Grafts for Thoracoabdominal and Aortoiliac Aneurysms," 43 Journal of Vascular Surgery, No. 5, pp. 879-886 (May 2006).

(Continued)

*Primary Examiner* — Thomas J Sweet
*Assistant Examiner* — Matthew Schall
(74) *Attorney, Agent, or Firm* — Brinks Gilson & Lione

(57) ABSTRACT

An endoluminal prosthesis comprises a prosthetic trunk having a trunk lumen and a trunk wall, a first prosthetic branch having a first branch lumen and a branch wall, and a second prosthetic branch having a second branch lumen. The first branch lumen and the second branch lumen are both in fluid communication with the trunk lumen through the trunk wall and the second branch lumen is in fluid communication with the first branch lumen through the branch wall. Additional devices, systems, and methods are disclosed.

13 Claims, 41 Drawing Sheets

Related U.S. Application Data is a continuation-in-part of application No. 10/756,803, filed on Jan. 13, 2004, now Pat. No. 7,105,020.

(60) Provisional application No. 60/439,923, filed on Jan. 14, 2003, provisional application No. 60/478,107, filed on Jun. 11, 2003, provisional application No. 60/510,636, filed on Oct. 10, 2003, provisional application No. 60/671,410, filed on Apr. 13, 2005.

(52) U.S. Cl.
CPC . *A61F 2230/0013* (2013.01); *A61F 2230/0067* (2013.01); *A61F 2250/0063* (2013.01)

(56) References Cited

U.S. PATENT DOCUMENTS

| | | |
|---|---|---|
| 4,902,508 A | 2/1990 | Badylak et al. |
| 5,129,910 A | 7/1992 | Phan et al. |
| 5,197,976 A | 3/1993 | Herweck et al. |
| 5,413,601 A | 5/1995 | Keshelava |
| 5,522,880 A | 6/1996 | Barone et al. |
| 5,562,724 A | 10/1996 | Vorwerk et al. |
| 5,571,173 A | 11/1996 | Parodi |
| 5,578,071 A | 11/1996 | Parodi |
| 5,591,229 A | 1/1997 | Parodi |
| 5,617,878 A | 4/1997 | Taheri |
| 5,653,743 A | 8/1997 | Martin |
| 5,693,087 A | 12/1997 | Parodi |
| 5,733,337 A | 3/1998 | Carr, Jr. et al. |
| 5,824,040 A | 10/1998 | Cox et al. |
| 5,921,995 A | 7/1999 | Kleshinski |
| 5,984,955 A | 11/1999 | Wisselink |
| 5,993,481 A * | 11/1999 | Marcade et al. ............. 623/1.35 |
| 6,030,414 A | 2/2000 | Taheri |
| 6,039,754 A | 3/2000 | Caro |
| 6,059,824 A | 5/2000 | Taheri |
| 6,077,296 A | 6/2000 | Shokoohi et al. |
| 6,093,203 A | 7/2000 | Uflacker |
| 6,099,558 A | 8/2000 | White et al. |
| 6,102,940 A | 8/2000 | Robichon et al. |
| 6,136,022 A | 10/2000 | Nuñez et al. |
| 6,152,956 A | 11/2000 | Pierce |
| 6,187,033 B1 | 2/2001 | Schmitt et al. |
| RE37,107 E | 3/2001 | Wells-Roth |
| 6,206,931 B1 | 3/2001 | Cook et al. |
| 6,210,429 B1 | 4/2001 | Vardi et al. |
| 6,221,090 B1 | 4/2001 | Wilson |
| 6,221,098 B1 | 4/2001 | Wilson et al. |
| 6,264,682 B1 | 7/2001 | Wilson et al. |
| 6,283,991 B1 | 9/2001 | Cox et al. |
| 6,290,731 B1 | 9/2001 | Solovay et al. |
| 6,325,819 B1 | 12/2001 | Pavenik et al. |
| 6,325,826 B1 | 12/2001 | Vardi et al. |
| 6,334,869 B1 | 1/2002 | Leonhardt et al. |
| 6,344,056 B1 | 2/2002 | Dehdashtian |
| 6,358,284 B1 | 3/2002 | Fearnot et al. |
| 6,361,544 B1 | 3/2002 | Wilson et al. |
| 6,395,018 B1 | 5/2002 | Castaneda |
| 6,409,750 B1 | 6/2002 | Heyodoh et al. |
| 6,409,756 B1 | 6/2002 | Murphy |
| 6,409,757 B1 | 6/2002 | Trout, III et al. |
| 6,428,565 B1 | 8/2002 | Wisselink |
| 6,478,817 B2 | 11/2002 | Schmitt et al. |
| 6,482,227 B1 | 11/2002 | Solovay |
| 6,508,836 B2 | 1/2003 | Wilson et al. |
| 6,517,574 B1 | 2/2003 | Chuter |
| 6,520,988 B1 | 2/2003 | Colombo et al. |
| 6,524,335 B1 | 2/2003 | Hartley et al. |
| 6,554,856 B1 | 4/2003 | Doorly et al. |
| 6,579,309 B1 | 6/2003 | Loos et al. |
| 6,582,394 B1 | 6/2003 | Reiss et al. |
| 6,585,758 B1 | 7/2003 | Chouinard et al. |
| 6,599,302 B2 | 7/2003 | Houser et al. |
| 6,599,315 B2 | 7/2003 | Wilson |
| 6,641,606 B2 | 11/2003 | Ouriel et al. |
| 6,645,242 B1 | 11/2003 | Quinn |
| 6,652,567 B1 | 11/2003 | Deaton |
| 6,663,667 B2 | 12/2003 | Dehdashtian et al. |
| 6,669,720 B1 | 12/2003 | Pierce |
| 6,706,062 B2 | 3/2004 | Vardi et al. |
| 6,723,116 B2 | 4/2004 | Taheri |
| 6,733,522 B2 | 5/2004 | Schmitt et al. |
| 6,733,523 B2 | 5/2004 | Shaolian et al. |
| 6,767,358 B2 | 7/2004 | Leonhardt et al. |
| 6,773,457 B2 | 8/2004 | Ivancev et al. |
| 7,105,020 B2 | 9/2006 | Greenberg et al. |
| 7,232,459 B2 | 6/2007 | Greenberg et al. |
| 2001/0012962 A1 | 8/2001 | Schmitt et al. |
| 2001/0027338 A1 | 10/2001 | Greenberg |
| 2001/0037142 A1 | 11/2001 | Stelter et al. |
| 2002/0052648 A1 | 5/2002 | McGuckin, Jr. et al. |
| 2002/0058984 A1 | 5/2002 | Butaric et al. |
| 2002/0058986 A1 | 5/2002 | Landau et al. |
| 2002/0058987 A1 | 5/2002 | Butaric et al. |
| 2002/0058991 A1 | 5/2002 | Schmitt |
| 2002/0058993 A1 | 5/2002 | Landau et al. |
| 2002/0082684 A1 | 6/2002 | Mishaly |
| 2002/0099441 A1 | 7/2002 | Dehdashtian |
| 2002/0111674 A1 | 8/2002 | Chouinard et al. |
| 2002/0120327 A1 | 8/2002 | Cox et al. |
| 2002/0143383 A1 | 10/2002 | Parodi |
| 2002/0144696 A1 | 10/2002 | Sharkawy et al. |
| 2002/0151957 A1 | 10/2002 | Kerr |
| 2002/0156517 A1 | 10/2002 | Peroe |
| 2002/0156522 A1 | 10/2002 | Ivancev et al. |
| 2002/0173840 A1 | 11/2002 | Brucker et al. |
| 2002/0193872 A1 | 12/2002 | Trout, III et al. |
| 2002/0198585 A1 | 12/2002 | Wisselink |
| 2003/0009212 A1 | 1/2003 | Kerr |
| 2003/0033005 A1 | 2/2003 | Houer et al. |
| 2003/0074050 A1 | 4/2003 | Kerr |
| 2003/0093145 A1 | 5/2003 | Lawrence-Brown et al. |
| 2003/0120333 A1 | 6/2003 | Ouriel et al. |
| 2003/0130720 A1 | 7/2003 | De Palma et al. |
| 2003/0130724 A1 | 7/2003 | De Palma et al. |
| 2003/0195614 A1 | 10/2003 | Ryan et al. |
| 2003/0199967 A1 * | 10/2003 | Hartley et al. ............... 623/1.13 |
| 2003/0199973 A1 | 10/2003 | Chuter et al. |
| 2003/0204242 A1 | 10/2003 | Zarins et al. |
| 2003/0220682 A1 | 11/2003 | Kujawski |
| 2003/0225453 A1 | 12/2003 | Murch |
| 2004/0034406 A1 | 2/2004 | Thramann |
| 2004/0044396 A1 | 3/2004 | Clerc et al. |
| 2004/0059406 A1 | 3/2004 | Cully et al. |
| 2004/0073288 A1 | 4/2004 | Kerr |
| 2004/0093078 A1 | 5/2004 | Moll et al. |
| 2004/0106972 A1 | 6/2004 | Deaton |
| 2004/0133266 A1 | 7/2004 | Clerc et al. |
| 2004/0138737 A1 | 7/2004 | Davidson et al. |
| 2004/0167607 A1 | 8/2004 | Frantzen |
| 2004/0193245 A1 | 9/2004 | Deem et al. |
| 2005/0102021 A1 | 5/2005 | Osborne |
| 2005/0131517 A1 | 6/2005 | Hartley et al. |
| 2005/0131519 A1 | 6/2005 | Hartley |
| 2005/0131525 A1 | 6/2005 | Hartley |
| 2005/0273155 A1 | 12/2005 | Bahler et al. |
| 2006/0004433 A1 | 1/2006 | Greenberg et al. |
| 2006/0095118 A1 | 5/2006 | Hartley |
| 2006/0136046 A1 | 6/2006 | Hartley et al. |
| 2007/0142896 A1 | 6/2007 | Anderson et al. |

FOREIGN PATENT DOCUMENTS

| | | |
|---|---|---|
| EP | 0 903 118 A2 | 9/1994 |
| EP | 0 903 118 A3 | 9/1994 |
| JP | 04-231954 A | 8/1992 |
| JP | 07-008512 A | 1/1995 |
| WO | WO 95/09585 A1 | 4/1995 |
| WO | WO 95/16406 A1 | 6/1995 |

(56) References Cited

FOREIGN PATENT DOCUMENTS

| | | |
|---|---|---|
| WO | WO 95/21592 A1 | 8/1995 |
| WO | WO 98/22158 A2 | 5/1998 |
| WO | WO 98/22158 A3 | 5/1998 |
| WO | WO 98/53761 A1 | 12/1998 |
| WO | WO 99/13808 A1 | 3/1999 |
| WO | WO 99/48441 A1 | 9/1999 |
| WO | WO 00/32241 A1 | 6/2000 |
| WO | WO 02/067815 A1 | 9/2002 |
| WO | WO 03/065933 A1 | 8/2003 |
| WO | WO 03/082153 A2 | 10/2003 |
| WO | WO 03/082153 A3 | 10/2003 |
| WO | WO 2004/064686 A1 | 8/2004 |
| WO | WO 2004/093746 A1 | 11/2004 |
| WO | WO 2006/113501 A1 | 10/2006 |

OTHER PUBLICATIONS

Greenberg et al., "Endovascular Management of Juxtarenal Aneurysms with Fenestrated Endovascular Grafting," 39 Journal of Vascular Surgery, No. 2, pp. 279-287 (Feb. 2004).

Greenberg et aL, "Primary Endovascular Repair of Juxtarenal Aneurysms with Fenestrated Endovascular Grafting," 27 European Journal of Vascular Surgery, pp. 484-491 (2004).

Huynh et aL, "Remodeling of an Acellular Collagen Graft into a Physiologically Responsive Neovessel," 17 Nature Biotechnology, pp. 1083-1086 (Nov. 1999).

Communication pursuant to Article 96(2) EPC, dated Sep. 17, 2007, for related European Application No. 04 701 753.8-2310.

International Search Report and Written Opinion of the International Searching Authority for International Application No. PCT/US2009/004124.

* cited by examiner

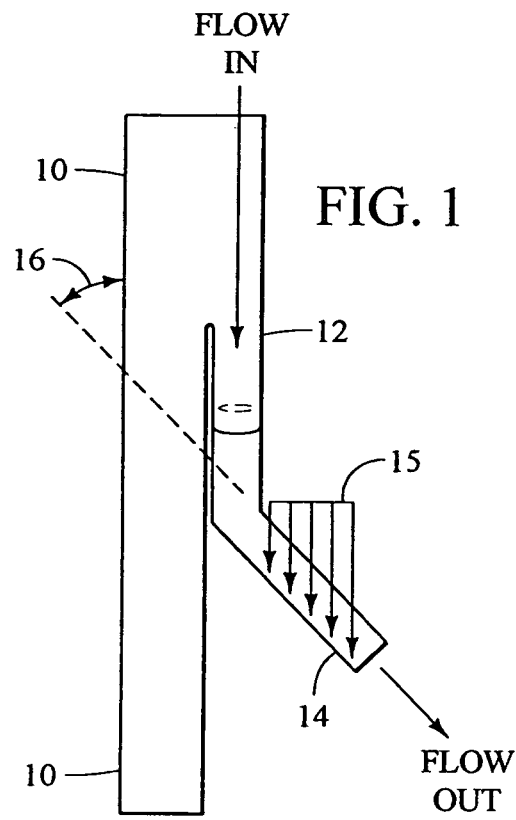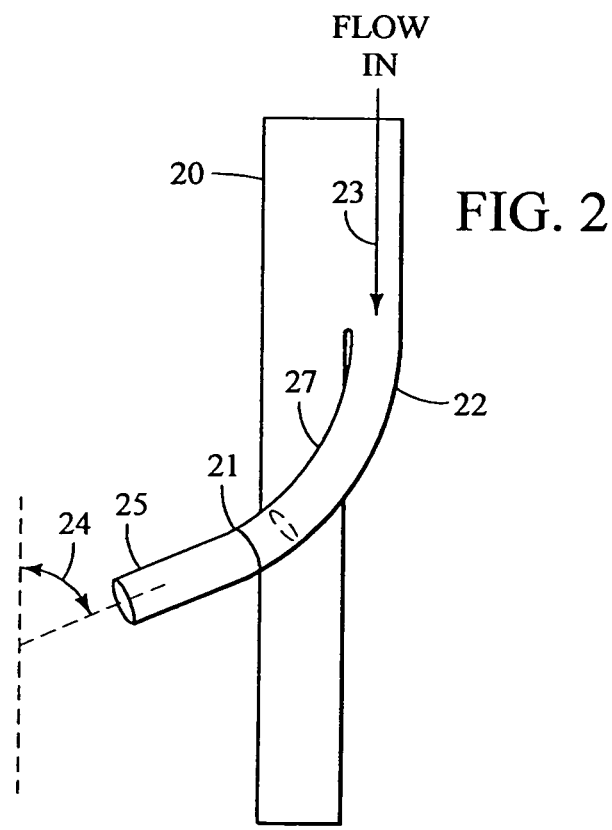

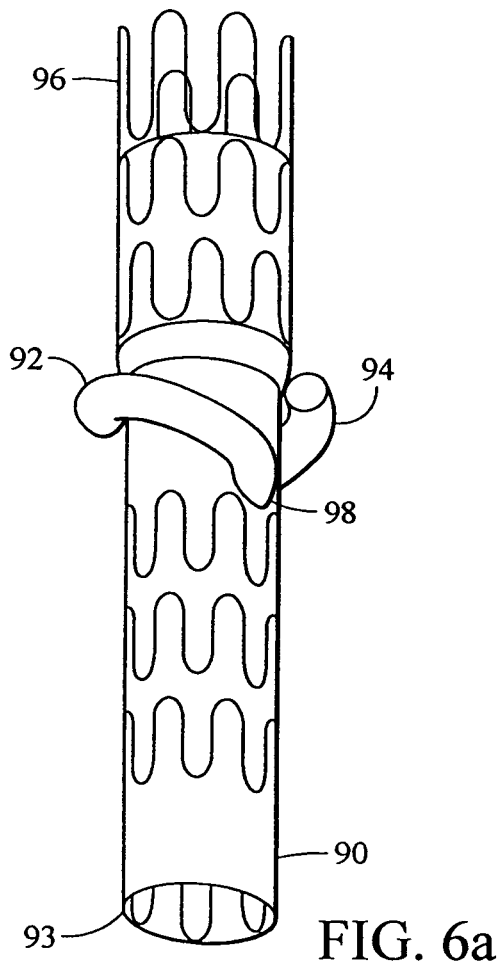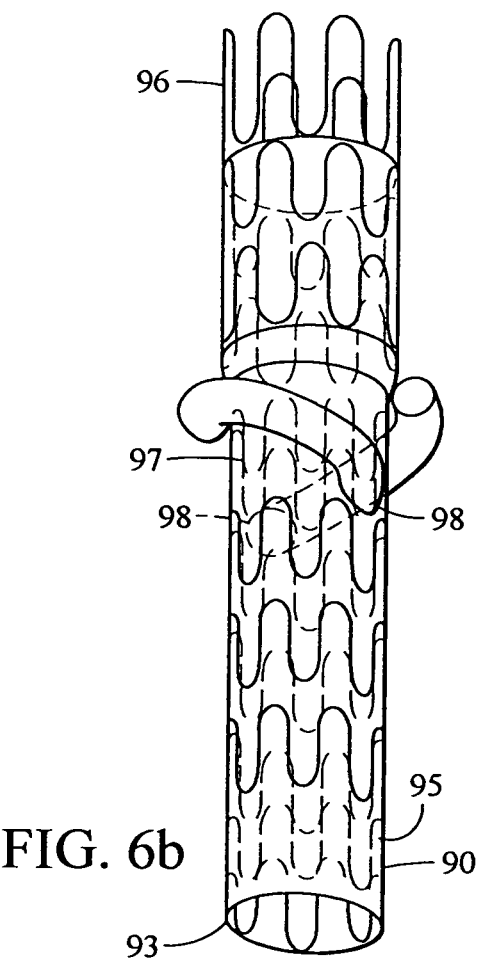
FIG. 6a
FIG. 6b

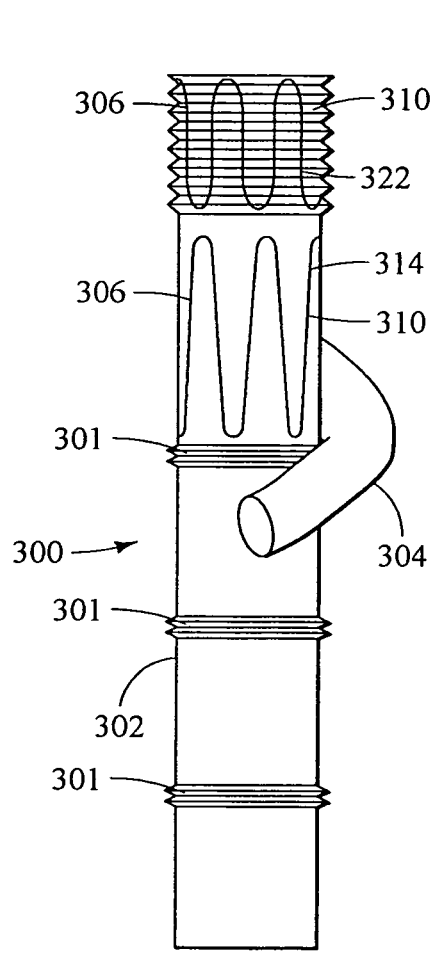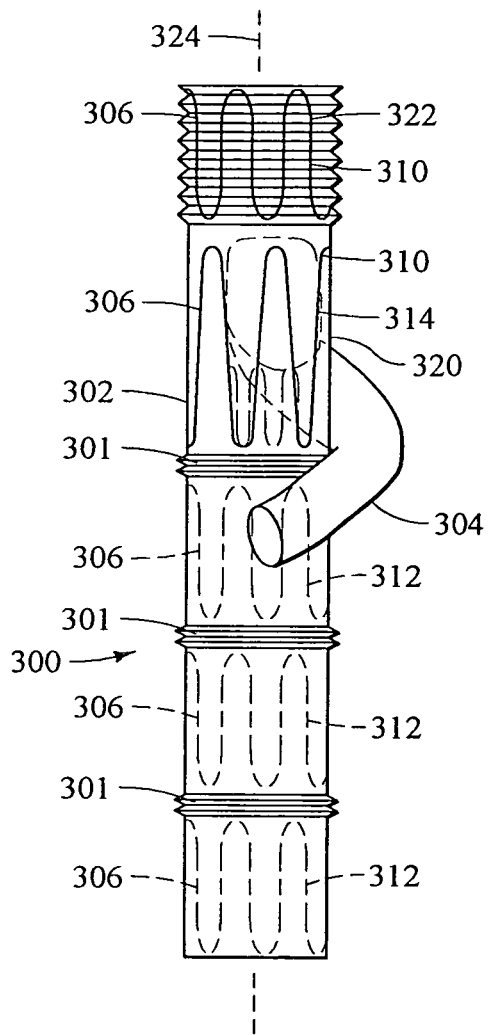
FIG. 13a
FIG. 13b
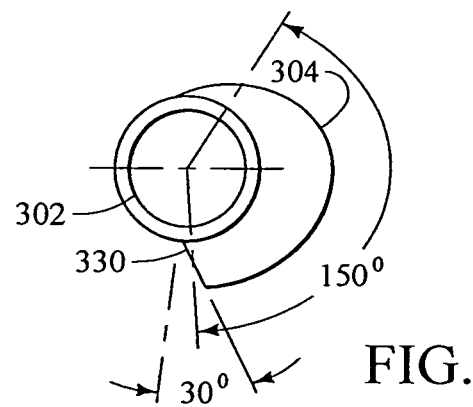
FIG. 13c

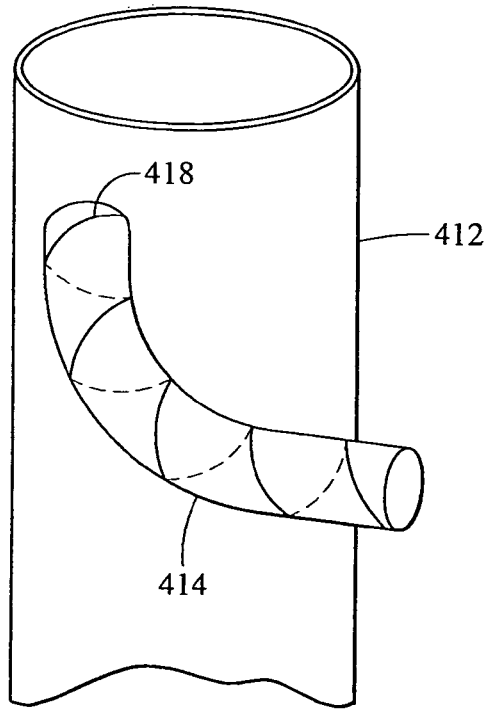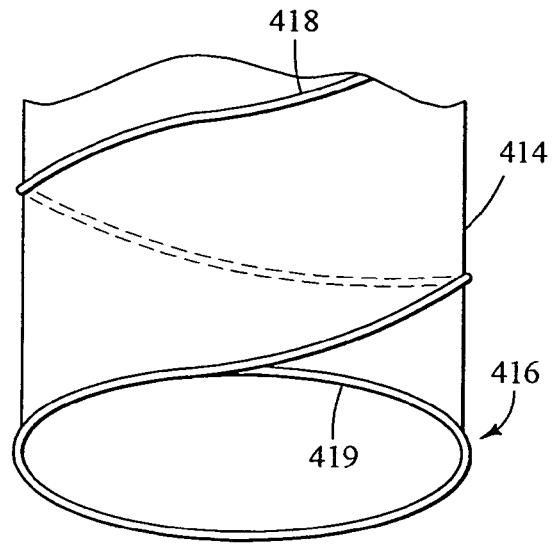
FIG. 18
FIG. 19
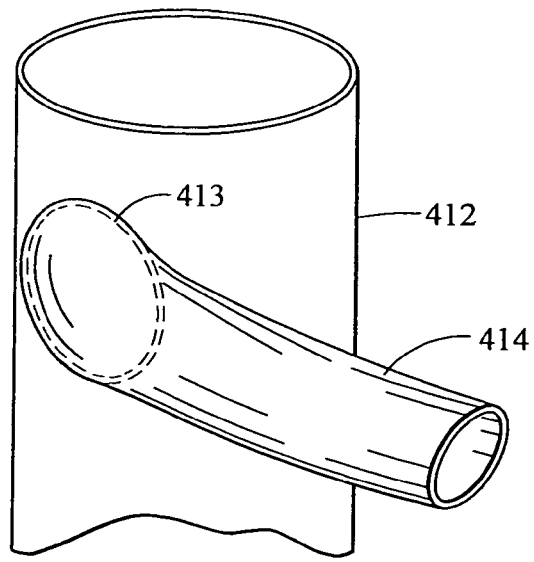
FIG. 20

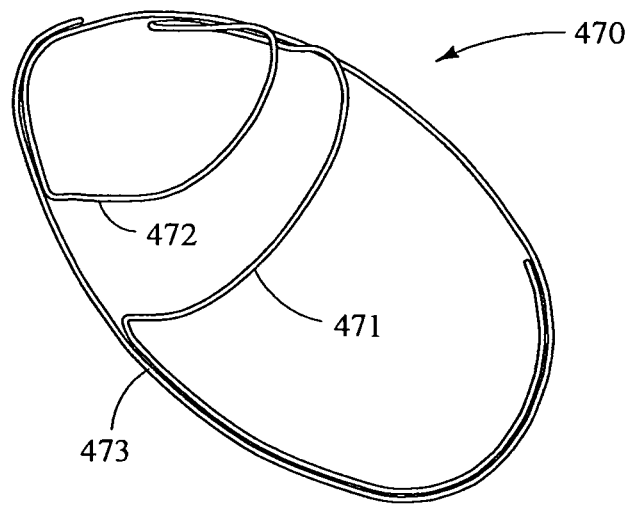
FIG. 23a
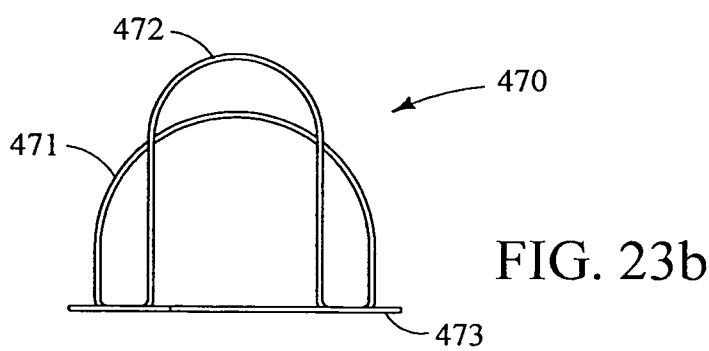
FIG. 23b
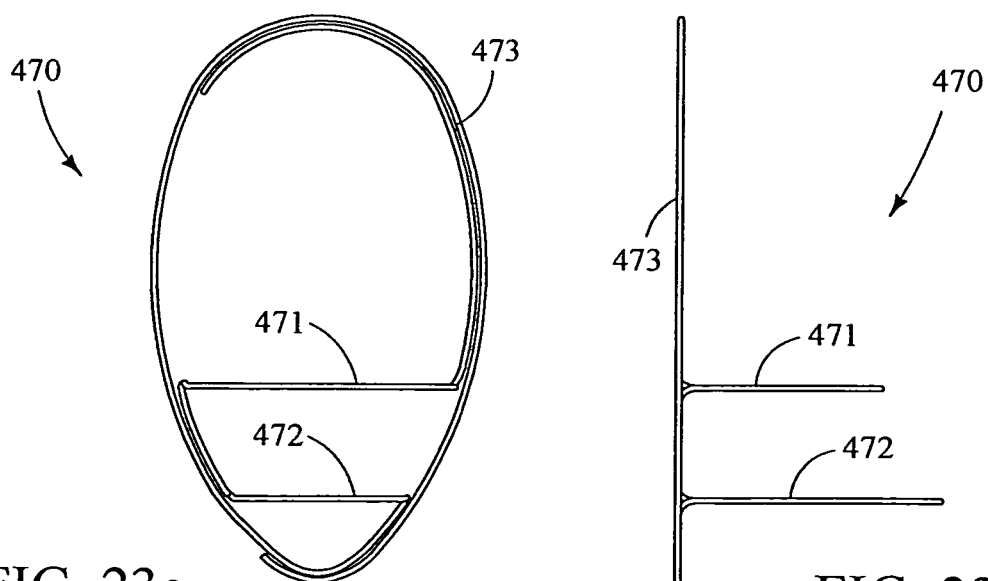
FIG. 23c
FIG. 23d

BRANCHED VESSEL ENDOLUMINAL DEVICE

RELATED APPLICATIONS

This application is a continuation-in-part of U.S. patent application Ser. No. 11/403,605, filed Apr. 13, 2006 (U.S. Patent Application Publication No. 2006/0247761), which is a continuation-in-part of U.S. patent application Ser. No. 10/756,803, filed Jan. 13, 2004 (U.S. Pat. No. 7,105,020), which claims the benefit of the filing date under 35 U.S.C. §119(e) of U.S. Provisional Patent Application Ser. No. 60/439,923, filed Jan. 14, 2003; U.S. Provisional Patent Application Ser. No. 60/478,107, filed Jun. 11, 2003; and U.S. Provisional Patent Application Ser. No. 60/510,636, filed Oct. 10, 2003, all of which are incorporated herein by reference.

This application also claims the benefit of the filing date under 35 U.S.C. §119(e) of U.S. Provisional Patent Application Ser. No. 60/671,410, filed Apr. 13, 2005, which is incorporated herein by reference.

TECHNICAL FIELD

This invention relates to prostheses for implantation within the human or animal body for the repair of damaged vessels, ducts or other physiological passageways.

BACKGROUND

Throughout this specification, when discussing the application of this invention to the aorta or other blood vessels, the term "distal" with respect to a prosthesis is intended to refer to a location that is, or a portion of the prosthesis that when implanted is, further downstream with respect to blood flow; the term "distally" means in the direction of blood flow or further downstream. The term "proximal" is intended to refer to a location that is, or a portion of the prosthesis that when implanted is, further upstream with respect to blood flow; the term "proximally" means in the direction opposite to the direction of blood flow or further upstream.

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture. One study found that in Western European and Australian men who are between 60 and 75 years of age, aortic aneurysms greater than 29 mm in diameter are found in 6.9% of the population, and those greater than 40 mm are present in 1.8% of the population.

One surgical intervention for weakened, aneurysmal or ruptured vessels involves the use of an endoluminal prosthesis to provide some or all of the functionality of the original, healthy vessel and/or preserve any remaining vascular integrity by replacing a length of the existing vessel wall that spans the site of vessel failure.

It is preferable that these prostheses seal off the failed portion of the vessel. For weakened or aneurysmal vessels, even a small leak in the prosthesis may lead to the pressurization of or flow in the treated vessel, which aggravates the condition the prosthesis was intended to treat. A prosthesis of this type can, for example, treat aneurysms of the abdominal aortic, iliac, or branch vessels such as the renal arteries.

An endoluminal prosthesis can be of a unitary construction, or be comprised of multiple prosthetic modules. A modular prosthesis allows a surgeon to accommodate a wide variation in vessel morphology while reducing the necessary inventory of differently sized prostheses. For example, aortas vary in length, diameter and angulation between the renal artery region and the region of the aortic bifurcation. Prosthetic modules that fit each of these variables can be assembled to form a prosthesis, obviating the need for a custom prosthesis or large inventories of prostheses that accommodate all possible combinations of these variables. A modular system may also accommodate deployment by allowing the proper placement of one module before the deployment of an adjoining module.

Modular systems are typically assembled in situ by overlapping the tubular ends of the prosthetic modules so that the end of one module sits partially inside the other module, preferably forming circumferential apposition through the overlap region. This attachment process is called "tromboning." The connections between prosthetic modules are typically maintained by the friction forces at the overlap region and enhanced by the radial force exerted by the internal prosthetic module on the external prosthetic modules where the two overlap. The fit may be further enhanced by stents fixed to the modules at the overlap region.

A length of a vessel which may be treated by these prostheses may have one or more branch vessels, i.e. vessels anastomosed to the main vessel. The celiac, superior mesenteric, left common carotid and renal arteries, for example, are branch vessels of the aorta; the hypogastric artery is a branch vessel of the common iliac artery. If these branch vessels are blocked by the prosthesis, the original blood circulation is impeded, and the patient can suffer. If, for example, the celiac artery is blocked by the prosthesis, the patient can experience abdominal pain, weight loss, nausea, bloating and loose stools associated with mesenteric ischemia. The blockage of any branch vessel is usually associated with unpleasant or even life-threatening symptoms.

When treating a vessel with an endoluminal prosthesis, it is therefore preferable to preserve the original circulation by providing a prosthetic branch that extends from the main prosthetic module to a branch vessel so that the blood flow into the branch vessel is not impeded. For example, the aortic section of the Zenith® abdominal aortic prosthesis (Cook Incorporated, Bloomington, Ind.), described below, can be designed to extend above the renal arteries and to have prosthetic branches that extend into and provide flow to the renal arteries. Alternatively, the iliac branches of a bifurcated aortic prosthesis can be designed to extend into and provide flow to the corresponding hypogastric arteries. Branch extension prosthetic modules ("branch extensions") can form a tromboning connection to the prosthetic branch to extend further into the branch artery. Furthermore, some aneurysms extend into the branch vessels. Deploying prosthetic branches and branch extensions into these vessels may help prevent expansion and/or rupture of these aneurysms. High morbidity and mortality rates are associated with these aneurysms.

Typically, existing prosthetic branches have a straight y- or t-shaped connection to the main endoluminal graft. Examples of such prosthetic branches and their associated branch extensions are shown in U.S. Pat. Nos. 6,520,988 and 6,579,309. Some of these branch extensions and their associated prosthetic branches may dislocate, kink and/or cause poor hemodynamics. These problems may lead to thrombogenesis and endoleaks at the interconnection of the prosthetic branch and branch extension.

BRIEF SUMMARY

In one aspect, an endoluminal prosthesis may be provided and comprise a prosthetic trunk and first and second prosthetic branches. The prosthetic trunk comprises a trunk lumen extending therethrough and a trunk wall. The first prosthetic branch extends from the trunk wall and comprises a first branch lumen extending therethrough and a branch wall. The second prosthetic branch extends from the branch wall and comprises a second branch lumen. The first and second branch lumens are both in fluid communication with the trunk lumen through the trunk wall and the second branch lumen is in fluid communication with the first branch lumen through the branch wall.

At least one, and in some examples both, of the first and second prosthetic branches may be disposed longitudinally along and circumferentially about the prosthetic trunk. In some examples, one of the prosthetic branches may be disposed longitudinally along and circumferentially about the other of the prosthetic branches. The prosthetic branches may have any suitable shape. For example, at least one of the branches may be tapered.

In another aspect, an endoluminal prosthesis may be provided and comprise a prosthetic trunk and a stent attached to the prosthetic trunk. The prosthetic trunk comprises a trunk lumen extending therethrough, a wall, and an anastomosis in the wall. The stent has a generally tubular stent body that provides radial support to the prosthetic trunk. The stent body alternates endlessly about a longitudinal axis of the prosthetic trunk between a first stent pattern and a second stent pattern. The first stent pattern comprises a loop having a contour that contacts and supports the entire perimeter of the anastomosis. In some examples, the second stent pattern has a generally zigzag shape. The loop may have any contour that matches the contour of the anastomosis. In some examples, the loop has an ovoid shape.

In another aspect, an endoluminal prosthesis may be provided and comprise a prosthetic trunk having a trunk lumen, a prosthetic branch having a branch lumen, and a stent. The stent has a stent pattern that alternates endlessly about the perimeter of the stent between a first tubular stent region disposed about a first axis and a second tubular stent region disposed about a second axis. The first stent region is attached to and supports at least a portion of the prosthetic trunk and the second stent region is attached to and supports at least a portion of the prosthetic branch.

In some examples, the endless alternating stent pattern includes a generally zigzag shape. The first and second stent regions may have diameters that are generally the same, or they may have different diameters. The first stent axis and the second stent axis are arranged according to the arrangement of the prosthetic trunk and the prosthetic branch. For example, the first and second stent axes may be generally collinear. In some examples, the stent may have a figure-8 shape.

In some examples, the prosthetic branch may be disposed, at least in part, inside the prosthetic trunk lumen. Likewise, the prosthetic branch may be disposed, at least in part, outside the prosthetic trunk lumen. The stent may be disposed on the interior and/or exterior surface of the prosthetic trunk and the prosthetic branch. For example, at least a portion of the first stent region may be disposed on an interior surface of the prosthetic trunk. In these examples, at least a portion of the first stent region may be disposed on a surface of the prosthetic branch, for example an exterior surface of the prosthetic branch. In some examples, at least a portion of the second stent region may be disposed on an exterior surface of the prosthetic branch.

Other aspects of the present invention will become apparent in connection with the following description of the present invention.

BRIEF DESCRIPTION OF THE DRAWINGS

FIG. 1 shows a schematic anterior view of an endoluminal prosthesis with a y-shaped prosthetic branch;

FIG. 2 shows a schematic anterior view of an endoluminal prosthesis with a helical prosthetic branch;

FIG. 3b shows another side view of the embodiment of FIG. 3a;

FIG. 4b shows a schematic front view of the embodiment of FIG. 4a;

FIG. 4c shows a skeletal schematic front view of the embodiment of FIG. 4a;

FIG. 6a shows a schematic anterior view of an embodiment of an endoluminal prosthesis;

FIG. 6b shows a skeletal view of the embodiment of FIG. 6a;

FIG. 7b shows a top view the embodiment of FIG. 7a;

FIG. 8b shows a side view of the embodiment of FIG. 8a;

FIG. 8c shows another side view of the embodiment of FIG. 8a;

FIG. 8d shows a posterior view of the embodiment of FIG. 8a;

FIG. 9b shows a schematic anterior view of the embodiment of FIG. 9a;

FIG. 10b shows a schematic top view of the embodiment of FIG. 10a;

FIG. 12b shows a schematic anterior view of the embodiment of FIG. 12a;

FIG. 12c shows a schematic top view of the embodiment of FIG. 12a;

FIG. 13a shows a schematic anterior view of an embodiment of an endoluminal prosthesis that has crimps;

FIG. 13b shows a skeletal view of the embodiment of FIG. 13a;

FIG. 13c shows a schematic top view of the embodiment of FIG. 13a;

FIG. 18 shows a helical branch having a helical stent;

FIG. 19 shows the helical stent coiled at the branch ostium;

FIG. 20 shows a stent at the branch anastomosis;

FIGS. 23a-d shows different views of a stent designed to maintain the shape of a branch-trunk anastomosis;

DETAILED DESCRIPTION

Figure 3A:
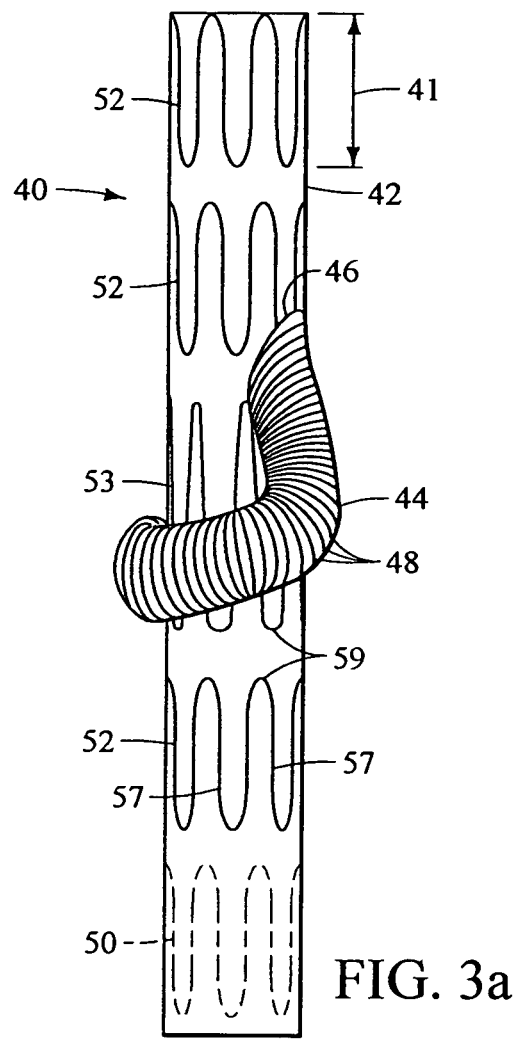
FIG. 3a shows a side view of an embodiment of an endoluminal prosthesis with a helical prosthetic branch.

Branch vessel prostheses may be formed with prosthetic branches that are disposed longitudinally and circumferentially with respect to the prosthetic trunk. Such prosthetic branches are termed "helical" prosthetic branches. A branch extension may be connected to the distal end of the helical prosthetic branch by tromboning.

The helical turn in the prosthetic branch may reduce the forces on the branch extension by shifting the hemodynamic forces from the prosthetic branch and the interconnection between the branch extension to the prosthetic trunk. This may help prevent the branch extension from pulling out under those forces. The helical turn may also allow a wider variation in the radial orientation ("angle of access") of the prosthetic trunk and may prevent kinking of the prosthetic branch or branch extension. This design may also improve the hemodynamics by, for example, promoting laminar flow.

To help understand this description, the following definitions are provided.

The term "prosthesis" means any replacement for a body part or function of that body part. It can also mean a device that enhances or adds functionality to a physiological system.

The term "endoluminal" describes objects that are found or can be placed inside a lumen in the human or animal body. A lumen can be an existing lumen or a lumen created by surgical intervention. This includes lumens such as blood vessels, parts of the gastrointestinal tract, ducts such as bile ducts, parts of the respiratory system, etc. An "endoluminal prosthesis" is thus a prosthesis that can be placed inside one of these lumens.

The term "stent" means any device or structure that adds rigidity, expansion force or support to a prosthesis. A Z-stent is a stent that has alternating struts and peaks (i.e., bends) and defines a generally cylindrical lumen. The "amplitude" of a Z-stent is the distance between two bends connected by a single strut. The "period" of a Z-stent is the total number of bends in the Z-stent divided by two, or the total number of struts divided by two.

The term "pull-out force" means the maximum force of resistance to partial or full dislocation provided by a modular prosthesis. The pull-out force of a prosthesis having two interconnected modules can be measured by an MTS Alliance RT/5® tensile testing machine (MTS Corporation, Eden Prairie, Minn.). The MTS machine is connected to a computer terminal that is used to control the machine, collect, and process the data. A pressurization pump system is attached to the load cell located on the tensile arm of the MTS machine. One end of the prosthesis is connected to the pressurization pump, which provides an internal pressure of 60 mm Hg to simulate the radial pressure exerted by blood upon the device when deployed in vivo. The other end of the prosthesis is sealed. The prosthesis is completely immersed in a 37° C. water bath during the testing to simulate mean human body temperature. The MTS machine pulls the devices at 0.1 mm increments until the devices are completely separated. The computer will record, inter alia, the highest force with which the modules resist separation, i.e. the pull-out force.

The term "endoleak" refers to a leak around or through an endoluminal prosthesis. Endoleaks can occur through the fabric of a prosthesis, through the interconnections of a modular prosthesis, or around the ends of the prosthesis, inter alia. Endoleakage may result in the repressurizing of an aneurysm.

The term "branch vessel" refers to a vessel that branches off from a main vessel. Examples are the celiac and renal arteries which are branch vessels to the aorta (i.e., the main vessel in this context). As another example, the hypogastric artery is a branch vessel to the common iliac, which is a main vessel in this context. Thus, it should be seen that "branch vessel" and "main vessel" are relative terms.

The term "prosthetic trunk" refers to a portion of a prosthesis that shunts blood through a main vessel. A "trunk lumen" runs through the prosthetic trunk.

The term "prosthetic branch" refers to a portion of a prosthesis that is anastomosed to the prosthetic trunk and shunts blood into and/or through a branch vessel.

A "peripheral prosthetic branch" is a prosthetic branch that is anastomosed to the side of a prosthetic trunk. This is distinguished from a "contralateral prosthetic branch," which is a prosthetic branch that results from a "pant leg" bifurcation. The bifurcation may be asymmetrical, i.e. the two "legs" may have different diameters or lengths.

The term "branch extension" refers to a prosthetic module that can be deployed within a branch vessel and connected to a prosthetic branch.

The term "helical" or "helically" describes a prosthetic branch that is oriented circumferentially about and longitudinally along a prosthetic trunk. "Helical" is not restricted to a regular helix or a full 360° circumferential turn.

"Longitudinally" refers to a direction, position or length substantially parallel with a longitudinal axis of a reference, and is the length-wise component of the helical orientation.

"Circumferentially" refers to a direction, position or length that encircles a longitudinal axis of reference, and is the radial component of a helical orientation. Circumferential is not restricted to a full 360° circumferential turn nor a constant radius.

"Anastomosis" refers to a connection between two lumens, such as the prosthetic trunk and prosthetic branch that puts the two in fluid communication with each other. "Anastomosing" refers to the process of forming an anastomosis.

The term "angle of incidence" refers to the angle of intersection of a longitudinal axis of a prosthetic branch and a line on the prosthetic trunk that runs longitudinally through the anastomosis.

The term "skew" refers to the angle of out-of-plane rotation of the prosthetic branch, relative to the longitudinal axis of the prosthetic trunk, as measured at or near the anastomosis.

The term "angle of access" refers to the acceptable range of radial orientation of the branched prosthesis about the longitudinal axis of the prosthetic trunk. Through that range, the distal ostium of the prosthetic branch is close enough to the branch vessel so that the branch extension can be properly deployed into the branch vessel to form a connection with the prosthetic branch.

FIG. 1 shows a schematic representation of a prosthetic branch 12 anastomosed to the prosthetic trunk 10 in a y-configuration. A branch extension 14 forms a tromboning connection with the prosthetic branch 12. The branch extension 14 is positioned at a 45° angle 16 to the prosthetic trunk 10 to accommodate the anatomy in which the total prosthesis is designed to sit. The angle 16 of the branch extension 14 causes it to bear forces in the y-direction 15, as a result of the blood pressure and momentum of the blood flow through the prosthetic branch 12 and branch extension 14.

The connection between the branch extension 14 and the prosthetic branch 12 is maintained by friction forces. Therefore, if the forces in the y-direction 15 borne by the branch extension 14 exceed the friction forces that maintain the connection, the branch extension 14 may disconnect from the branch 12. This is a dangerous outcome for the patient, as the disconnection can result in a repressurization of the region surrounding the prosthetic branch 12 and the prosthetic trunk 10.

FIG. 2 shows a schematic representation of one embodiment of the present invention. In this embodiment, the prosthetic branch 22 is anastomosed to the prosthetic trunk 20. A branch extension 25 forms a tromboning connection with the prosthetic branch 22. The branch extension 25 is positioned at an about 60-70° angle 24 to the prosthetic trunk 20 to accommodate the anatomy in which the total prosthesis is designed to sit, although it can be placed at any suitable angle. The prosthetic branch 22 turns about the prosthetic trunk 20 to form a partial helix.

The angle 24 of the prosthetic branch 22 creates flow forces in the y-direction 23 as a result of the momentum of the blood flow through and physiological blood pressure in the branch 22, just as in the prosthesis of FIG. 1. However, unlike in FIG. 1, the prosthetic branch 22 bears much of these y-forces and is supported by its attachment 27 to the prosthetic trunk 20. Thus, the attachment 27 bears at least some of the y-direction forces instead of the load being placed on the interconnection 21 and the prosthetic branch 22. This helps prevent a common failure mode known in branched prostheses. A prosthetic extension module 25 may form a tromboning interconnection with the prosthetic branch 22.

FIG. 3a shows another embodiment of the present invention. This embodiment is suitable for deployment into the left iliac artery and branching into the left hypogastric artery, although it can be adapted for other vessels. An embodiment suitable for deployment into the right iliac artery could be a longitudinal mirror-image of the prosthesis 40 of FIG. 3a. The prosthesis 40 includes a prosthetic trunk 42 and a peripheral prosthetic branch 44. For this prosthesis 40, and the others discussed herein, the prosthetic branch 44 preferably curves around the anterior of the prosthetic trunk 42 as shown, although, as an alternative it may curve around the posterior of the prosthetic trunk 42. The prosthetic branch 44 is in fluid communication with the prosthetic trunk 42 through the anastomosis 46. The anastomosis 46 is preferably infundibular, i.e. funnel-shaped, as shown. This mimics a typical physiological anastomosis, and improves the hemodynamics of flow into the prosthetic branch 44. The prosthetic branch 44 is preferably sutured to the prosthetic trunk 42 to form a blood-tight seal. The proximal end of the prosthetic trunk may have a scallop cut into it in order to facilitate deployment of the prosthesis 40, described below.

The prosthetic trunk 42 is preferably made of woven polyester having a twill weave and a porosity of about 350 ml/min/cm$^2$ (available from Vascutek® Ltd., Renfrewshire, Scotland, UK). The prosthetic branch 44 is preferably made of seamless woven polyester. The prosthetic trunk 42 and prosthetic branch 44 can also be made of any other at least substantially biocompatible material including such fabrics as other polyester fabrics, polytetrafluoroethylene (PTFE), expanded PTFE, and other synthetic materials known to those of skill in the art. Naturally occurring biomaterials, such as collagen, are also highly desirable, particularly a derived collagen material known as extracellular matrix (ECM), such as small intestinal submucosa (SIS). Other examples of ECMs are pericardium, stomach submucosa, liver basement membrane, urinary bladder submucosa, tissue mucosa, and dura mater. SIS is particularly useful, and can be made in the fashion described in U.S. Pat. No. 4,902,508 to Badylak et al.; U.S. Pat. No. 5,733,337 to Carr; U.S. Pat. No. 6,206,931 to Cook et al.; U.S. Pat. No. 6,358,284 to Fearnot et al.; 17 Nature Biotechnology 1083 (November 1999); and WIPO Publication WO 98/22158 of May 28, 1998, to Cook et al., which is the published application of PCT/US97/14855. All of these references are incorporated herein by reference. It is also preferable that the material is non-porous so that it does not leak or sweat under physiologic forces.

Graft materials may also include porous polymer sheet of a biocompatible material. Examples of biocompatible polymers from which porous sheets can be formed include polyesters, such as poly(ethylene terephthalate), polylactide, polyglycolide and copolymers thereof; fluorinated polymers, such as polytetrafluoroethylene (PTFE), expanded PTFE (ePTFE) and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above. Preferably the porous sheet is made of one or more polymers that do not require treatment or modification to be biocompatible. More preferably, the porous sheet includes a biocompatible polyurethane. Examples of biocompatible polyurethanes include Thoralon® (Thoratec, Pleasanton, Calif.), Biospan®, Bionate®, Elasthane®, Pursil® And Carbosil® (Polymer Technology Group, Berkeley, Calif.).

Preferably the porous polymeric sheet contains the polyurethane Thoralon®. As described in U.S. Patent Application Publication No. 2002/0065552 A1, incorporated herein by reference, Thoralon® is a polyetherurethane urea blended with a siloxane-containing surface modifying additive. Specifically, the polymer is a mixture of base polymer BPS-215 and an additive SMA-300. The concentration of additive may be in the range of 0.5% to 5% by weight of the base polymer. The BPS-215 component (Thoratec) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). The SMA-300 component (Thoratec) is a polyurethane comprising polydimethylsiloxane as a soft segment and the reaction product of MDI and 1,4-butanediol as a hard segment. A process for synthesizing SMA-300 is described, for example, in U.S. Pat. Nos. 4,861,830 and 4,675,361, which are incorporated herein by reference. A porous polymeric sheet can be formed from these two components by dissolving the base polymer and additive in a solvent such as dimethylacetamide (DMAC) and solidifying the mixture by solvent casting or by coagulation in a liquid that is a non-solvent for the base polymer and additive.

Thoralon® has been used in certain vascular applications and is characterized by thromboresistance, high tensile strength, low water absorption, low critical surface tension, and good flex life. Thoralon® is believed to be biostable and to be useful in vivo in long term blood contacting applications requiring biostability and leak resistance. Because of its flexibility, Thoralon® is useful in larger vessels, such as the abdominal aorta, where elasticity and compliance is beneficial.

In addition to Thoralon®, other polyurethane ureas may be used as a porous sheet. For example, the BPS-215 component with a MDI/PTMO mole ratio ranging from about 1.0 to about 2.5 may be used. Such polyurethane ureas preferably include a soft segment and include a hard segment formed from a diisocyanate and diamine. For example, polyurethane ureas with soft segments such as polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

The diisocyanate used as a component of the hard segment may be represented by the formula OCN—R—NCO, where —R— may be aliphatic, aromatic, cycloaliphatic or a mixture of aliphatic and aromatic moieties. Examples of diisocyanates include tetramethylene diisocyanate, hexamethylene diisocyanate, trimethyhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methylpentamethylene diamine, 4,4'-methylene dianiline, and mixtures thereof. The amines may also contain oxygen and/or halogen atoms in their structures.

In addition to polyurethane ureas, other polyurethanes, preferably those having a chain extended with diols, may be used as a porous sheet. Polyurethanes modified with cationic, anionic and aliphatic side chains may also be used. See, for example, U.S. Pat. No. 5,017,664. Polyurethanes may need to be dissolved in solvents such as dimethyl formamide, tetrahydrofuran, dimethyacetamide, dimethyl sulfoxide, or mixtures thereof.

The soft segments of these polyurethanes may contain any of the soft segments mentioned above, such as polytetramethylene oxide, polyethylene oxide, polypropylene oxide, polycarbonate, polyolefin, polysiloxane (i.e., polydimethylsiloxane), other polyether soft segments made from higher homologous series of diols, and mixtures of these soft segments. The soft segments may have amine end groups or alcohol end groups.

The hard segment may be formed from any of the diisocyantes listed above, such as 4,4'-diphenylmethane diisocyanate, tetramethylene diisocyanate, hexamethylene diisocyanate, trimethyhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3-dimethoxy-4,4'-biphenyl diisocyanate and mixtures thereof.

The hard segment may be formed from one or more polyols. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, neopentyl alcohol, 1,6-hexanediol, 1,8-octanediol, propylene glycols, 2,3-butylene glycol, dipropylene glycol, dibutylene glycol, glycerol, or mixtures thereof.

In addition, the polyurethanes may also be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

The porous polymeric sheet may contain a polyurethane having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as Elast-Eon 2® and Elast-Eon 3® (Aortech Biomaterials, Victoria, Australia); polytetramethyleneoxide (PTMO) and polydimethylsiloxane (PDMS) polyether-based aromatic siloxane-polyurethanes such as Pursil®-10, -20, and -40 TSPU; PTMO and PDMS polyether-based aliphatic siloxane-polyurethanes such as Pursil AL-5® and AL-10 TSPU®; aliphatic, hydroxy-terminated polycarbonate and PDMS polycarbonate-based siloxane-polyurethanes such as Carbosil®-10, -20, and -40 TSPU (all available from Polymer Technology Group). The Pursil®, Pursil-AL®, and Carbosil® polymers are thermoplastic elastomer urethane copolymers containing siloxane in the soft segment, and the percent siloxane in the copolymer is referred to in the grade name. For example, Pursil-10® contains 10% siloxane. These polymers are synthesized through a multi-step bulk synthesis in which PDMS is incorporated into the polymer soft segment with PTMO (Pursil®) or an aliphatic hydroxy-terminated polycarbonate (Carbosil®). The hard segment consists of the reaction product of an aromatic diisocyanate, MDI, with a low molecular weight glycol chain extender. In the case of Pursil-AL® the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Patent Application Publication No. 2002/0187288 A1, which is incorporated herein by reference.

The porous polymer sheet may contain polytetrafluoroethylene or expanded polytetrafluoroethylene (ePTFE). Films or sheets of ePTFE are typically porous without the need for further processing. The structure of ePTFE can be characterized as containing nodes connected by fibrils. Porous ePTFE can be formed, for example, by blending PTFE with an organic lubricant and compressing it under relatively low pressure. Using a ram type extruder, the compressed polymer is then extruded through a die, and the lubricant is removed from the extruded polymer by drying or other extraction method. The dried material is then rapidly stretched and/or expanded at elevated temperatures. This process can provide for ePTFE having a microstructure characterized by elongated nodes interconnected by fibrils. Typically, the nodes are oriented with their elongated axis perpendicular to the direction of stretch. After stretching, the porous polymer is sintered by heating it to a temperature above its crystalline melting point while maintaining the material in its stretched condition. This can be considered as an amorphous locking process for permanently setting the microstructure in its expanded or stretched configuration. The structure and porosity of ePTFE is disclosed, for example, in U.S. Pat. Nos. 6,547,815 B2; 5,980,799; and 3,953,566; all of which are incorporated herein by reference. Structures of porous hollow fibers can be formed from PTFE, and these porous hollow fibers can be assembled to provide a cohesive porous sheet. Porous hollow fibers containing PTFE are disclosed, for example, in U.S. Pat. No. 5,024,671, which is incorporated herein by reference.

Polymers can be processed to be porous sheets using standard processing methods, including solvent-based processes such as casting, spraying and dipping, and melt extrusion processes. Extractable pore forming agents can be used during processing to produce porous sheets. Examples of extractable pore forming agents include inorganic salts such as potassium chloride (KCl) and sodium chloride (NaCl), organic salts, and polymers such as poly(ethylene glycol) (PEG) and polyvinylpyrrolidone (PVP). Pore forming agents may have a particle size from about 10 μm to about 500 μm, from about 20 μm to about 100 μm, and from about 10 μm to about 40 μm. The amount of pore forming agent relative to the polymer may be from about 20 percent by weight (wt %) to about 90 wt %, and from about 40 wt % to about 70 wt %. These sizes and amounts of pore forming agents can provide for a high degree of porosity following extraction of the pore forming agent. The porosity can be from about 20 wt % to about 90 wt %, and from about 40 wt % to about 70 wt % of the final product.

Porous sheets may be in the form of a microporous, open-celled structure in which the pores are substantially interconnected. Microporous structures can be formed by extrusion of a mixture of polymer and one or more blowing agents. Microcellular polymeric foams can be produced by exposing the polymer to super-critical $CO_2$ under high temperature and pressure to saturate the polymer with the super-critical $CO_2$, and then cooling the polymer. Microcellular foams can be produced as described, for example, in U.S. Pat. Nos. 4,473,665 and 5,160,674, which are incorporated herein by reference. The foaming process can be carried out on extruded polymer tube by first dissolving an inert gas such as nitrogen or $CO_2$ under pressure into the polymer, and then forming microvoids by quickly decreasing the solubility of the gas in the polymer by changing the pressure or temperature, thus inducing thermodynamic instability. Examples of microporous polymeric structures are disclosed, for example, in U.S. Pat. No. 6,702,849 B1, which is incorporated herein by reference.

Porous Thoralon® can be formed by mixing the polyetherurethane urea, the surface modifying additive and a particulate substance in a solvent. Preferably the particulate is insoluble in the solvent, and the particulate may be any of a variety of different particulates or pore forming agents. For example, the solvent may be DMAC, and the particulate may be an inorganic salt. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting void-to-volume ratio can be substantially equal to the ratio of salt volume to the volume of the polymer plus the salt. The resulting pore diameter can also be substantially equal to the diameter of the salt grains.

The porous polymer sheet can have a void-to-volume ratio from about 0.40 to about 0.90. Preferably the void-to-volume ratio is from about 0.65 to about 0.80. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter is measured based on images from a scanning electron microscope (SEM). Formation of porous Thoralon® is described, for example, in U.S. Patent Application Publication Nos. 2003/0114917 A1 and 2003/0149471 A1, both of which are incorporated herein by reference.

The prosthetic branch 44 is preferably, but not necessarily, connected to a branch extension. The prosthetic branch 44 and the branch extension 55 preferably have complementary annular crimps 48. Crimping decreases the risk of kinking, thereby helping preserve the patency of the prosthesis. Complementary crimping or other types of projections at the tromboning interconnection also help maintain the seal and prevent pull-out. Complementary projections on the overlapping modules tend to engage each other to maximize the surface contact between opposing contact surfaces. The prosthetic branch 44 and the branch extension 55 may be only partially crimped.

The crimps shown in FIG. 3a may be created by mounting the prosthetic branch 44, for example, over a mandrel of substantially the same diameter. A thread, wire or other filament is wrapped helically around the prosthetic branch 44. The assembly as described is then heated to a temperature of 138° C. for eight (8) hours. Other temperatures can be used. Typically, the higher the temperature, the shorter the time required for adequate crimping, and vice versa. This induces helical crimping in the wrapped portion of the prosthesis. Annular crimps can also be generated by attaching annular filaments to the prosthetic branch 44 and performing the other steps of this process. The crimp peaks can be spaced by any suitable distance, preferably so that there are about 5 crimp peaks per 10 mm. The crimped interconnection and methods for producing crimps are described in greater detail in U.S. patent application entitled "Endoluminal Prosthesis With Interconnectable Modules," Ser. No. 10/962,001, filed Oct. 8, 2004 (U.S. Patent Application Publication No. 2005/0113905), which is incorporated herein by reference.

The preferred size and shape of the prosthetic module 40 depends on the anatomy in which it is to be implanted and the corresponding module to which this prosthetic module 40 will be connected. Physiological variables, deployment characteristics, and other factors also contribute to the determination of proper size and shape of the prosthetic trunk. The prosthetic trunk 42, if designed for deployment into the iliac artery, preferably has a 12 mm diameter through its length, as shown, but may have a taper, turn or any other suitable geometry. The dimensions of any of the prostheses mentioned herein are only provided as an example, and will preferably be altered to match a particular patient's anatomy.

The stents 50, 52, 53 maintain the patency of the prosthesis and ensure adequate sealing against the surrounding vascular tissue. One goal for stent design and placement, whether internal or external, is to prevent metal-to-metal contact points, prevent contact between two different types of alloys and minimize micromotion. Stent sizing, spacing and design should be determined so that there is no stent-to-stent contact even in tortuous anatomy. Stents are preferably placed to maximize prosthesis flexibility while maintaining patency, as well as reduce material wear and stent fatigue. Furthermore, it is preferable that the stents do not interfere with the prosthetic branch, that they minimize the potential for galvanic corrosion and ensure adequate joint stability. Stent amplitude, spacing and stagger are preferably optimized for each prosthesis design. Any of the stents mentioned herein may have barbs to help decrease prosthesis migration.

The Z-stent design is preferred for straight sections of the aorta; it provides both significant radial force as well as some longitudinal support. In tortuous anatomy, branches or fenestrations, it may be preferable to use alternative stents or modifications to the Z-stent design to avoid stent-to-stent contact. Furthermore, in complex anatomic situations, external stents have the potential to become intertwined with the wires and other devices utilized to ensure branch vessel access, sealing and fixation. In some instance it may be desirable to affix some of the stents to the internal surface of the prosthesis. The Z-stents mentioned herein are preferably made from standard medical grade stainless steel and are soldered using silver standard solder (0 lead/0 tin); other stents may be made from nitinol or other shape-memory metal.

As shown in FIG. 3a, stents 50, 52, 53 are preferably affixed to the prosthesis 40 both internally 50 and externally 52, 53. Preferably Gianturco-type Z-stents of either 14 or 16 gauge (commercially available from Cook Incorporated, Bloomington, Ind.) are employed, as shown. The stents 50, 52, 53 are preferably spaced 4 mm from each other, as measured peak-to-peak. The peaks 59 are preferably staggered for minimal contact with each other. The stents 50, 52 preferably have a 14 mm amplitude 41. The stent 53 nearest to the anastomosis 46 has a 22 mm amplitude, except near the anastomosis 46, where the amplitude is preferably 11 mm so that it does not interfere with the anastomosis 46. This stent 53 may be affixed internally. These stents are preferably self-expanding, but one or more may be balloon expandable.

At least one stent (not shown) is associated with the prosthetic branch 44; it is preferably attached just below the proximal seam 47 of the prosthetic branch 44. The stent is employed to keep the anastomosis 46 open and to prevent kinking upon bending of the prosthetic branch 44. Prolene® 5-0 sutures (not shown) are preferably used for the distal sealing stent 50 while polyester 4-0 sutures (not shown) are used for all other stents 52, 53. Two conventional sutures are preferably tied to each strut 57, and one suture is preferably tied at each peak 59.

The angle of incidence of the prosthetic branch 44 is preferably about 20° to about 60°, and more preferably about 45° with respect to the prosthetic trunk 42; the skew is preferably about 0° to about 30° at the anastomosis 46. The prosthetic branch 44 is preferably anchored to prosthetic trunk 42 by three spaced sutures (not shown) no closer than about 4 mm from the anastomosis 46.

Standard endoluminal techniques may be used to deploy this prosthesis, as described below in further detail. An 18 French sheath may be used, unless loading issues warrant a larger sheath such as a 20 French. Standard radiopaque gold markers (Cook Incorporated, Bloomington, Ind.) are preferably used to assist graft orientation when the prosthesis is viewed through a fluoroscope.

Figure 3C:
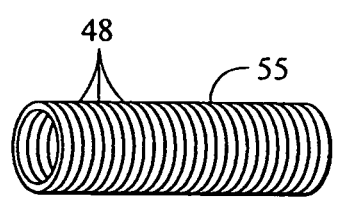
FIG. 3c shows an embodiment of an extension module.
Figure 3B:
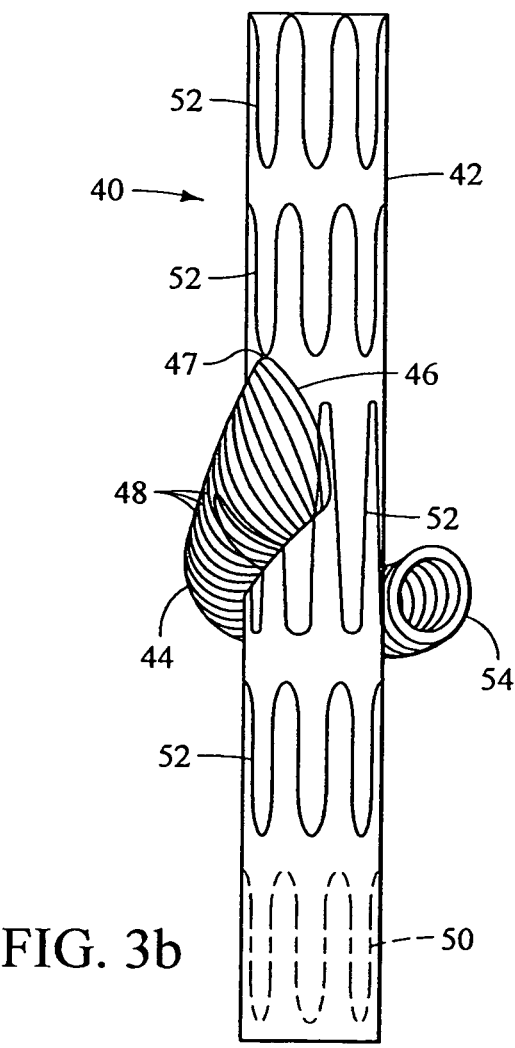

FIG. 3b is an alternative perspective of the prosthesis 40 of FIG. 3a. This shows the shape of the anastomosis 46. The size and shape of the anastomosis 46 may promote laminar flow and other positive hemodynamic characteristics. One method for creating this kind of anastomosis is described below in reference to FIG. 5.

After the prosthesis 40 is implanted, the distal ostium 54 of the prosthetic branch 44 is preferably positioned in the vicinity of the main vessel-branch vessel anastomosis. Then the branch extension 55, shown in FIG. 3c, can be implanted so that it forms a tromboning connection with the prosthetic branch 44. There is preferably a 1 mm or less difference in diameter at the interconnection between the distal ostium 54 of the prosthetic branch 44 and the branch extension 55 to encourage a sealing interconnection. The branch extension 55 may have stents, preferably internal stents, which are less likely to interfere with the seal or fit between corresponding crimps 48. The branch extension 55 can also be a properly sized Viabahn® Endoprosthesis (W. L. Gore & Associates, Inc., Newark, Del.), a Fluency® self-expanding nitinol stent graft (Bard, Tempe, Ariz.) or an iCast® covered stent (Atrium, Hudson, N.H.). One or both ends of the branch extension can have a nitinol ring or coil; a proximal ring or coil preferably engages a corresponding nitinol ring or coil in the helical branch of FIG. 17. The stent can be covered, uncovered or partially covered with PTFE, ePTFE, woven polyester, Thoralon® or other materials. The stents may be self-expanding or balloon-expandable.

Figure 4A:
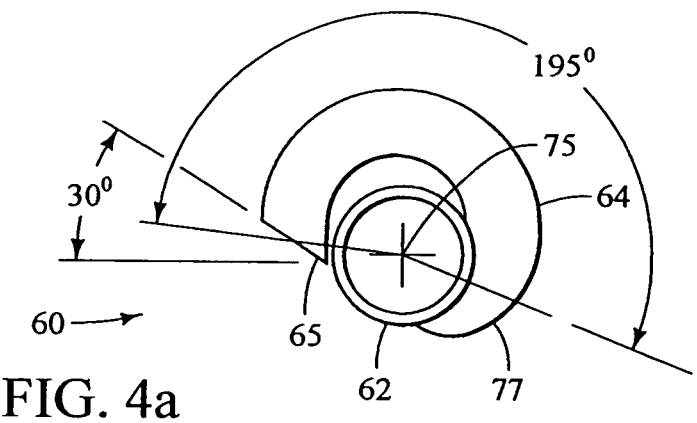
FIG. 4a shows a schematic top view of an embodiment of an endoluminal prosthesis.
Figure 4B:
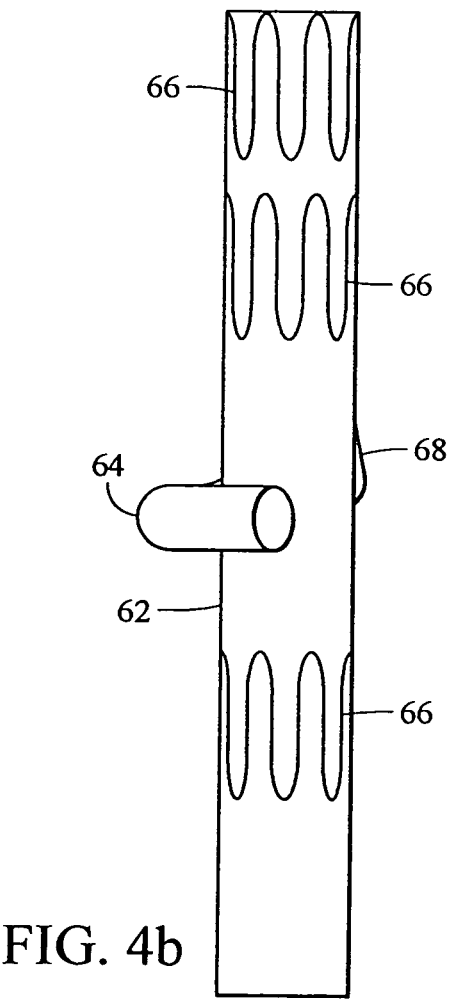
Figure 4C:
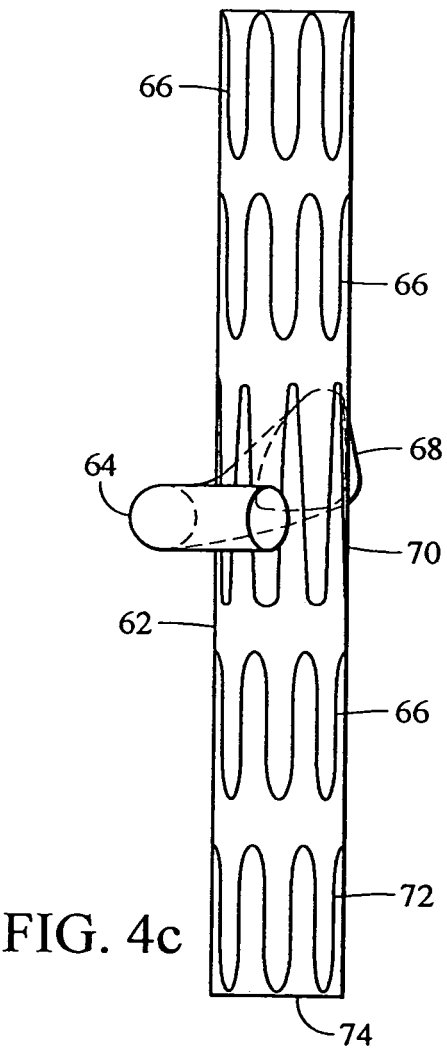

FIG. 4a shows a top view of a prosthesis 60 with a prosthetic trunk 62 and prosthetic branch 64. This prosthesis 60 is designed to be deployed into the right common iliac artery and branch to the right hypogastric artery, although can be adapted for deployment into other vessels. The prosthetic branch 64 is positioned longitudinally along and circumferentially about an external surface of the prosthetic trunk 62, i.e. generally in the form of a helix about the longitudinal axis 75. The prosthetic branch 64 shown in FIG. 4a makes a 195° (or slightly more than one-half the circumference) turn about the prosthetic trunk 62 as measured from the midpoint 77 of the anastomosis to the midpoint of the distal ostium 65, as shown in FIG. 4a. This perspective shows that the distal ostium 65 of the prosthetic branch 64 is beveled by 30°. This may increase the access angle and ease of insertion for the branch extension. A side view of the prosthesis 60 of FIG. 4a is shown in FIGS. 4b and 4c. This prosthesis 60 has three external Z-stents 66 near the prosthetic trunk 62. FIG. 4c, a skeletal view of the prosthesis, shows an internal Z-stent 70 that straddles the anastomosis 68 and an internal stent 72 on the distal terminus 74. One method for forming the enlarged anastomosis 68 is shown in FIGS. 5a-d. The Z-stent 70 that is adjacent the anastomosis may be attached to the graft internally or externally. The flexibility of the prosthetic trunk 62 may be increased by annular or helical crimping of the fabric between the stents of the prosthetic trunk 62.

Figure 5A:
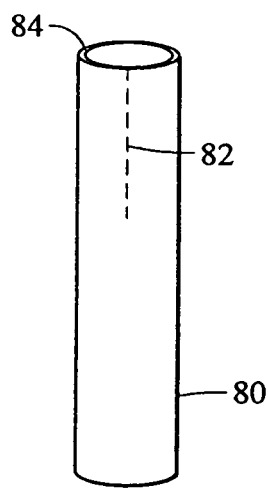
FIGS. 5a-d show preferable steps for creating an enlarged anastomosis.
Figure 5B:
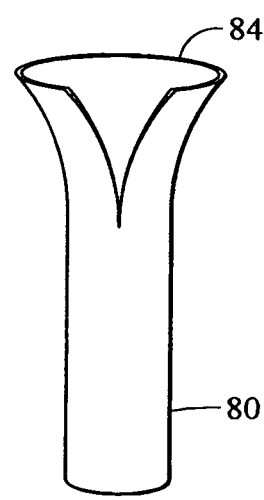
Figure 5D:
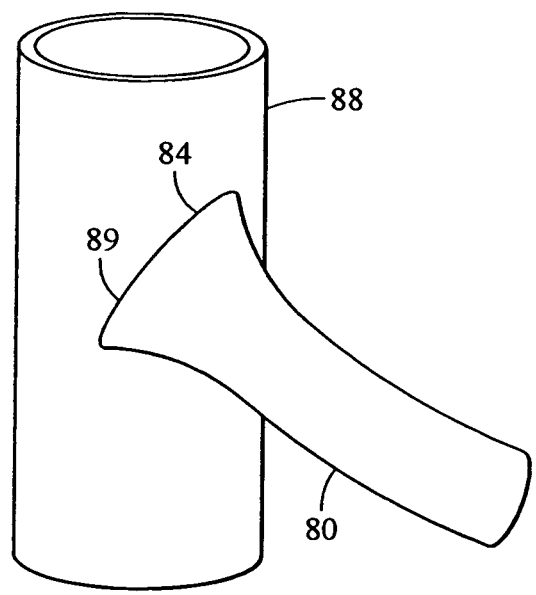
Figure 5C:
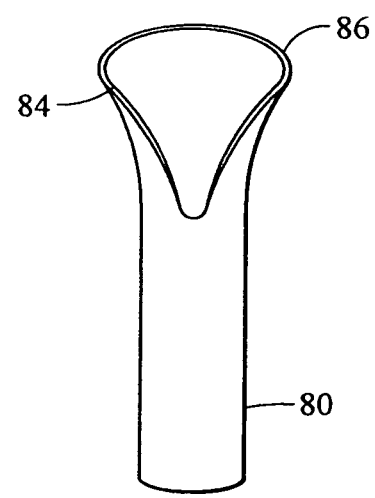

FIG. 5a shows a process for creating an enlarged or "teardrop" anastomosis. The starting material for the prosthetic branch 80 is typically a tubular section of polyester prosthesis fabric. The tubular length of prosthesis fabric may also be flared towards the proximal end 84. The proximal end 84 of the prosthetic branch 80 can be cut at a right angle to the longitudinal axis of the prosthetic branch 80, as shown, or can be beveled or otherwise shaped. The prosthetic branch 80 is cut along a line 82 at its proximal end 84. The line 82 does not have to be parallel to the axis of the tube. Then, as shown in FIG. 5b, the proximal end 84 is splayed. Following splaying, the proximal end 84 can be further shaped to form a new perimeter 86, as shown in FIG. 5c. The splayed perimeter 89 of the proximal end 84 shown in FIG. 5b is preferably sewn to the perimeter of a fenestration (not shown) in the prosthetic trunk 88 of a shape and size to match the splayed perimeter 89, as shown in FIG. 5d. The seam is preferably blood-tight. The fenestration can be oriented in any way relative to the axis of the prosthetic trunk 88 to skew the prosthetic branch 80. The prosthetic branch 80 is then preferably attached to the prosthetic trunk 88 such that it is positioned longitudinally and circumferentially in relation to the prosthetic trunk 88.

FIG. 6a shows a prosthesis 90 with two helical peripheral prosthetic branches 92, 94 extending therefrom. This prosthesis is designed to be positioned within the aorta so that the prosthetic branches 92, 94 can extend to the renal arteries, although this prosthesis design can be adapted for use in other vessels. Branch extensions can then be positioned within the renal arteries so that they form a tromboning connection with the prosthetic branches 92, 94. The uncovered stent 96 is a suprarenal fixation stent which may have barbs (not shown). A skeletal view of the prosthesis 90 of FIG. 6a is shown in FIG. 6b. The stent 95 closest to the distal end 93 of the prosthesis 90 is preferably attached internally, as is the stent 97 near the anastomoses 98. The anastomoses 98 can be as shown or can be the enlarged anastomosis described above with reference to FIG. 5. The prosthetic branches 92, 94 may slope away from the distal end 93 of the prosthesis 90, as shown, or towards the distal end 93 of the prosthesis 90. Stents (not shown) may be used to keep the prosthetic branches 92, 94 patent. Additional prosthetic branches may be anastomosed to the prosthesis 90 to shunt blood to the celiac, SMA, and/or other branch vessels.

Figure 7A:
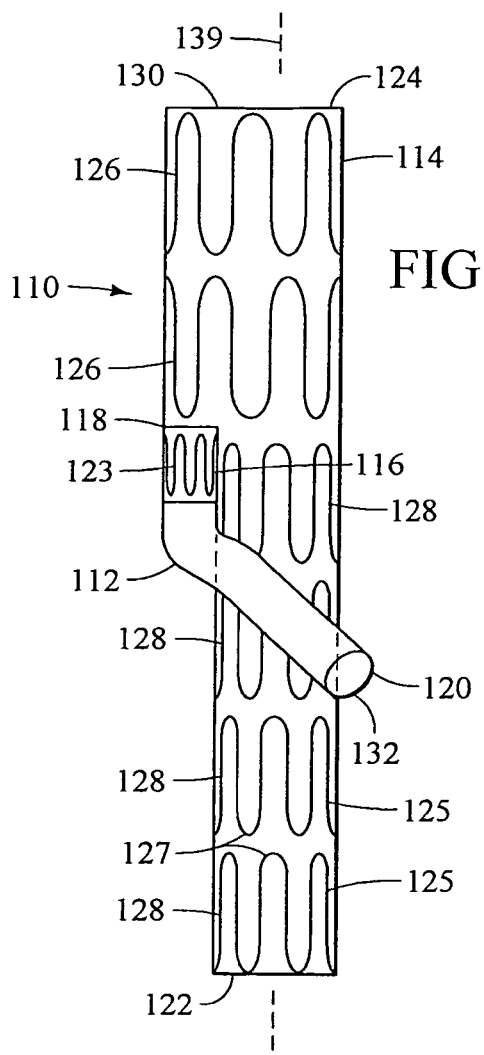
FIG. 7a shows a schematic anterior view of an embodiment of an endoluminal prosthesis.

In FIG. 7a, a skeletal view of a prosthesis 110 with a helical contralateral prosthetic branch 112 is shown. The prosthesis 110 is designed for deployment into a right iliac artery and branching into the hypogastric. Distally to the bifurcation 116, the length of the prosthetic branch 112 is positioned longitudinally and circumferentially with respect to the prosthetic trunk 114 and is seamless along its length. The longitudinal and circumferential placement of the prosthetic branch 112 is secured with one or more sutures (not shown) near and more proximally from the distal ostium 120 of the prosthetic branch 112. For this and other prostheses, the prosthetic branch 112 may extend into the prosthetic trunk 114, proximally to the bifurcation 116, such that the branch lumen (not shown) originates within the lumen (not shown) of the prosthetic trunk 114.

The prosthesis 110 is preferably made from woven polyester described above; the prosthetic branch 112 is preferably crimped. The stents are attached using Prolene® 5-0 sutures. Gold markers (not shown) are preferably attached to the prosthesis 110 in various locations to indicate the position and orientation of the prosthesis 110 under a fluoroscope.

An internal stent 123 is used in the prosthetic branch 112 slightly below the seam 118 and near the bifurcation 116 to keep the prosthetic branch 112 patent and prevent kinking; this stent 123 is preferably internal to the prosthesis 110, but can also be placed externally. The stent 123 is preferably 6 gauge in diameter, has an amplitude of 8 mm and a period of 6. Two prosthetic trunk stents 126 are attached proximally to the bifurcation 116; these stents 126 preferably have a 17 mm amplitude, a diameter of 20 gauge and a period of 9. The prosthesis 110 also has four stents 128 placed distally to the bifurcation 116; these stents 128 preferably have a 14 mm amplitude, a diameter of 14 gauge and a period of 7. The stents 126, 128 are spaced about 4 mm from each other and the peaks 127 of the distal stents 128 are staggered to minimize contact between them. The two most distal stents 125 on the prosthetic trunk 114 can be affixed internally to prevent interference with the deployment of the branch extension.

The distal ostium 120 of the prosthetic branch 112 is preferably 6 mm in diameter. The distal end 122 of the prosthetic trunk 114 is preferably 14 mm in diameter; the proximal ostium 130 of the prosthetic trunk 114 is preferably 20 mm in diameter. The diameter of the prosthetic trunk 114 may be reduced to 12 mm. The distance between the proximal end 124 of the prosthetic trunk 114 to the distal end 132 of the prosthetic branch 112 is preferably about 65 mm. These dimensions are only provided as an example and may be varied to match the anatomy of a specific patient.

Figure 7B:
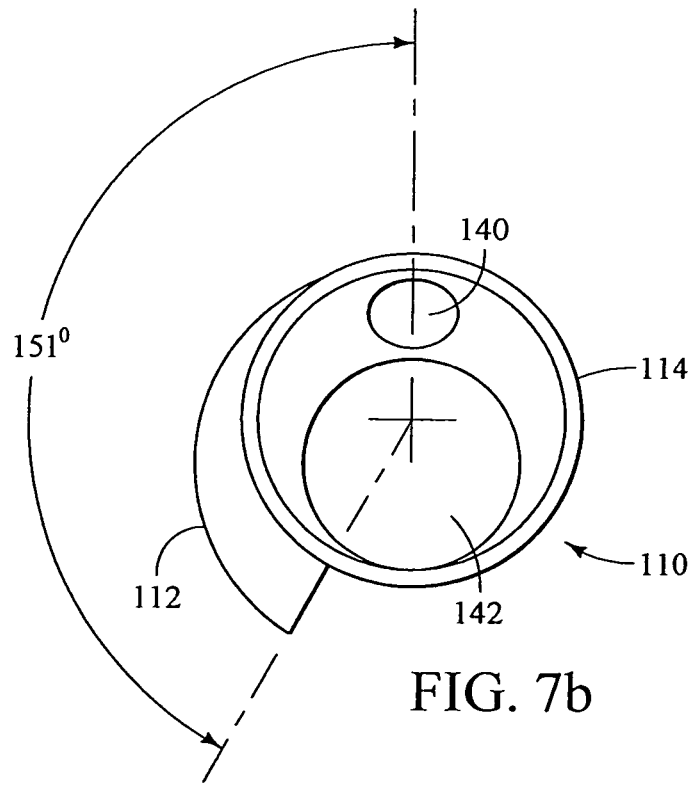

FIG. 7b shows a top view of the prosthesis of FIG. 7a. The prosthetic branch 112 preferably turns 151° about the longitudinal axis 139 of the prosthetic trunk 114.

Figure 8A:
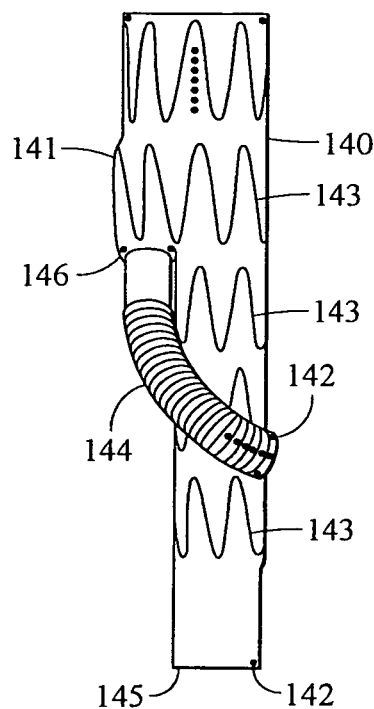
FIG. 8a shows an anterior view of an embodiment of an endoluminal prosthesis.
Figure 8B:
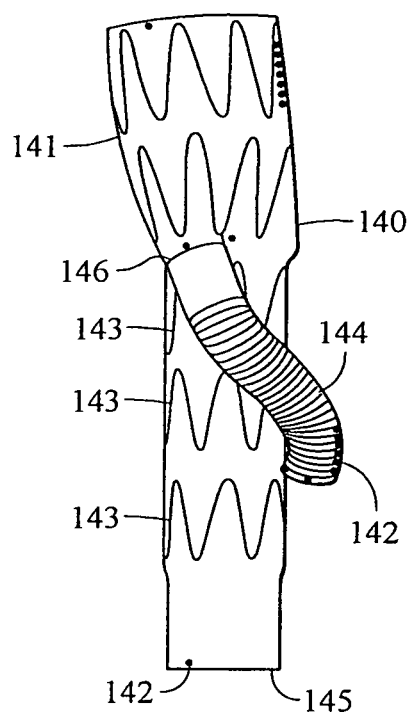
Figure 8C:
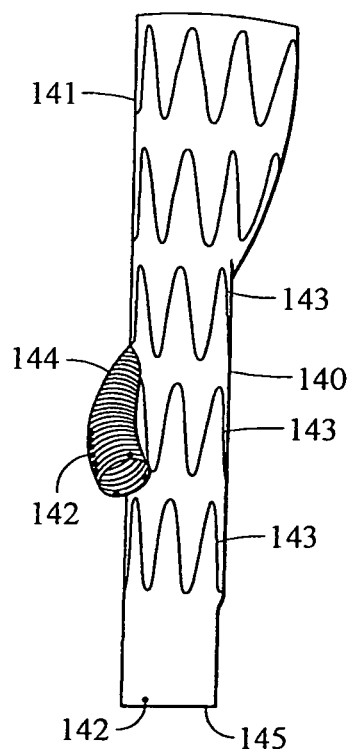
Figure 8D:
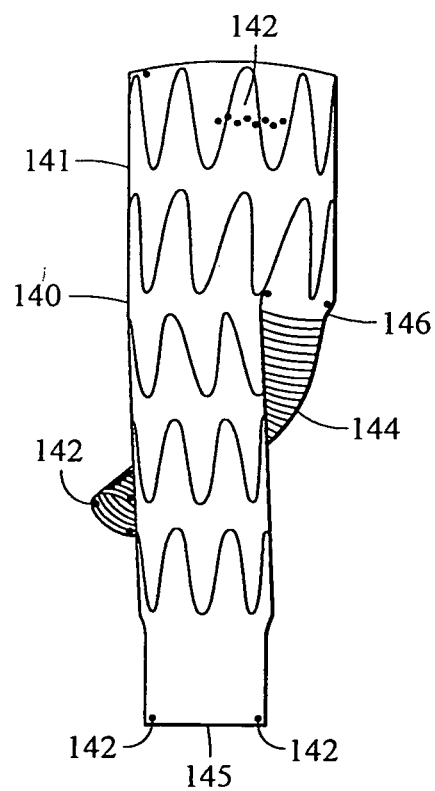

FIGS. 8a-d show different perspectives of a contralateral branched prosthesis 140 similar to the branched prosthesis described in FIGS. 7a-b. This prosthesis 140 is designed for deployment into a right iliac artery and branching into the right hypogastric. Radiopaque markers 142 are sewn to the prosthesis 140. The prosthetic branch 144 is preferably made of woven, crimped polyester. In FIG. 8d, the seam 146 between the prosthetic branch 144 and the prosthetic trunk 141 is evident. The stent (not shown) nearest to the distal end 145 of the prosthetic trunk 141 is attached internally. Any or all of the external stents 143 positioned distally to the seam 146 may be moved internally. Also, the prosthetic branch 144 at the seam 146 could be beveled; this would provide a larger ostium.

Figure 9A:
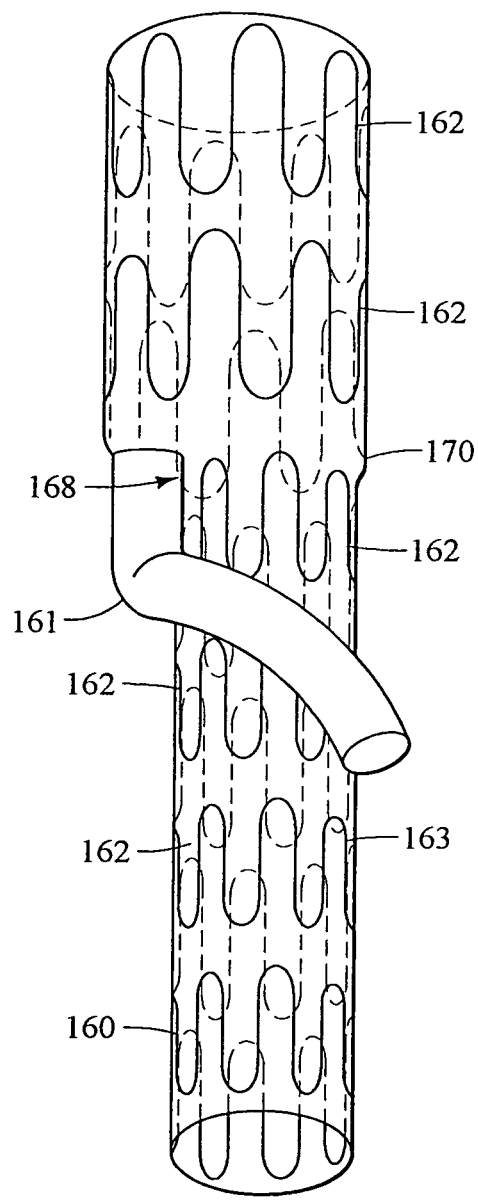
FIG. 9a shows a skeletal anterior view of an embodiment of an endoluminal prosthesis.
Figure 9B:
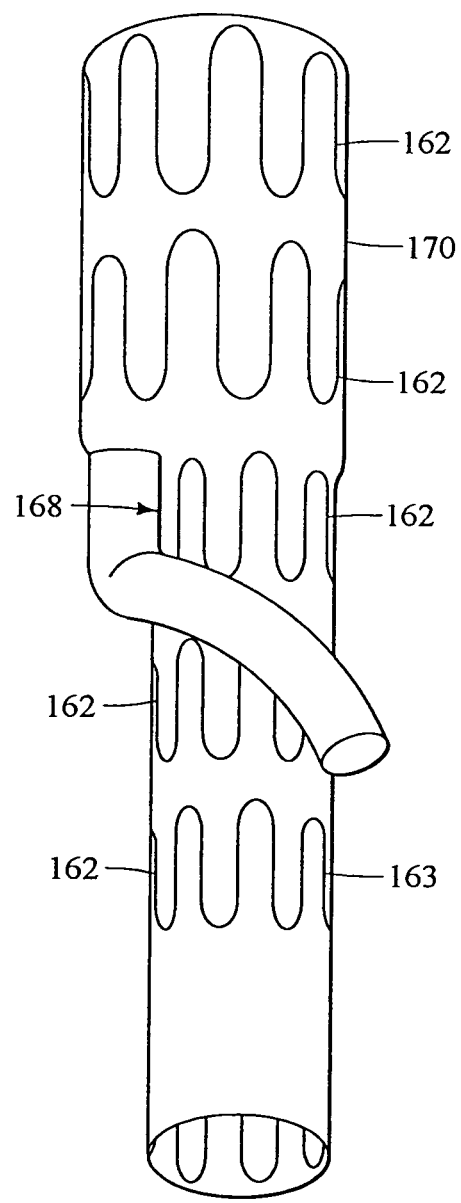

FIGS. 9a-b show an additional embodiment of the contralateral branched prosthesis similar to that described in reference to FIG. 7. FIG. 9a is a skeletal view, showing both the internal stent 160 and the external stents 162. The prosthesis of FIG. 9 has a prosthetic branch 161 that extends vertically down from the bifurcation 168 and then bends around the prosthetic trunk 170. The second-most distal stent 163 can also be affixed internally.

Figure 10A:
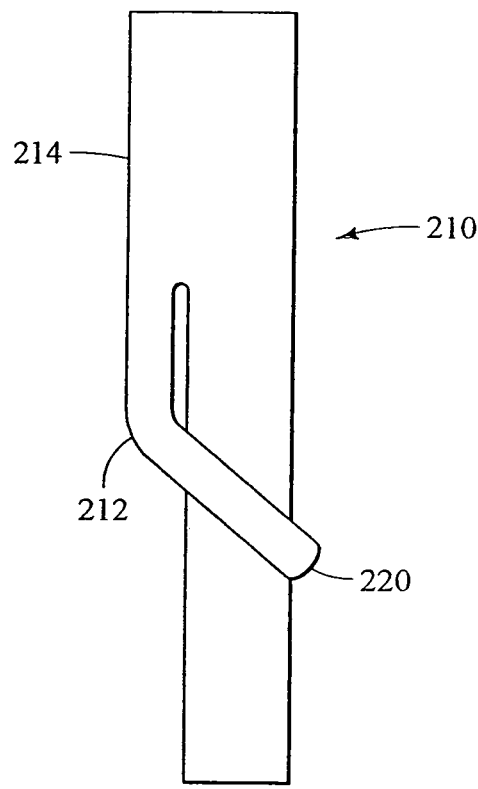
FIG. 10a shows a schematic anterior view of an embodiment of an endoluminal prosthesis.
Figure 10B:
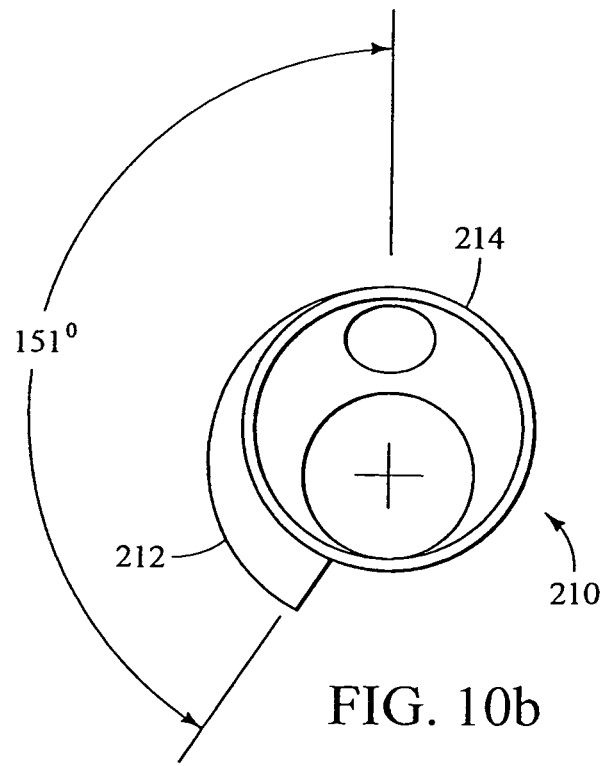

FIGS. 10a-b are schematic representations of the prosthesis described in reference to FIGS. 11a-c, below, and show another embodiment of a contralateral branched prosthesis 210. This prosthesis 210 is designed for deployment into the common iliac and branching into the hypogastric, although it can be adapted for use in any branched vessel. The longitudinal and circumferential placement of the prosthetic branch 212 is secured with one or more sutures near the distal end 220 of the prosthetic branch 212 and more proximally from the distal end 220. The prosthesis 210 is preferably made from woven polyester; the prosthetic branch 212 is preferably made from crimped polyester. FIG. 10b shows the relative orientation of the prosthetic branch 212 to the prosthetic trunk 214; the prosthetic branch 212 preferably turns 151° helically around the prosthetic trunk 214.

Figure 11A:
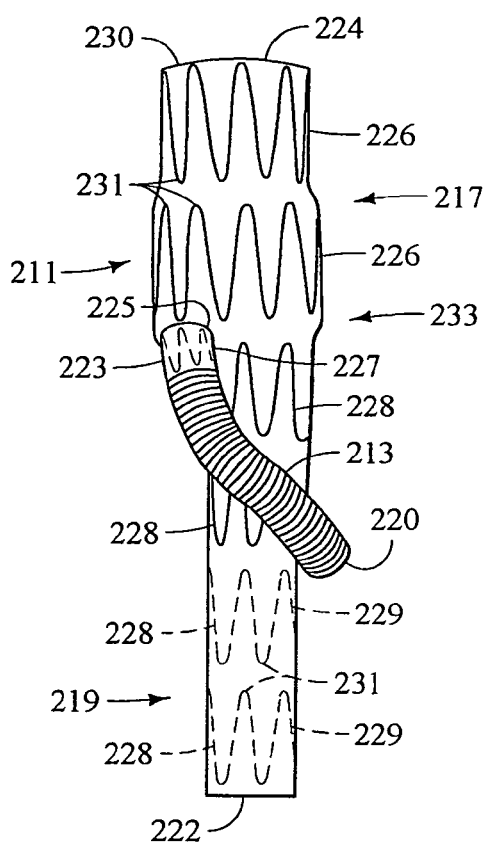
FIGS. 11a-c show three views of an embodiment of an endoluminal prosthesis.
Figure 11B:
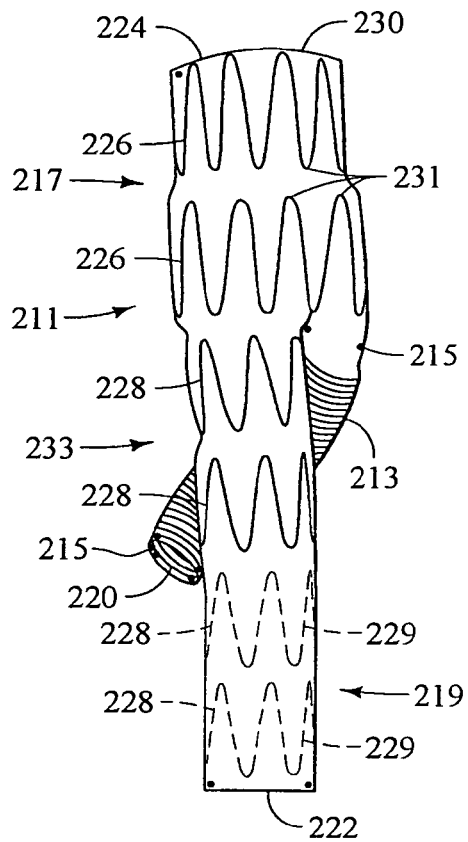
Figure 11C:
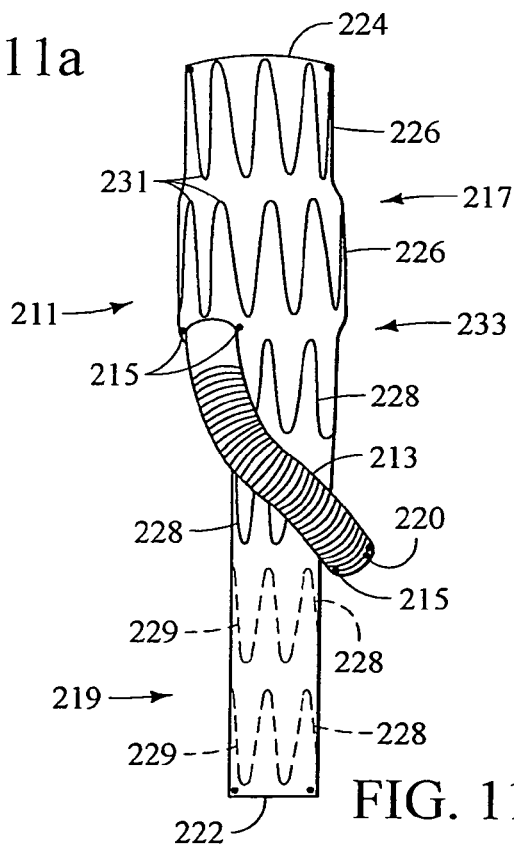

FIGS. 11a-c show a branched contralateral prosthesis 211 suitable for deployment within the right iliac artery and branching into the hypogastric artery. The prosthetic trunk 233 has a proximal section 217 with a diameter of about 20 mm and a distal section 219 with a diameter of about 12 mm. The prosthetic branch 213 originates at the 20 mm diameter proximal section 217 and has a helical path about the 12 mm distal section 219. The helical path of the prosthetic branch 213 is approximately 180° in circumference and approximately 60 mm longitudinally from the seam 225. The pitch is preferably about 45°. The prosthetic branch 213 is preferably 6 mm in diameter through its length and constructed of crimped polyester graft material.

An internal stent 223, shown in FIG. 11a, slightly overlaps the seam 225 so that it is flush with the bifurcation 227 to keep the ostium open and prevent kinking upon bending of the prosthetic branch 213. This stent 223 is preferably attached to the internal surface of the prosthesis 211, but can also be placed externally. The stent 223 is preferably 6 gauge in thickness, 8 mm in height and preferably has a period of 6. Two stents 226 are attached proximally to the bifurcation 227; these stents 226 preferably have an 18 mm amplitude, a diameter of 20 gauge and a period of 10, and are spaced from each other by 2 mm. The prosthesis 211 also has four stents 228 placed distally to the bifurcation 227; these stents 228 have a preferred 14 gauge thickness, 14 mm amplitude, a period of 7, and are spaced by 3 mm. The two most distal stents 229 are preferably attached internally. The stents are preferably attached using Prolene® 5-0. Gold markers 215 are attached to the prosthesis 211 in various locations to indicate the position of the prosthesis 211 under a fluoroscope.

The distal ostium 220 of the prosthetic branch 213 is preferably 6 mm in diameter; the distal end 222 of the prosthetic trunk 214 is preferably 12 mm in diameter; the proximal ostium 230 of the prosthetic trunk 214 is preferably 20 mm in diameter. The dimensions of this prosthesis 211, like the other prostheses described herein, are preferably matched to the anatomy of a specific patient. The peaks 231 of the prosthetic trunk stents 226, 228 are staggered to minimize contact between them. The distance between the proximal end 224 of the prosthetic trunk 214 to the distal ostium 222 of the prosthetic branch 212 is preferably about 70 mm. Deployment of this prosthesis 211 is made easier by the helical design, which allows the "angle of access" to be about 3 times greater than in y- or t-shaped branched prostheses.

Figure 12A:
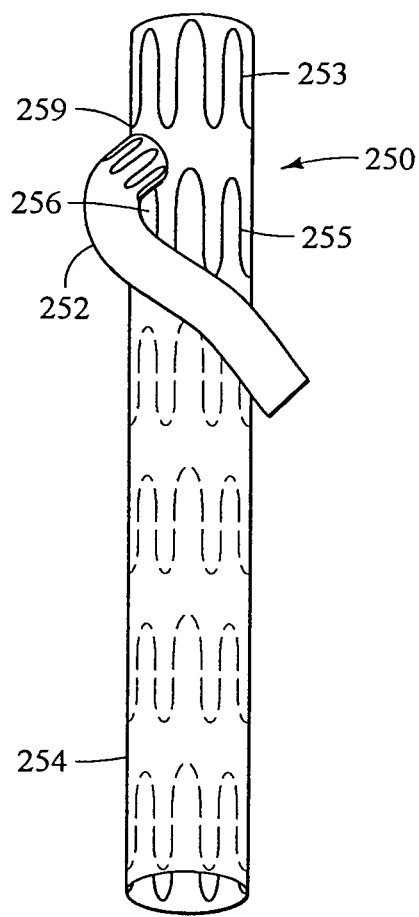
FIG. 12a shows a skeletal anterior view of an embodiment of an endoluminal prosthesis.

FIG. 12a shows a skeletal view of a peripheral branched prosthesis 250. The prosthetic branch 252 of this prosthesis 250 extends at an angle from the side of the prosthetic trunk 254 and then bends back to the prosthetic trunk 254 where it is affixed with sutures. There is a gap 256 between the prosthetic branch 252 and the prosthetic trunk 254. The prosthetic branch 252 is preferably crimped (not shown), seamless and about 6 mm in diameter through its length. The prosthetic trunk 254 is seamless and about 12 mm in diameter through its length. The prosthetic branch 252 is anastomosed to the prosthetic trunk 254 between first 253 and second 255 proximal stents.

Figure 12B:
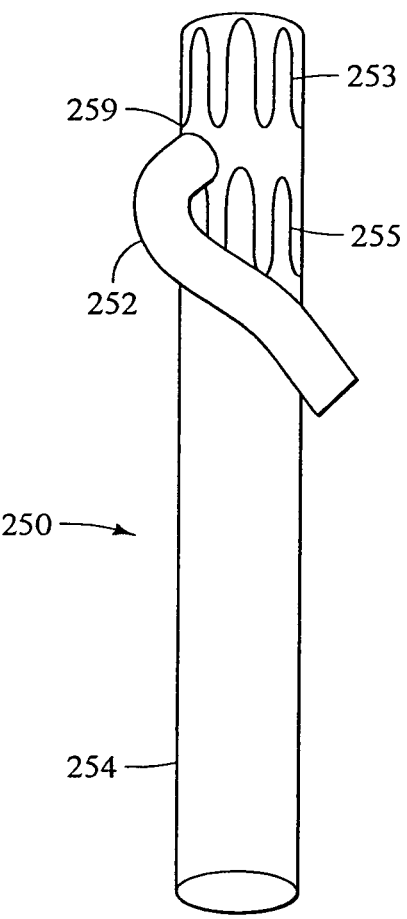
Figure 12C:
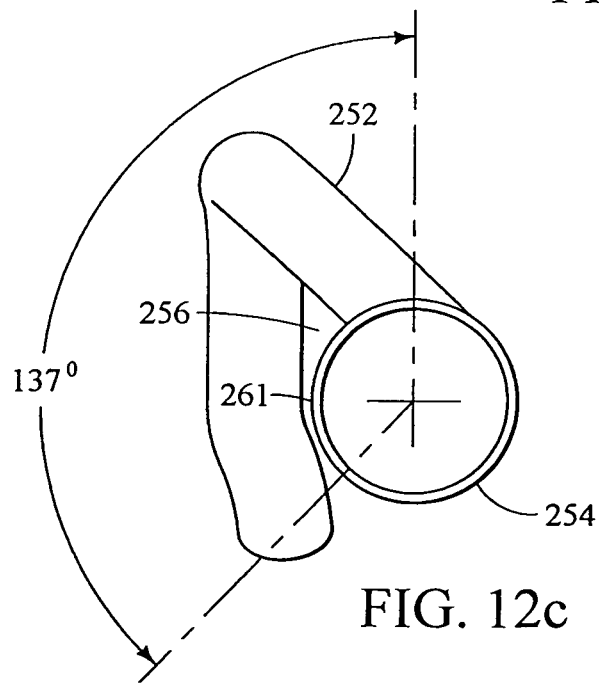

FIG. 12b is an external view of the prosthesis of FIG. 12a. As shown, only the top two stents 253, 255 are attached externally to the prosthesis 250. The other stents shown in FIG. 12a are attached internally. The stents 253, 255 that are around the anastomosis 259 may be affixed internally so that they do not catch on guide wires (not shown) used in deployment of the prosthesis 250. FIG. 12c shows a top view of the prosthesis of FIGS. 12a and 12b. The prosthetic branch 252 turns 137° around the prosthetic trunk 254, and is attached to the prosthetic trunk 254 at a location 261.

An external view of a peripheral branched prosthesis 300 is shown in FIG. 13a. The prosthetic trunk 302 and the prosthetic branch 304 are both preferably made from polyester. The prosthetic branch 304 is preferably crimped (not shown) and seamless. Z-stents 306 of both 14 mm and 22 mm amplitudes are preferably attached to the prosthesis 300 with sutures (not shown). Prolene® 5-0 is used to attach the internal distal stents 312, shown in FIG. 13b; polyester 4-0 is used to attach the proximal stents 310. There are preferably crimps 301 between the stents 306 of the prosthetic trunk 302; these may increase flexibility and decrease kinking of the trunk 302. Gold markers (not shown) may be employed. A nitinol ring or coil may be attached to the prosthetic trunk 302 above the Z-stents; a corresponding nitinol ring or coil is preferably attached to the distal section of the leg to which the peripheral branched prosthesis 300 can mate.

The prosthetic trunk 302 is preferably straight, having a consistent 12 mm diameter throughout. The stent 314 that abuts the prosthetic branch 302 has an amplitude of 22 mm, except as shown in FIG. 13b where the amplitude is 11 mm near the anastomosis 320. This stent 314 is preferably attached externally, as shown; it may be affixed internally. The angle of incidence of the prosthetic branch 304 to the prosthetic trunk 302 at the anastomosis 320 can range from about 20° to about 60°, and is preferably about 45°; the skew relative to the longitudinal axis 324 is preferably between about 0° to about 20° and more preferably about 0°. The length of the prosthetic branch 304 is adjacent to the prosthetic trunk 302; this may improve the distribution of material to reduce packing density during deployment of the prosthesis 300. The prosthetic branch 304 is anchored to prosthetic trunk 302 about 4 mm from the anastomosis 320 using about three sutures; they may be affixed further away to ensure the flexibility of the anastomosis 320.

The most proximal stent 322 is preferably of a 14 mm amplitude and attached externally to the prosthesis 300. The material underneath the most proximal stent 322 is crimped for superior mating to a proximal prosthesis; this stent 322 may also be attached to the inside surface of the prosthesis 300. The enlarged anastomosis 320 described above in reference to FIG. 5 is used to connect the prosthetic branch 304 to the prosthetic trunk 302. The three distal stents 312 are attached internally.

FIG. 13c shows a top view of the prosthesis of FIGS. 13a-b. The prosthetic branch 304 preferably wraps about 150° around the prosthetic trunk 302. The distal ostium 330 of the prosthetic branch 304 is preferably beveled about 30°.

Figure 14A:
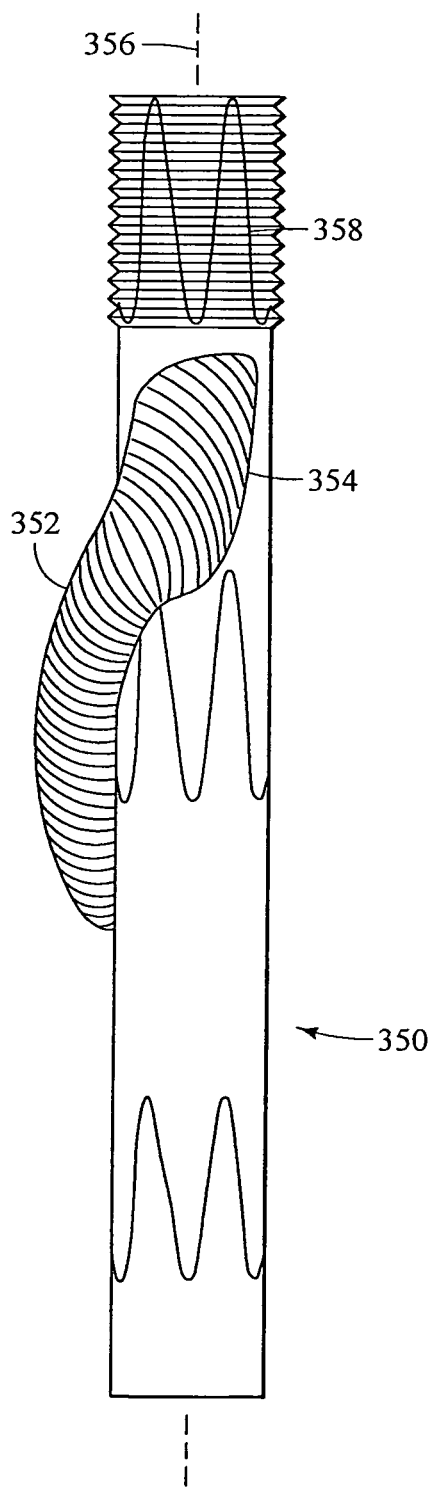
FIGS. 14a-b show two views of an embodiment of an endoluminal prosthesis.
Figure 14B:
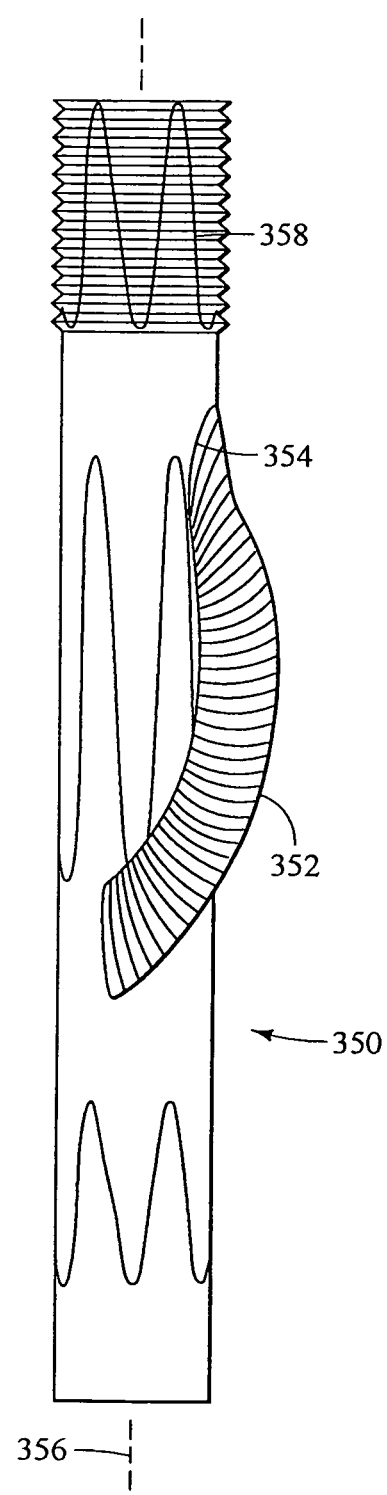

FIGS. 14a-b show a prosthesis 350 that is similar to that described in reference to FIG. 13. The prosthetic branch 352 is preferably made from crimped polyester fabric. The region under the proximal stent 358 is crimped. The anastomosis 354 is preferably enlarged, as described above in reference to FIG. 5. The prosthetic branch 352 is skewed relative to the longitudinal axis 356 of the prosthesis 350 and has an angle of incidence preferably of about 30° to about 40°. The bevel of the prosthetic branch 352 may be trimmed to provide greater clearance for the top stent 358.

Figure 15A:
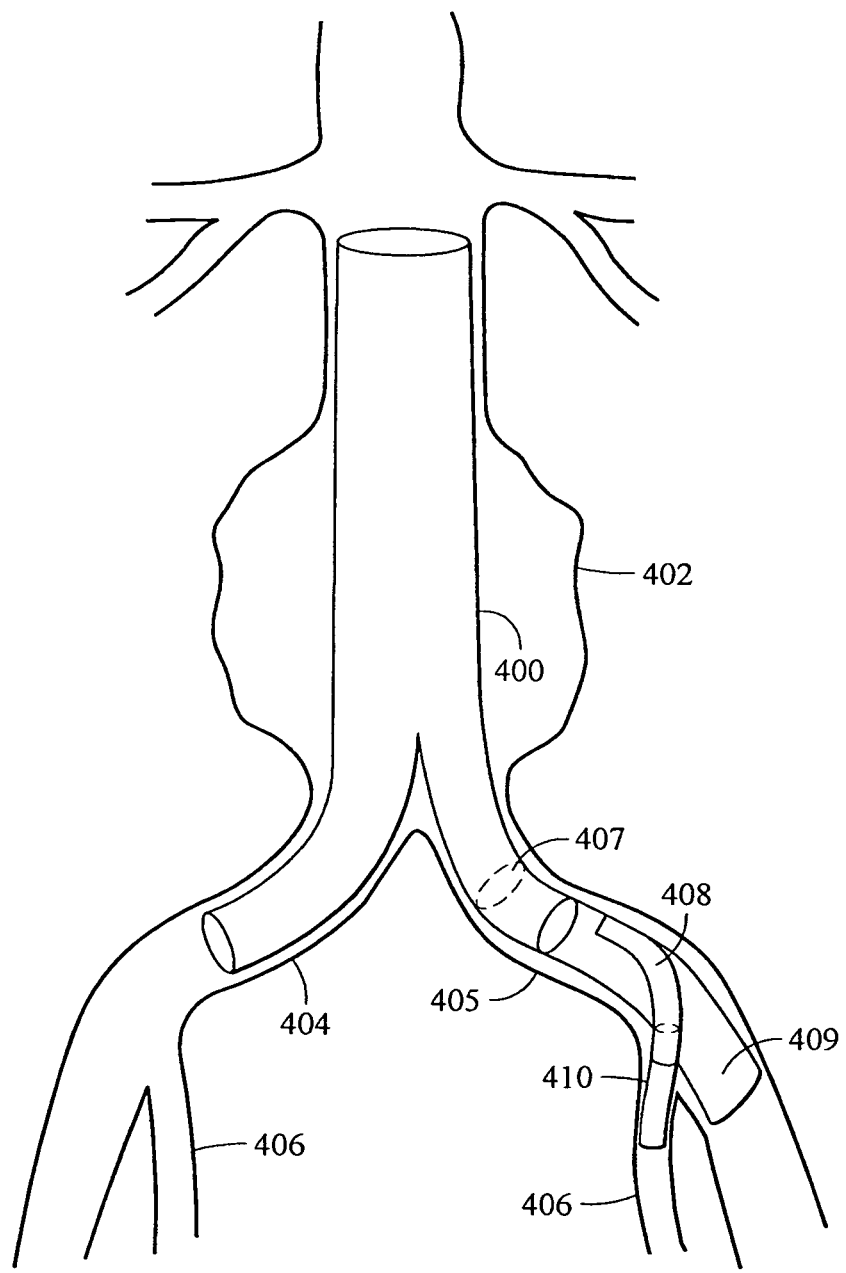
FIG. 15a shows a modular prosthesis that has a prosthetic trunk module in the left iliac artery connected to a prosthetic branch in the hypogastric artery.

FIG. 15a shows a schematic representation of a bifurcated endoluminal prosthesis 400 implanted into an aneurysmal aorta 402. An example of a bifurcated endoluminal prosthesis 400 is the Zenith® AAA stent graft (Cook Incorporated, Bloomington, Ind.). The prosthesis 400 extends into the iliac arteries 404, 405. One of the iliac limbs 407 forms a tromboning interconnection with an iliac extension 409, which, in this context is the prosthetic trunk. The iliac extension (i.e. prosthetic trunk) 409 is anastomosed to a helical prosthetic branch 408. The helical prosthetic branch 408 forms a tromboning interconnection with the hypogastric branch extension 410 which sits in the hypogastric artery 406. The helical prosthetic branch 408 may also curve around the other side (posterior side) of the iliac extension 409.

Figure 15B:
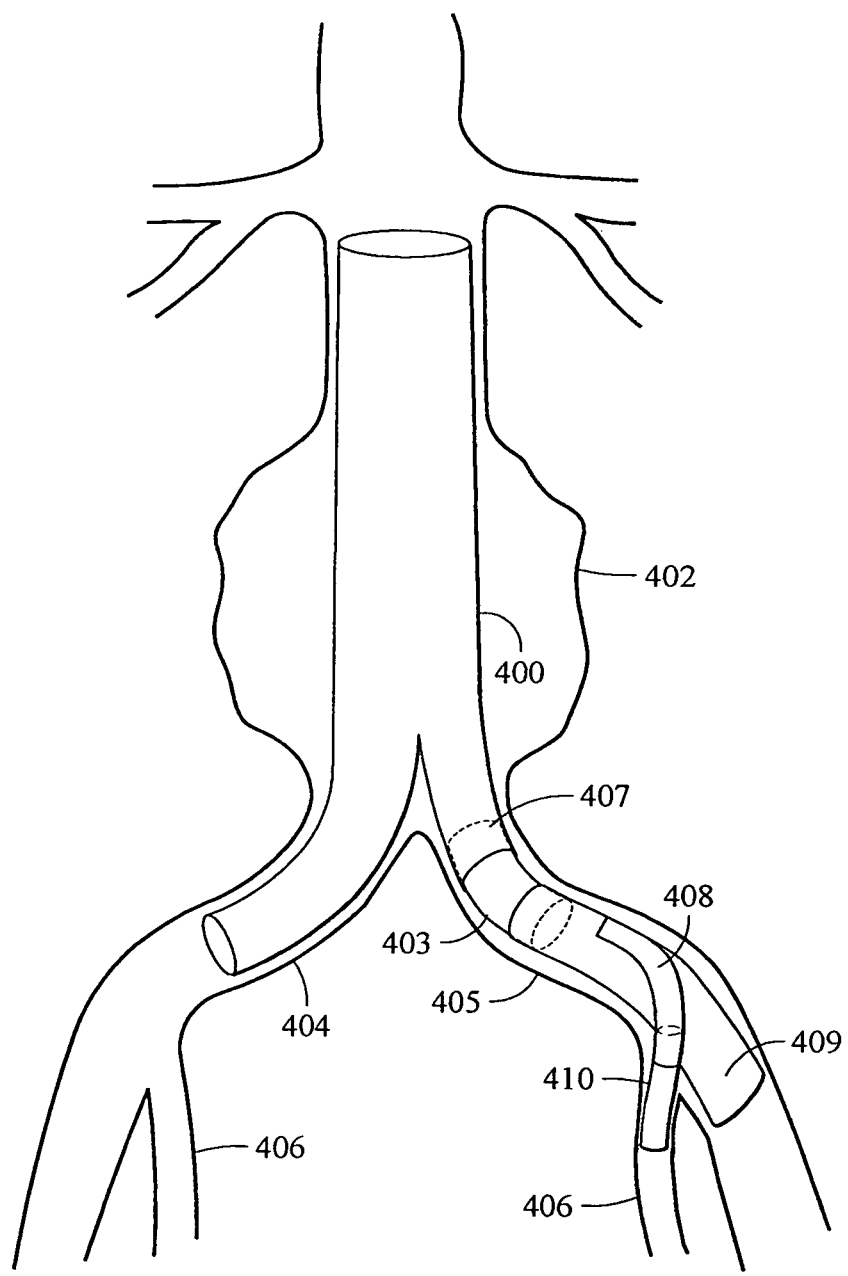
FIG. 15b shows the modular prosthesis of 15a, where the prosthetic trunk and aortic module are connected via an intervening prosthetic module.
Figure 15C:
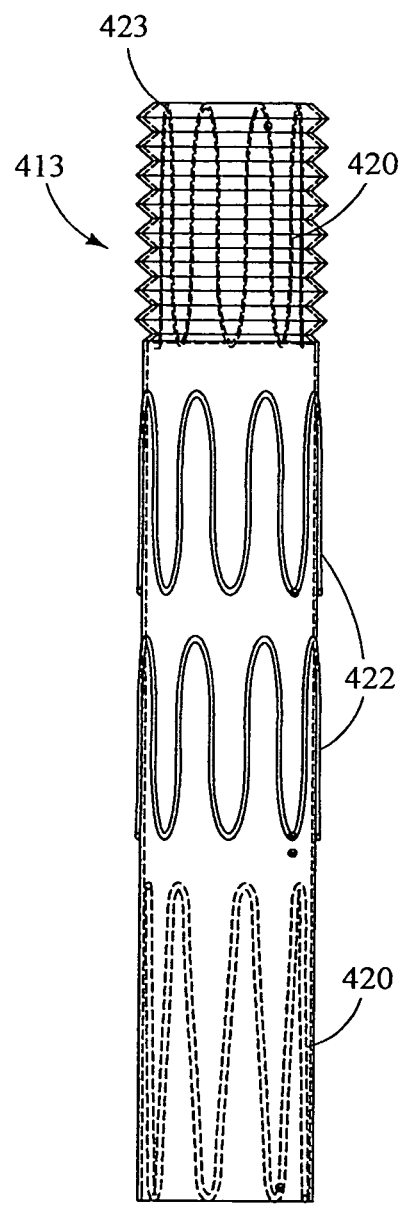
FIG. 15c shows an intervening prosthetic module.

In FIG. 15b, there is a modular prosthesis that is similar to that shown in FIG. 15a. However, the iliac extension 409 of FIG. 15b is connected to the iliac leg 407 via an intervening prosthetic module 403. An example of an intervening prosthetic module 413 is shown in FIG. 15c. The distal end 423 of the intervening prosthetic module 413 is crimped and has an internal stent 420. External stents 422 are attached to the outside of the module 413. The intervening prosthetic module 403 is preferably deployed after the aortic stent graft 400 and the iliac extension 409 are deployed, so that the intervening prosthetic module 403 is overlapped on both ends. The crimps on the distal end 423 preferably engage corresponding crimps on the proximal end of the iliac extension 409. Either the aortic graft 400 or the iliac extension 409 may be deployed first.

Figure 16:
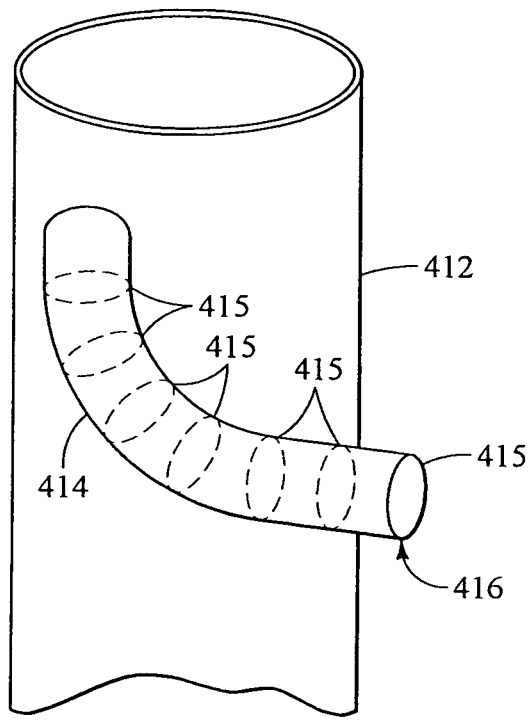
FIG. 16 shows a helical branch having annular stents.
Figure 17:
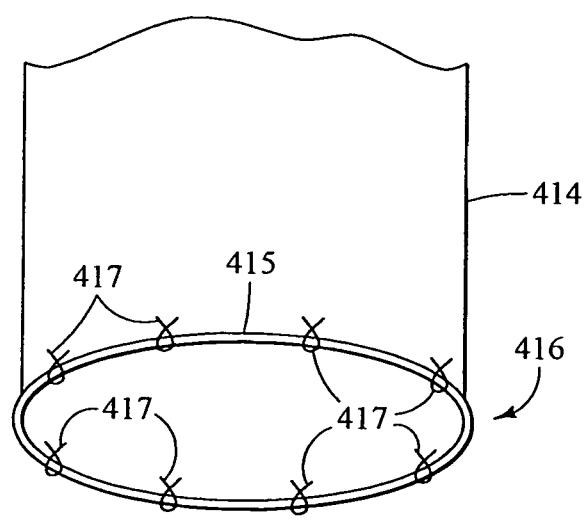
FIG. 17 shows an annular stent sutured to the distal ostium of a helical branch.

It may be preferable to support the prosthetic branch with one or more stents. As shown in FIG. 16, the prosthetic branch 414 has annular stents 415. These stents 415 are preferably made of stainless steel, or nitinol wire or other shape memory metal. Any suitable thickness of wire may be used, preferably of a diameter of about 0.006-0.009 inch. The stents 415 can be either closed loop rings or coils with free ends, and can be attached using sutures or other suitable method. They can be positioned at various intervals from a location near the trunk 412 to the distal ostium 416. FIG. 17 shows an annular stent 415 affixed to the distal ostium 416 of the branch prosthesis 414 using sutures 417.

As shown in FIG. 18, a helical stent 418 can also be used to support the helical branch 414. The helical stent 418 is preferably made from nitinol or other shape memory metal. Any suitable thickness of wire may be used, preferably having an outer diameter of about 0.006-0.009 inch. As shown in FIG. 19, an end of the helical stent 418 can be formed into a closed loop 419 so that it supports the distal ostium 416 of the branch 414. FIG. 20 shows a nitinol coil that is attached to the proximal ostium of the branch 414 to hold the ostium in its operational state.

Figure 21A:
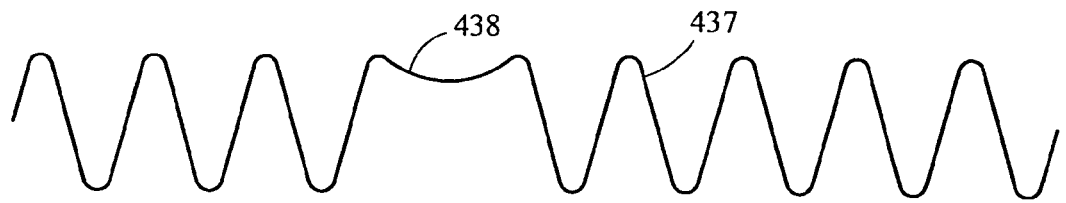
FIGS. 21a-b show two modified Z-stents that may be used to support, without obstructing, the branch-trunk anastomosis.
Figure 21B:
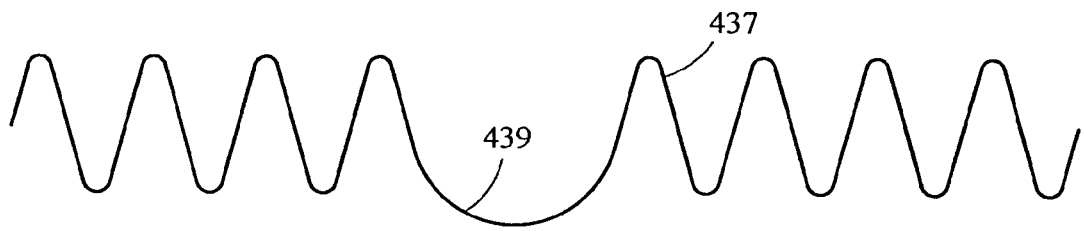

FIGS. 21a-d show two, preferably endless, Z-stents that have two regions: the zigzag region 437 which encircles the tubular graft and a section designed to accommodate and/or support at least a portion of the branch-trunk anastomosis. The stent of FIG. 21a has a section 438 that is shaped to support the proximal aspect of the anastomosis. The stent of FIG. 21b has a section 439 that is shaped to support the distal aspect of the anastomosis. The stents of FIGS. 21a-b are shown working to support a branch-trunk anastomosis in FIG. 22a.

Figure 21C:
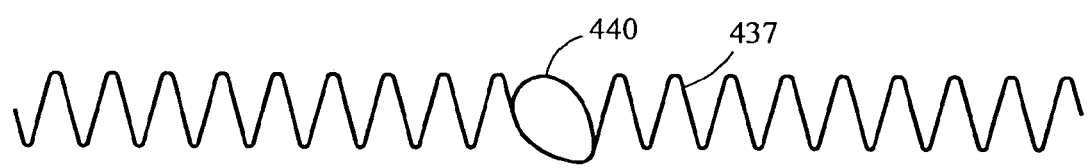
FIG. 21c shows a modified Z-stent that has a loop for supporting the branch trunk anastomosis.
Figure 22A:
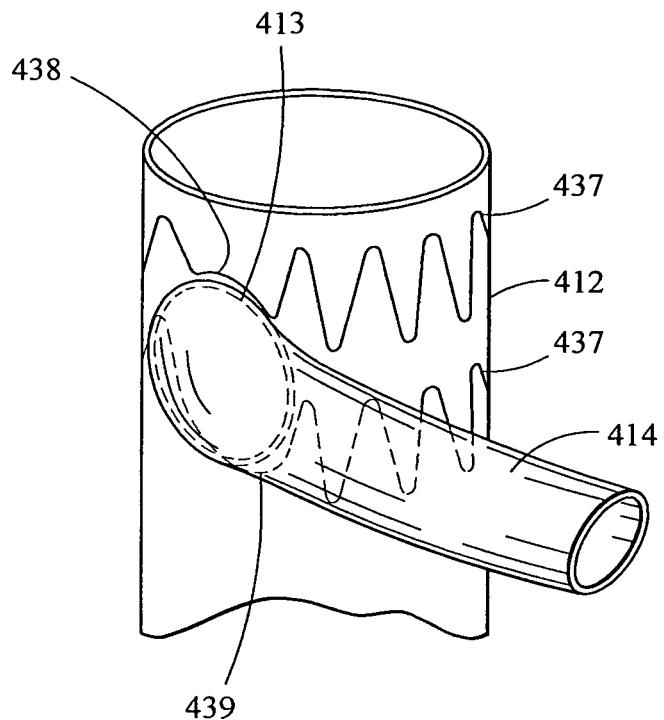
FIG. 22a shows the stents of FIGS. 21a-b attached to a graft and positioned to support a branch-trunk anastomosis.
Figure 22B:
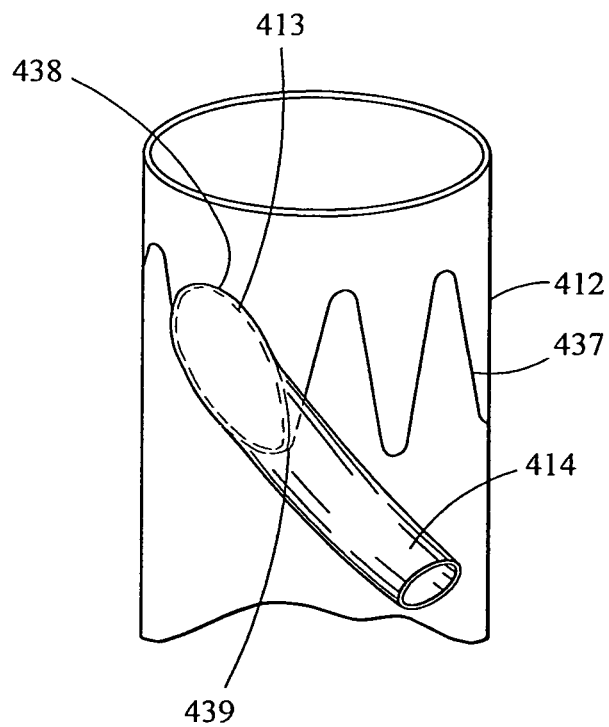
FIG. 22b shows the stent of FIGS. 21c attached to a graft and positioned to support a branch-trunk anastomosis.
Figure 23E:
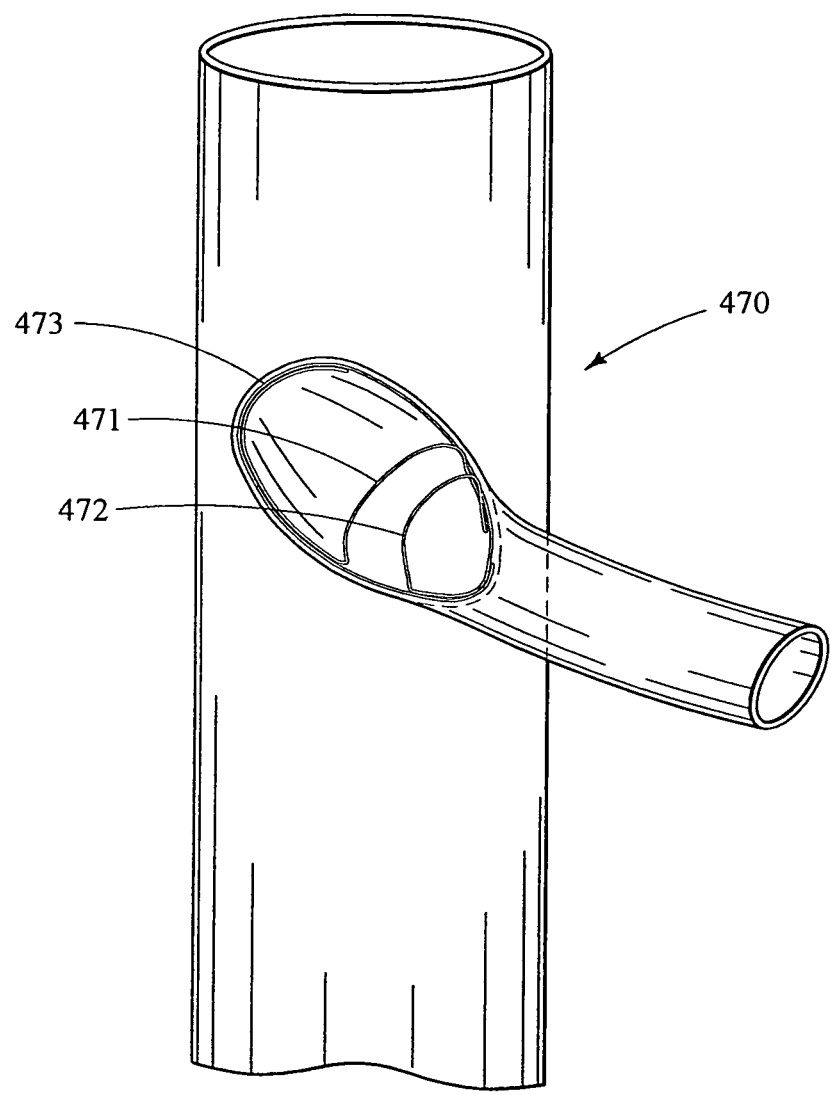
FIGS. 23e-f show the stent of FIGS. 23a-d affixed to the inside of a branch adjacent the branch-trunk anastomosis.
Figure 23F:
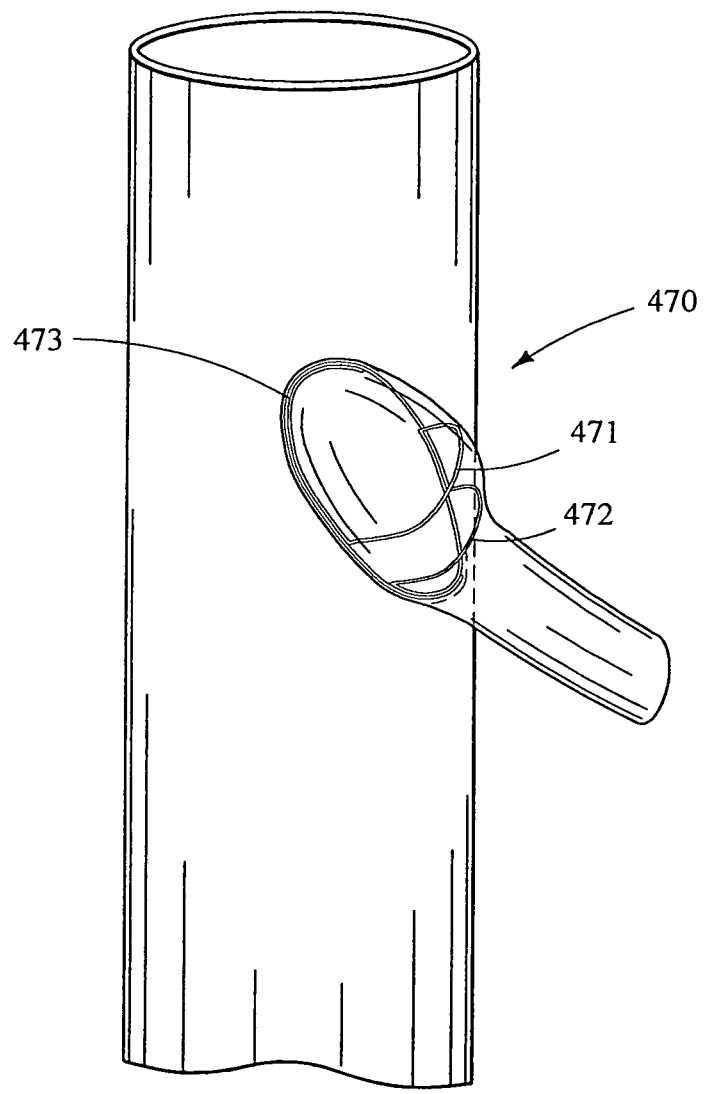

As shown in FIG. 22a, the endless Z-stents are attached to the prosthetic trunk; each stent is curved around one of two different portions of a perimeter of the anastomosis. The stents of FIGS. 21a may also be placed on the distal aspect of the anastomosis, which the stent of FIG. 21b is placed on the proximal aspect of the anastomosis. FIG. 22b shows a stent similar to that shown in FIG. 21c attached to a stent graft.

Figure 21D:
FIG. 21d shows a modified Z-stent that has an asymmetrical bend for supporting the distal aspect of the branch-trunk anastomosis.

FIG. 21c shows a Z-stent 437 that contains a loop 440 that is designed to follow the perimeter of the branch-trunk anastomosis. FIG. 21d has a section 441 that is shaped to support the distal aspect of the anastomosis.

FIGS. 23a-d show a stent that is designed to maintain the shape of the branch-trunk anastomosis. The stent 470 has three main portions, a distal hoop 472, a proximal hoop 471 and an ovoid outer stent perimeter 473. FIG. 23e shows the stent 470 attached internally to a branch-trunk anastomosis. The stent 470 may be attached in any conventional manner, including sutures. The ovoid outer perimeter 473 is preferably sutured to the prosthetic trunk, while the hoops 471, 472 extend away from the perimeter 473 into the prosthetic branch, and is preferably sutured to the prosthetic branch. The stent 470 preferably maintains the shape of the anastomosis.

Figure 24A:
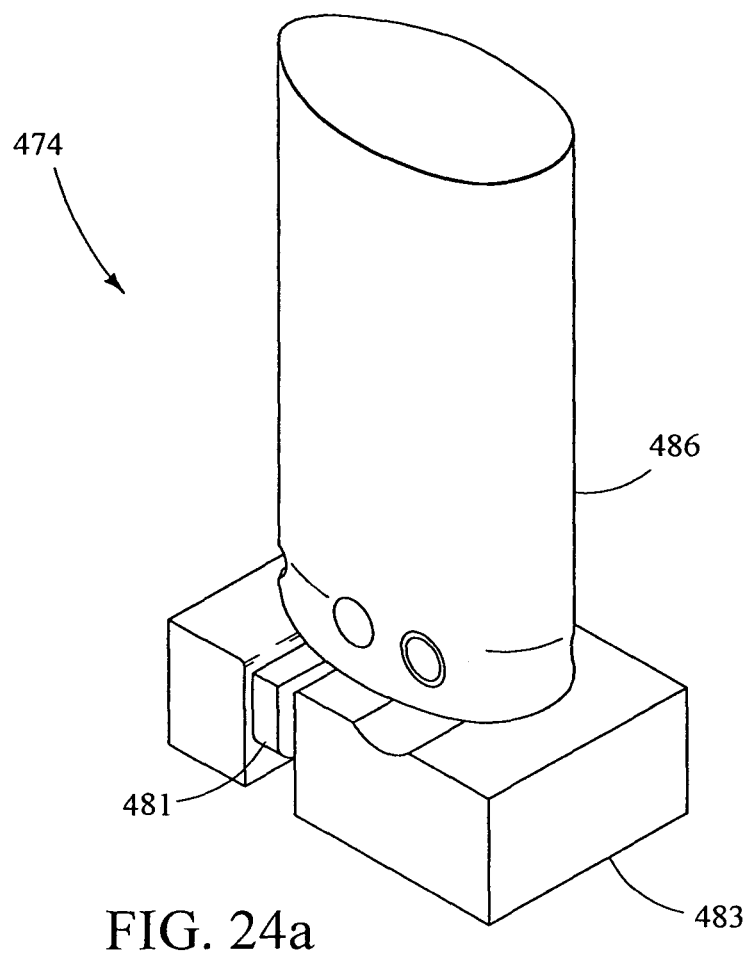
FIG. 24a shows a perspective view of a heat-setting fixture for forming the stent of FIGS. 23a-d.
Figure 24B:
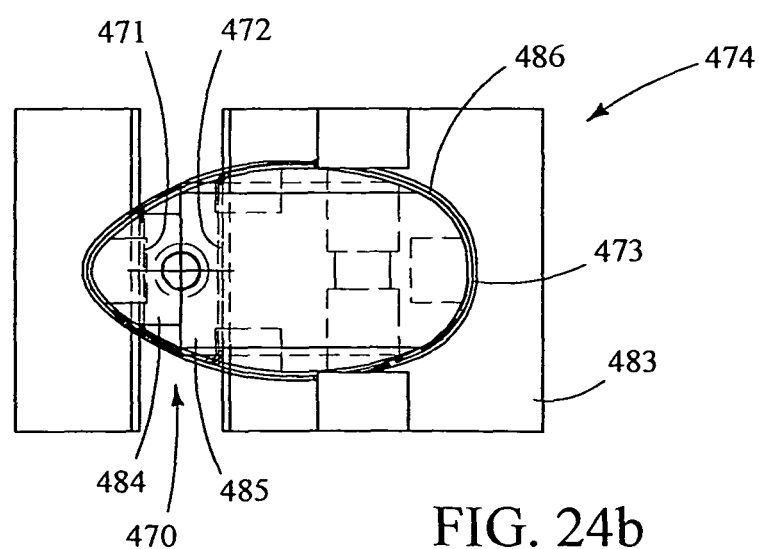
FIG. 24b shows a plan view of a heat-setting fixture for forming the stent of FIGS. 23a-d.
Figure 24C:
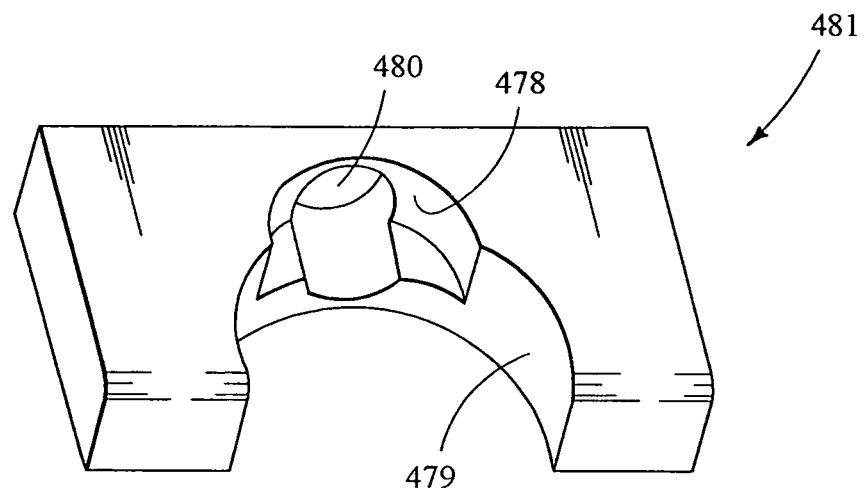
FIG. 24c shows a perspective view of a part of the heat-setting fixture used to form the stent of FIGS. 23a-d.
Figure 24D:
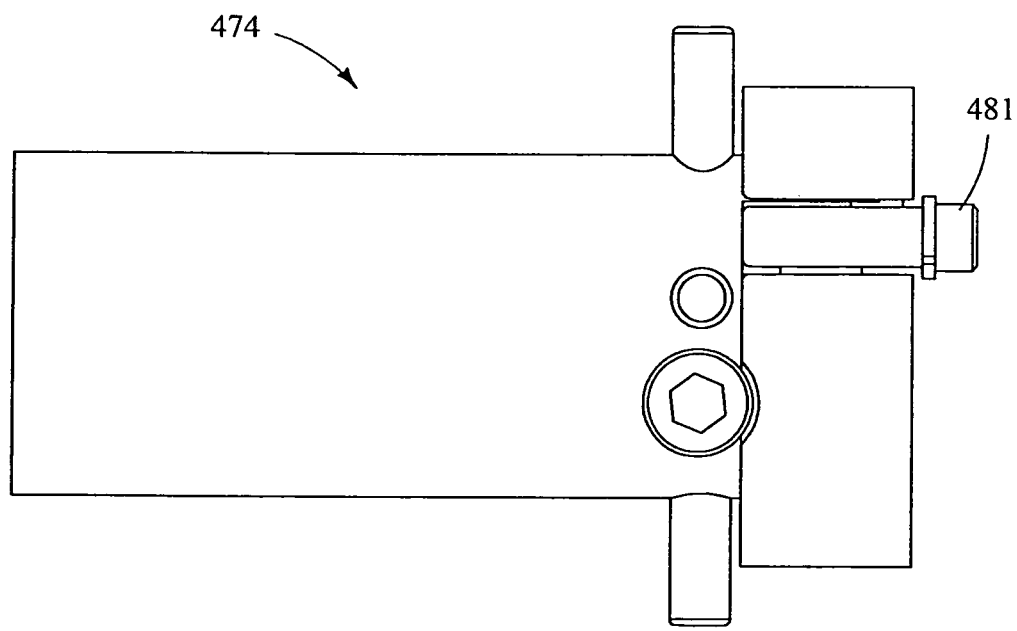
FIG. 24d shows a side view of a heat-setting fixture used to form the stent of FIGS. 23a-d.

The stent of FIGS. 23a-f is preferably made from a single nitinol wire or similar shape-memory metal. To have the wire "remember" the shape depicted in FIGS. 23a-e, the wire is preferably heat-set while in that shape. This can be accomplished through the use of the device 474 of FIGS. 24a-d or a similar heat-setting fixture or mold. A plan view of the fixture 474 is shown in FIG. 24b. The ovoid outer perimeter 473 is formed by wrapping the nitinol wire around the column 486. The distal hoop 472 is formed by looping the wire over the distal arch section 485 of the base 483; the proximal hoop 471 is formed by looping the wire over the proximal arch section 484 of the base 483. The hoops 471, 472 kept in place by the arched surfaces 478, 479 on the fixture cavity 481 when the fixture cavity 481 is attached to the base 483. The base 483 is attached by a screw or bolt that passes through the hole 480 and into the column 486.

Figures 25, 26:
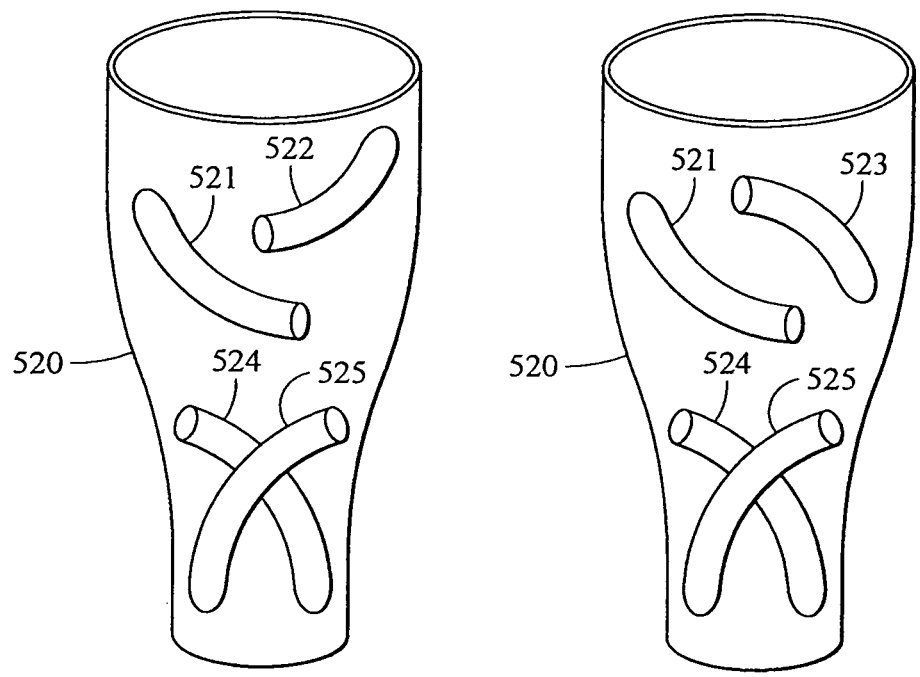
FIGS. 25, 26, and 27a-e show multiple prosthetic branches extending from a prosthetic trunk.

For prosthetic trunks designed for implantation into the aorta, prosthetic branches may be formed to shunt flow into the superior mesenteric, celiac and both renal arteries. There are a variety of possible arrangements and orientations for these multiple branches, as shown in FIGS. 25 through 27. FIG. 25 shows an aortic module 520 having two renal branches 524, 525, both of which shunt flow proximally relative to the prosthetic trunk. In FIG. 25, both the celiac branch 522 and the SMA branch 521 shunt flow distally relative to the prosthetic trunk. As shown in FIG. 26, the celiac branch 523 can be positioned so that it extends proximally.

Figure 27A:
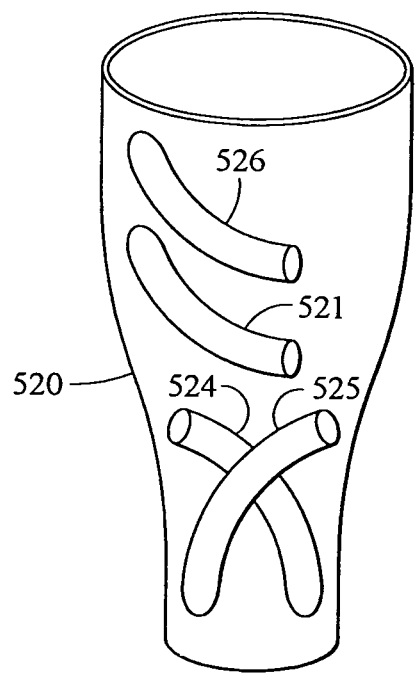
Figure 27B:
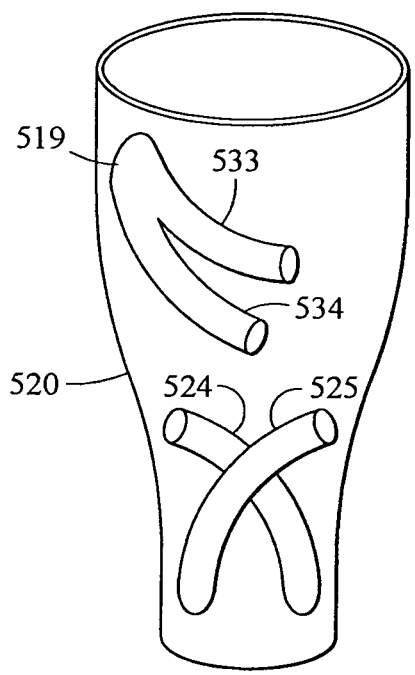
Figure 27C:
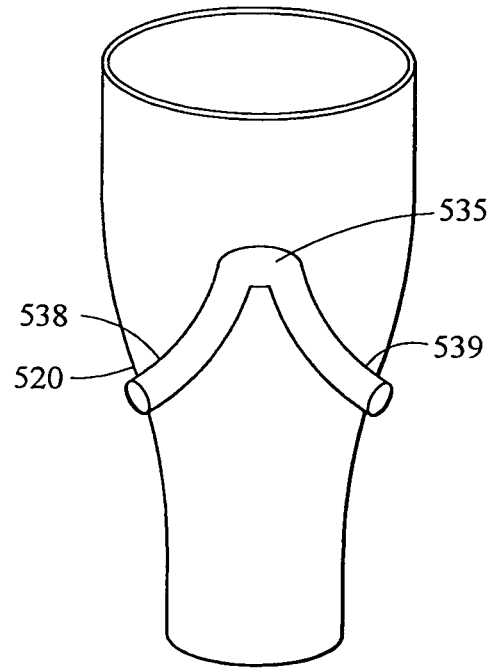

As shown in FIG. 27a, the celiac branch 526 can extend distally from the same side of the trunk 520 as the SMA branch 521. The renal branches can also be positioned so that they extend distally. FIG. 27b has helical renal branches 524, 525 that extend proximally relative to the prosthetic trunk 520. The celiac 533 and SMA 534 branches share a common anastomosis 519 before splitting to their respective vessels. FIG. 27c shows an arrangement for the renal branches 538, 539 having a common anastomosis 535.

Figure 27D:
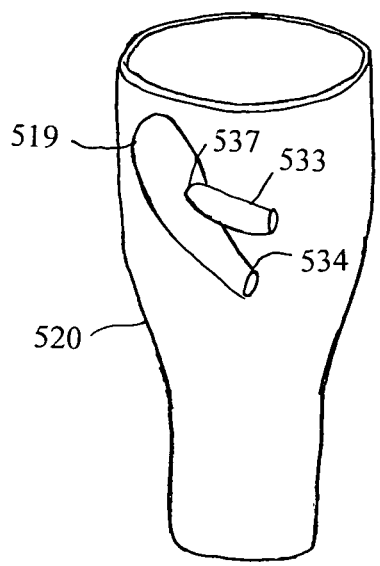

In FIG. 27d, the prosthesis has celiac and SMA branches 533, 534 in fluid communication with the prosthetic trunk 520 through a common anastomosis 519 formed in the wall of the prosthetic trunk. In this example, the celiac branch 533 is in fluid communication with the SMA branch 534 through an anastomosis 537 formed in the wall of the SMA branch. Thus, the celiac branch inlet end is separate, and disposed downstream, from the SMA branch inlet end.

One advantage of decoupling the inlet ends of the branches 533, 534 is that the size of the trunk anastomosis 519 may be reduced. This may reduce the amount of graft material at the anastomosis 519 and the packing density of the graft within the delivery sheath. For example, two prostheses may be constructed, each having celiac and SMA branches 533, 534 that share a common anastomosis 519, as shown in FIG. 27b. In this example, the distal ends of the celiac and SMA branches 533, 534 each have a diameter of 8 mm. In the first graft, the celiac and SMA branches 533, 534 are constructed so that they bifurcate adjacent the anastomosis 519 into branches, each having a diameter of approximately 8 mm. The first graft is constructed with an anastomosis 519 that is large enough to accommodate the size of the inlet ends of both branches 533, 534, for example, approximately 16 mm.

Figure 27E:
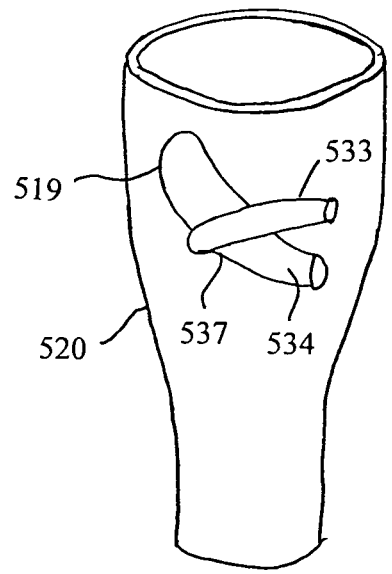

The second graft is constructed with the inlet ends of the branches 533, 534 decoupled as shown, for example, in FIGS. 27d and 27e. The anastomosis 519 need only be large enough to accommodate the inlet end of the SMA branch 534 and, therefore, it may be possible to construct the second graft with a substantially smaller anastomosis 519 without compromising fluid flow. For example, the second graft may have an anastomosis 519 with a diameter of approximately 10 mm. The diameter of the SMA branch 534 may taper along its length, as shown in FIG. 27e.

It should be understood that this example is illustrative, rather than limiting, and that the absolute and relative dimensions of the grafts and components of the grafts can vary. For example, the anastomosis 519 in the first graft described above may have a diameter that is less than or greater than 16 mm. Likewise, the anastomosis 519 in the second graft described above may have a diameter that is less than or greater than 10 mm.

At least one of the branches 533, 534 may be disposed longitudinally along and circumferentially about the trunk 520, as shown in FIGS. 27b and 27d. FIG. 27e shows an example of a prosthesis where the celiac branch 533 is disposed longitudinally along and circumferentially about the SMA branch 534. The size, configuration, and orientation of the branches will be determined based on various considerations, as discussed throughout the specification, such as patient anatomy and promoting laminar flow.

Any of the branches can be oriented so that they extend proximally or distally; similarly, any of the branches can be positioned on either side of the trunk. The arrangements may be chosen in response to patient anatomy, as well as deployment and functional considerations.

Figure 28A:
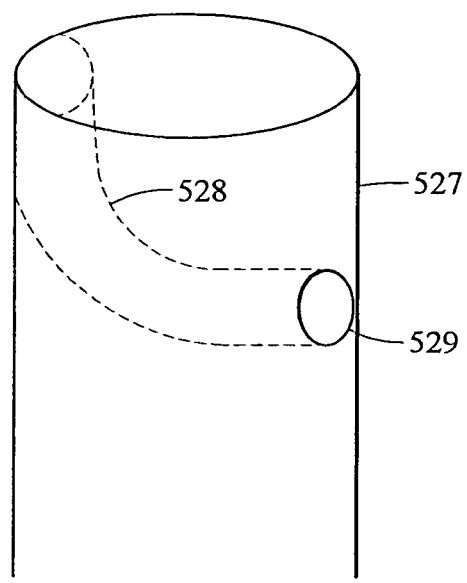
FIGS. 28a-c show an internal helical branch.
Figure 28B:
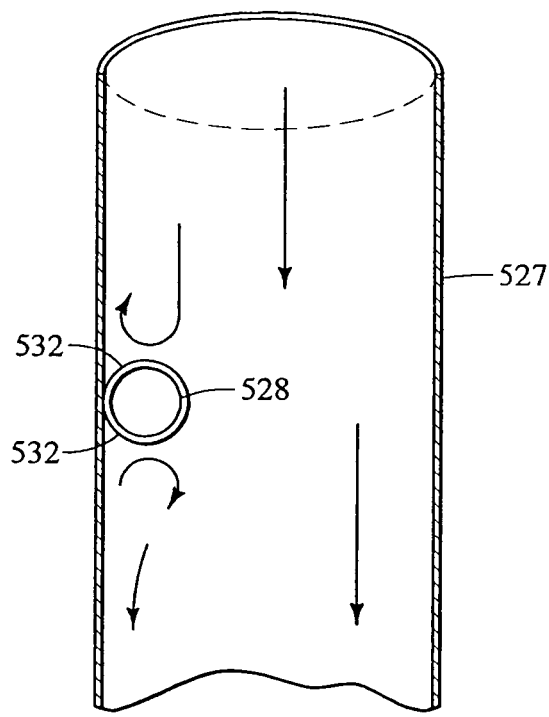
Figure 29:
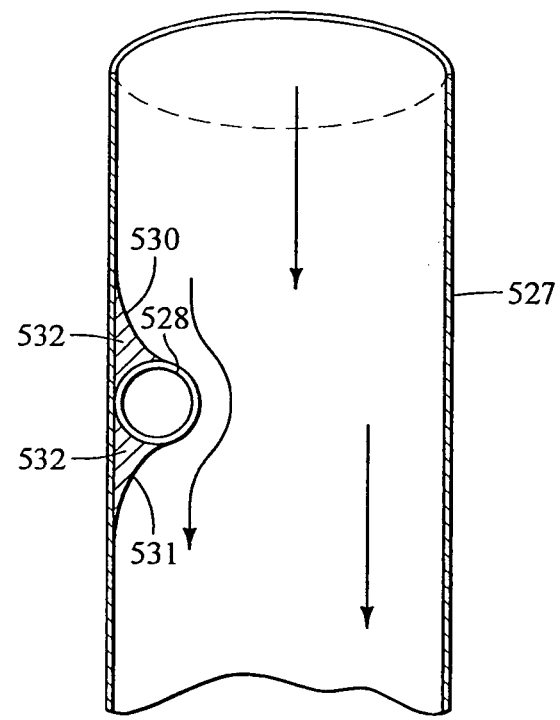
FIG. 29 shows a cross-section of a prosthesis having baffles affixed to an internal helical branch.

FIG. 28a shows an internal helical branch 528, extending circumferentially around and longitudinally about an internal surface of the prosthetic trunk 527, terminating at the distal ostium 529. As shown in FIG. 28b, this approach may cause turbulent flow, especially where the internal branch 528 is at an angle to the blood flow. To improve flow characteristics, the internal branch 528 can be straddled by baffles 530, 531, as shown in FIG. 29. These baffles 530, 531 may be made of any of the materials listed above, and function by filling in or covering the gaps 532 on either side of the branch 528, where it contacts the trunk 527. Baffles preferably act to deflect the flow around portions of the internal helical branch that are at an angle to the direction of blood flow, so that the blood flow is less turbulent.

Figure 28C:
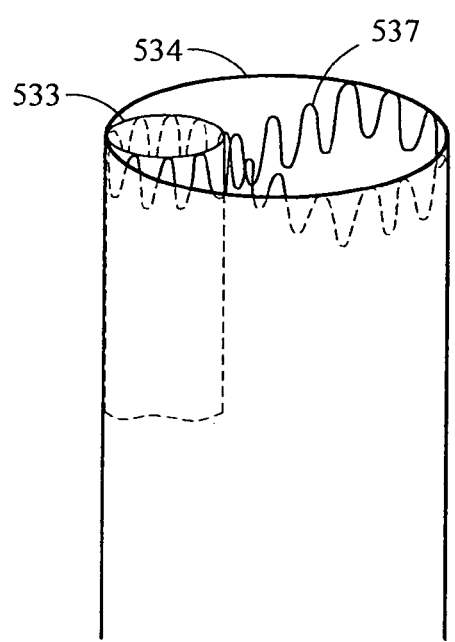
Figure 30:
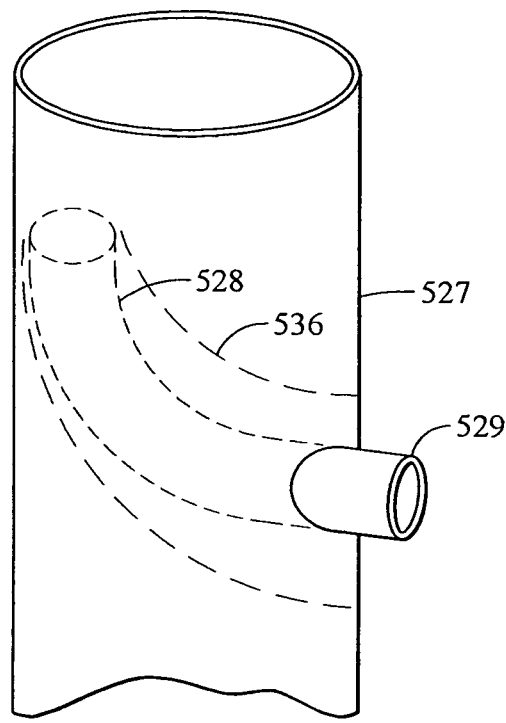
FIG. 30 shows an internal helical branch within a pocket.
Figure 31:
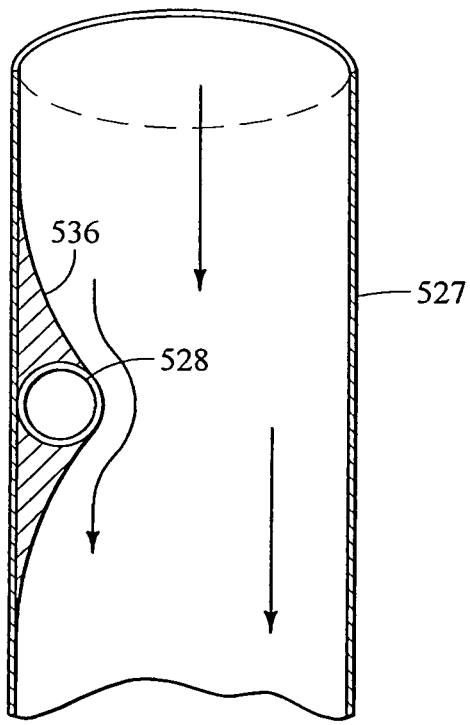
FIG. 31 shows a cross-section of an internal helical branch within a pocket.

Another solution to the turbulent flow around the internal branch 528 is the inclusion of the branch 528 within a pocket 536, as shown in both FIGS. 30 and 31. The cross-section depicted in FIG. 31 shows more laminar flow along the pocket 536 where the internal helical branch runs at an angle to the direction of blood flow. The pocket 536 may be made from woven polyester twill, as described above, or any other suitable material. The internal branch is preferably stented so that it remains patent. The stents may be similar to those stents described and shown in regard to external helical branches. An internal figure-8 Z-stent 535 shown in FIG. 28c may also be used to keep both the branch lumen 533 and the trunk lumen 534 patent. The figure-8 stent 535 is preferably made from a single length of stainless steel wire.

Figure 32A:
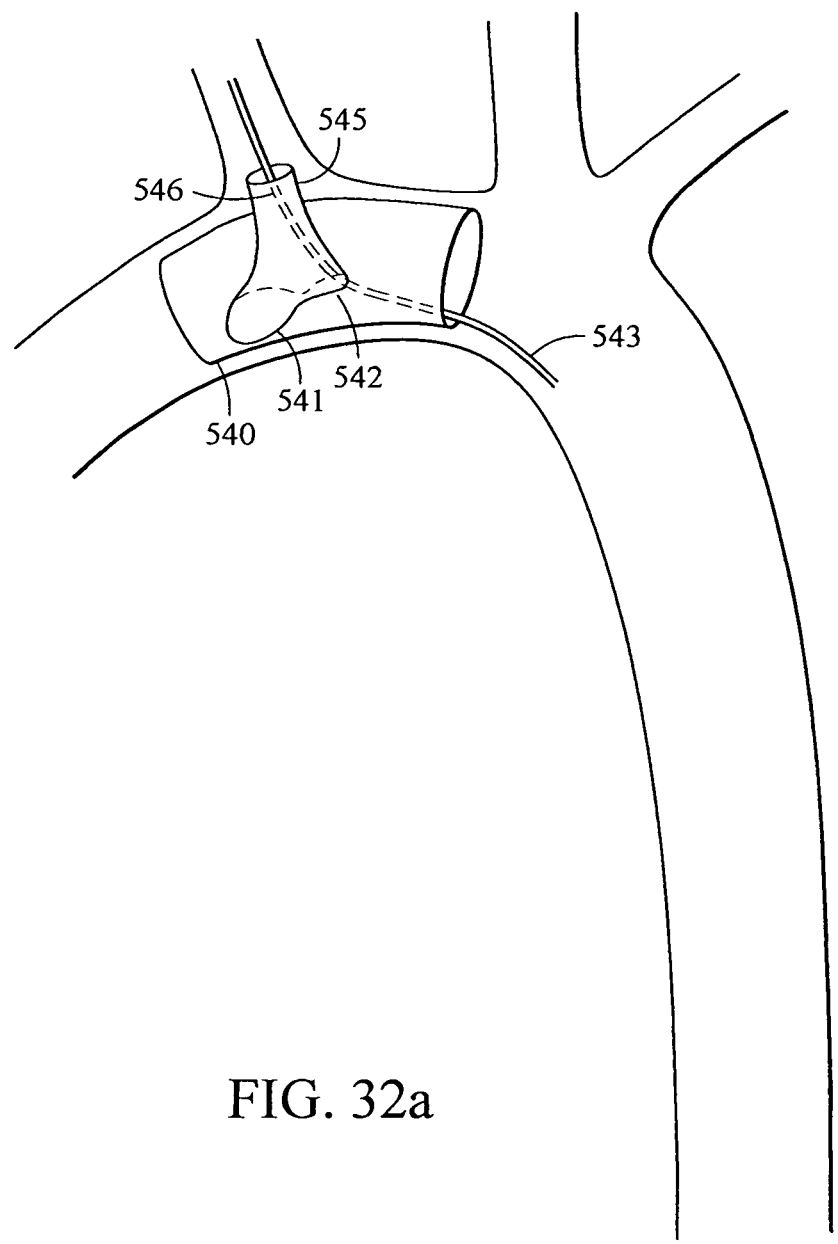
FIGS. 32a-c show thoracic prosthetic modules having one or more helical side branches.

To facilitate deployment of a prosthetic extension module into a prosthetic branch, it may be necessary to have a preloaded wire extend from the inside of the main prosthesis through the prosthetic branch. Depending on the configuration of the prosthetic branch, such a wire may have to bend excessively (i.e., have a small radius bend) as it passes from the main body of the prosthesis into the prosthetic branch. This situation may cause damage to the wire or the prosthesis, or impede deployment. As shown in FIG. 32a, an enlarged anastomosis 541 between the prosthetic trunk 540 and prosthetic branch 545 may enable the deployment wire 543 to have a bend of a larger radius.

An enlarged anastomosis 541 of this type may be especially important in the side branch vessels of the aortic arch, including the left subclavian, left common carotid and innominate arteries. A helical branch 545 extending into the innominate artery, which has a tail section to accommodate the guide wire, is shown in FIG. 32a. The size of the anastomosis 541 may be measured relative to the radius of the prosthetic branch 545. The radius of the anastomosis 541 may be twice that (or more) of the average radius of the prosthetic branch 545 or the distal ostium 546 of the branch 545. The anastomosis 541 shown in FIG. 32a is enlarged by the addition of a tail section 542 through which the wire 543 can travel, which also increases the radius of the turn. An anastomosis with a tail section will be understood as being an anastomosis that has both a wide section and a narrow section, the narrow section being the tail. The thoracic aortic stent graft of FIG. 32a may also extend further into the abdominal aorta, having some of the branches and/or fenestrations described elsewhere in this application. The tailed anastomosis can also be used to increase the guidewire's turn radius in Y-shaped side branches.

Figure 32B:
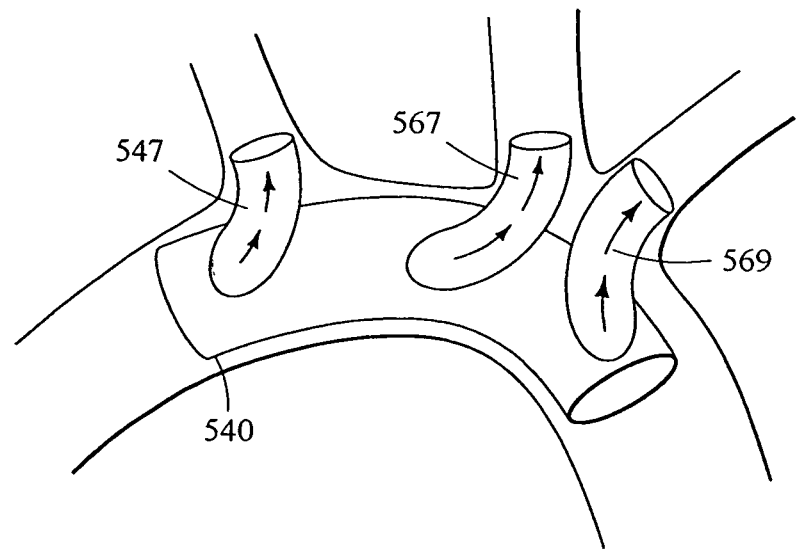
Figure 32C:
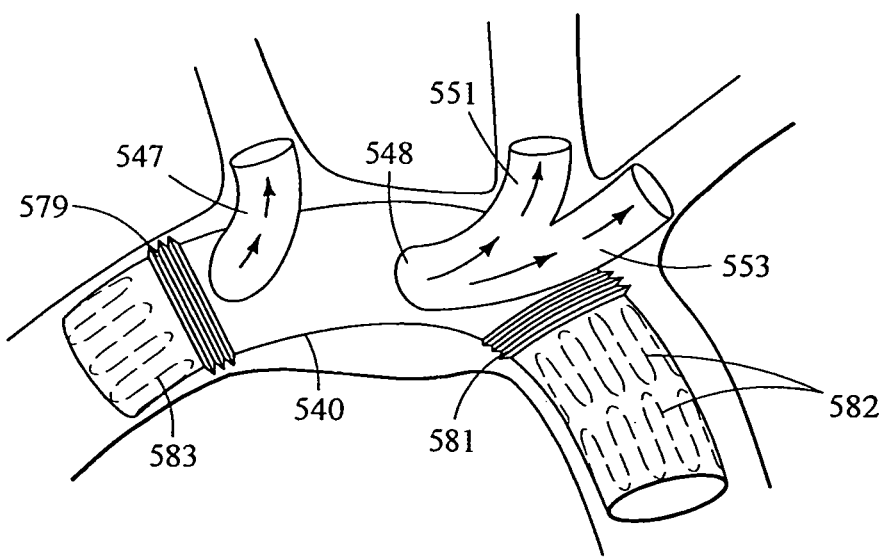

FIGS. 32b and c show various arrangements for the thoracic side branches that extend from the prosthetic trunk 540. The enlarged anastomosis shown in FIG. 32a may also be used in the thoracic prosthetic branches shown in FIGS. 32b and c. In FIG. 32b, there are separate helical side branches 547, 567, 569 for the innominate, left common carotid, and left subclavian, respectively. The arch grafts are preferably curved to accommodate the curve of the aortic arch. FIG. 32c shows the left common carotid prosthetic branch 551 and left subclavian prosthetic branch 553 having a common anastomosis 548. Any of the branches shown in FIGS. 32a-c may be selectively replaced by fenestrations.

FIG. 32c has proximal strain relief crimps 579 and distal strain relief crimps 581 in the prosthetic trunk 540. These are selectively placed on the ends of the prosthetic trunk 540 to provide some strain relief as the thoracic aorta undergoes axial compression and extension under the influence of pulsatile flow. The crimps 579, 581 allow the graft to more easily lengthen, shorten and bend in tandem with the thoracic aorta. The distal 582 and proximal 583 stents improve sealing at the ends of the trunk 540, and may also have barbs (not shown) to enhance fixation.

Blood flow to the various branch vessels of the aorta or other vessel may be accommodated through use of any combination of fenestrations and prosthetic branches, including the integral helical branches described above. One such combination is shown in FIGS. 33 through 40. FIGS. 33 through 40 show various views of an endoluminal prosthesis 549 that has a helical prosthetic branch 552 for shunting flow to one of the renal arteries, a contralateral renal fenestration 558 (an aperture in the wall of the prosthesis that allows blood to flow to one of the renal arteries) and a superior mesenteric artery fenestration 556 (an aperture in the wall of the prosthesis that allows blood to flow to the SMA). A flareable covered or uncovered stent may be deployed into either or both fenestrations 556, 558 in the manner described in U.S. patent application Ser. Nos. 10/984,040; 10/984,416; 10/984,417; 10/984,131; 10/984,520; and 10/984,167, all of which were filed on Nov. 8, 2004 and all of which are incorporated herein by reference.

Figure 33:
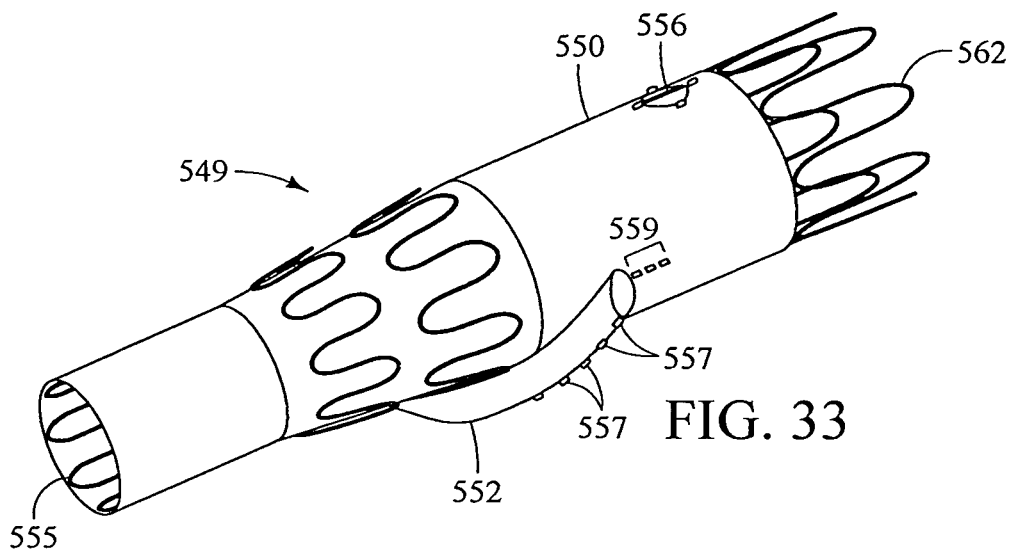
FIGS. 33-36 show various perspective views of a prosthesis having a branch and fenestrations.

FIG. 33 shows the helical branch 552 extending proximally along a tapered prosthetic trunk 550 relative to the prosthetic trunk 550, i.e., away from the distal end 555 of the prosthesis 549. As shown, the helical branch 552 has a pitch (or skew) of about 44° relative to the longitudinal axis of the prosthetic trunk 550 and is preferably attached with six evenly space sutures. The branch 552 is preferably not stretched or compressed when sutured to the trunk 550. Radiopaque markers 557, 559 are attached to both the trunk 550 and the branch 552. The radiopaque markers 559 on the trunk 550 are preferably aligned with the longitudinal axis of the trunk 550. A suprarenal stent 562 is located at the proximal end 562 of the prosthesis 549; this stent is preferably a Z-stent having a diameter of 32 mm, a height of 25 mm and a period of 10. The SMA fenestration 556 is visible in FIG. 33. A fenestration may also be provided for the celiac artery in addition to or instead of the SMA fenestration. The helical branch 552 is preferably crimped (not shown) to help resist kinking.

Figure 34:
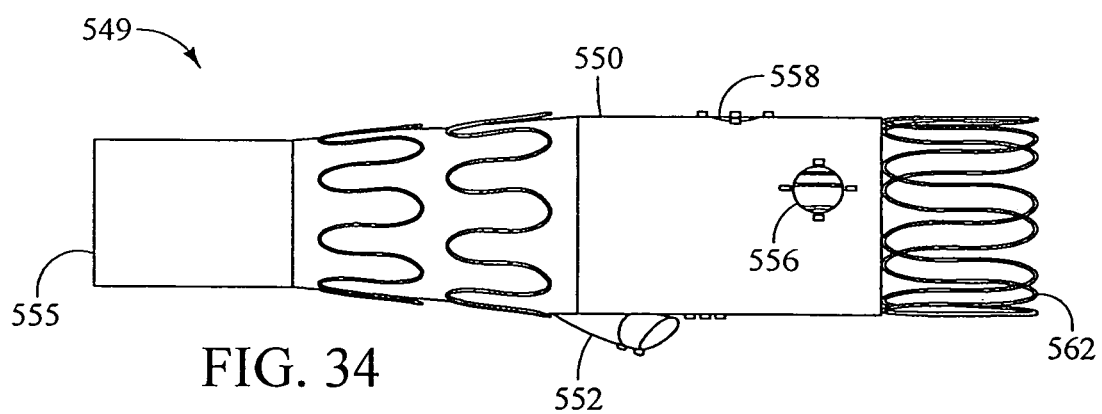
Figure 35:
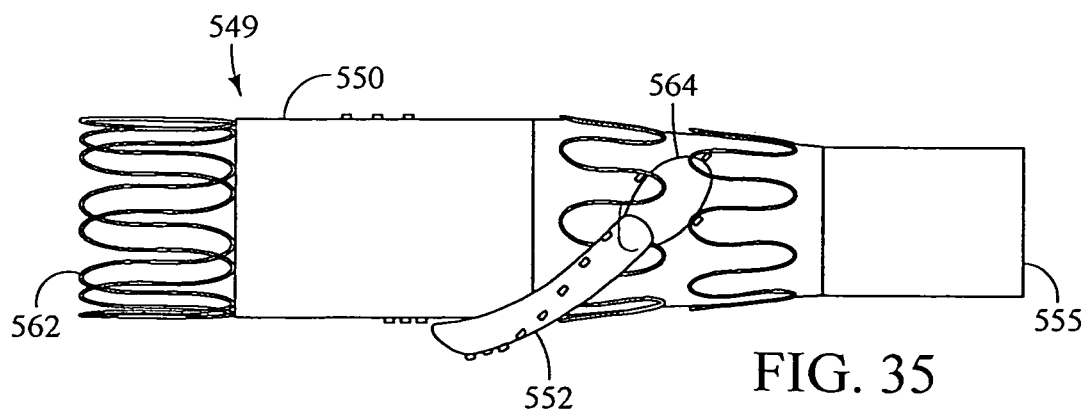
Figure 36:
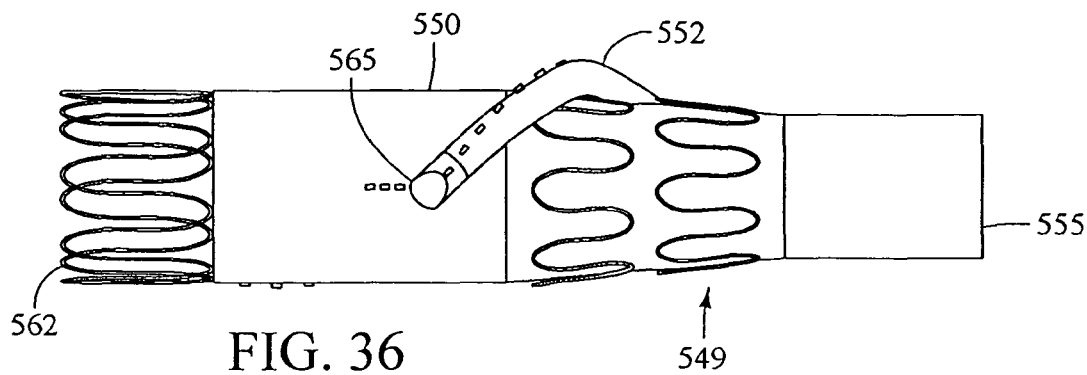

FIGS. 34 through 36 show the same device in different rotations. FIG. 34 shows the relative orientation of the renal fenestration 558 and the SMA fenestration 556. The relative orientation of the branch and the fenestrations can be modified to suit a particular patient's anatomy. FIG. 35 shows the enlarged anastomosis 564 between the branch 552 and the trunk 550. FIG. 36 shows the beveled ostium 565 of the branch 552.

Figure 37:
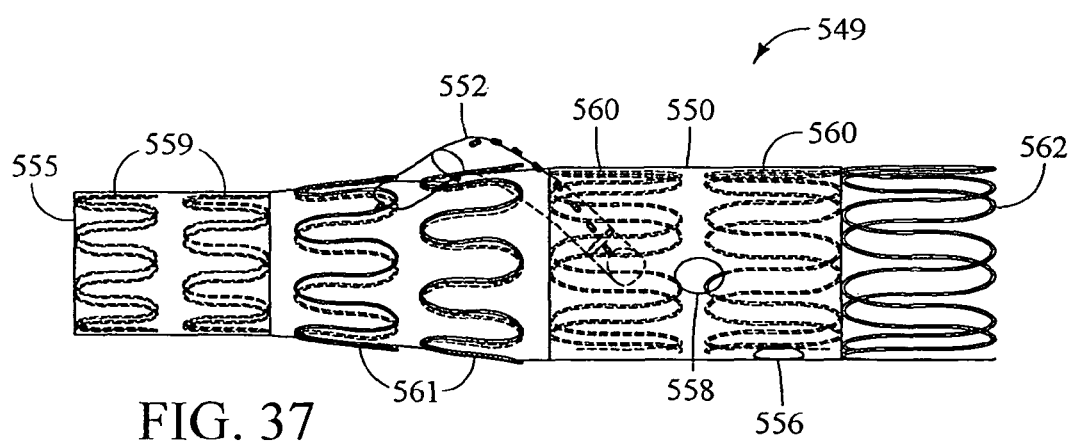
FIGS. 37 and 38 show skeletal views of the prosthesis of FIGS. 29-32.
Figure 38:
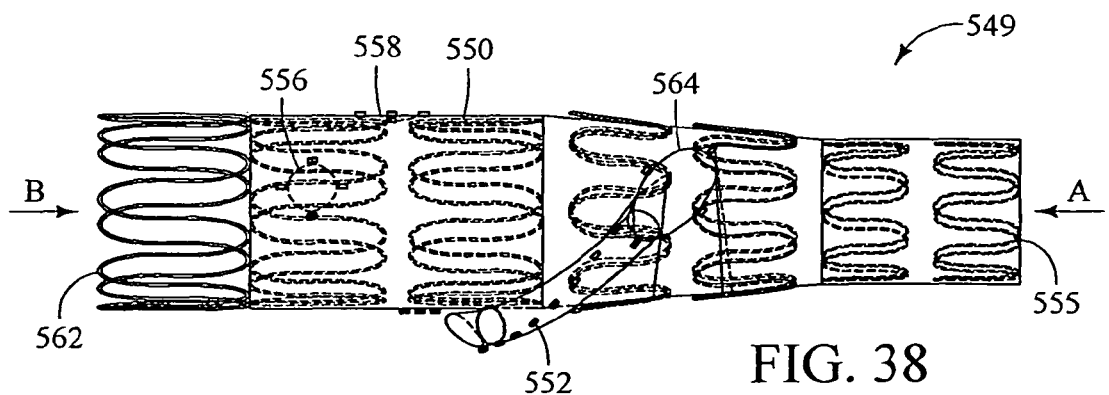
Figure 39:
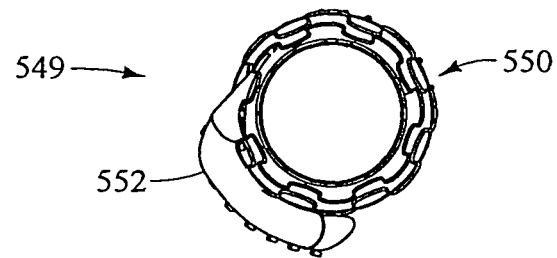
FIG. 39 shows a view of the prosthesis in the direction of arrow A of FIG. 38.
Figure 40:
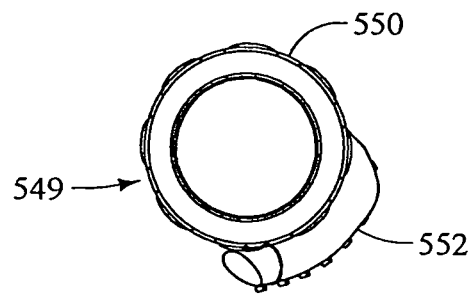
FIG. 40 shows a view of the prosthesis in the direction of arrow B of FIG. 38.

FIGS. 37 and 38 show skeletal views of the device depicted in FIGS. 33 through 36; the distal internal stents 559 and proximal internal stents 560 are visible in these figures. The distal internal stents 559 are preferably Z-stents having a diameter of 24 mm, a height of 14 mm and a period 10. The proximal internal stents 560 are preferably Z-stents having a diameter of 32 mm, a height of 22 mm and a period of 12. The outer stents 561 are preferably Z-stents having dual amplitude, a diameter of 32 mm, a height of 17 mm at a period of 11, and a height of 8.5 mm at a period of 22; these stents 561 are preferably made of nitinol wire having an outer diameter of about 0.330 mm. Any of these dimensions can be tailored to a particular patient's anatomy. FIG. 39 shows a view in the direction of arrow "A" shown in FIG. 38; FIG. 40 shows a view in the direction of arrow "B" shown in FIG. 38.

FIGS. 41a-d show different views of a stent graft 600 having a helical prosthetic branch 614 and three fenestrations: a left renal fenestration 606, a right renal fenestration 636 and an auxiliary fenestration 604. The helical branch 614 feeds the SMA and extends longitudinally and circumferentially from the enlarged anastomosis 622. The proximal end 630 of the stent graft 600 also has a scallop 630 to accommodate the celiac artery. By combining one or more fenestrations with one or more helical branches, flow to one or more of the branch vessels may be preserved while optimizing the deployment characteristics of the stent graft system and packing profile of the stent graft within the deployment sheath.

Figure 41A:
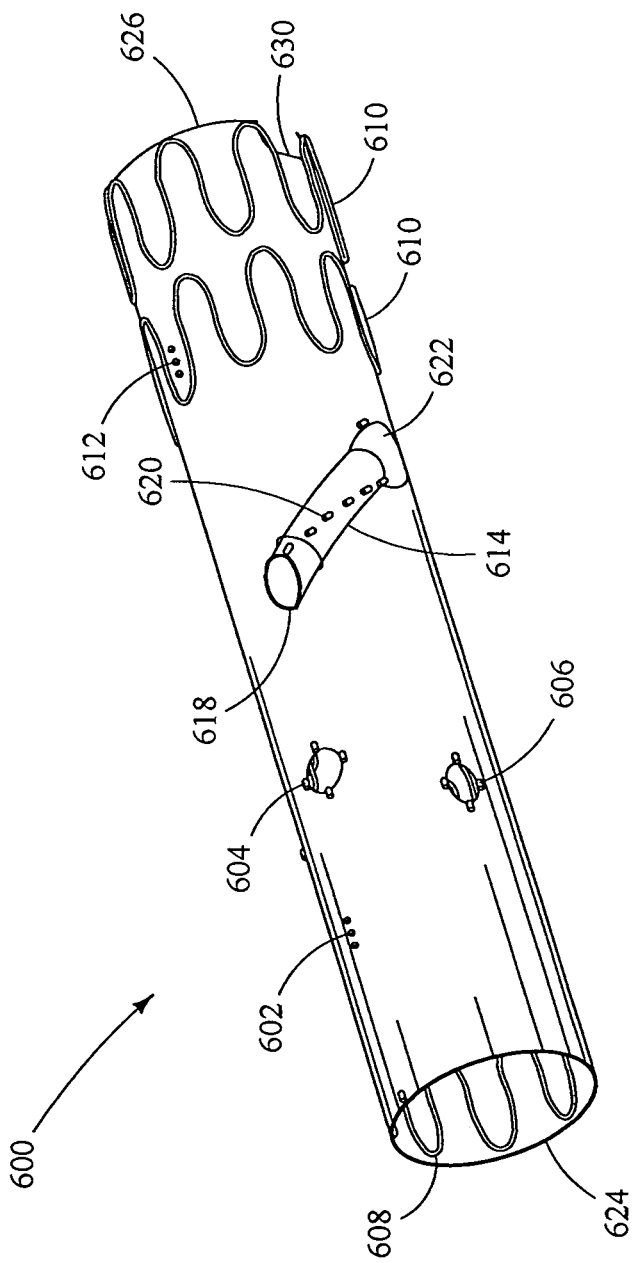
FIGS. 41a-d show various perspective views of an aortic prosthesis having a branch and fenestrations.
Figure 41C:
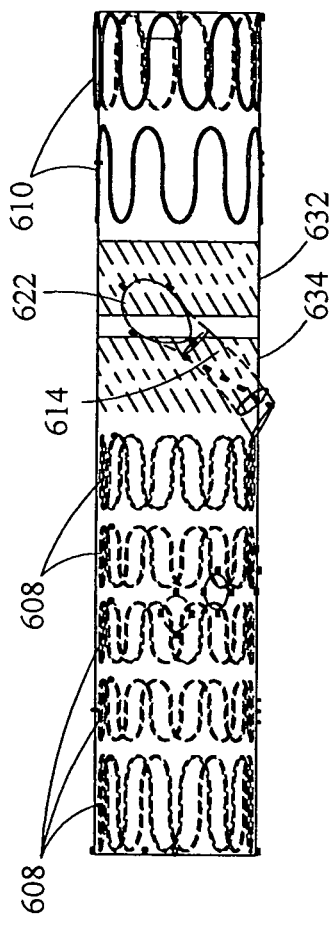
Figure 41B:
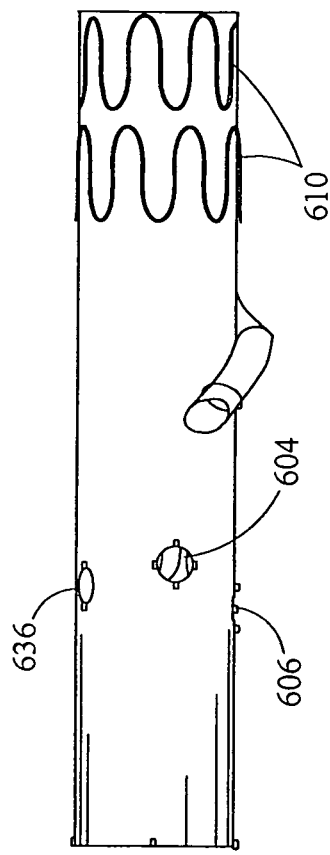
Figure 41D:
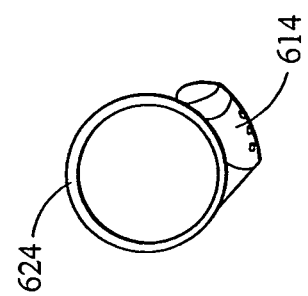
Figure 42A:
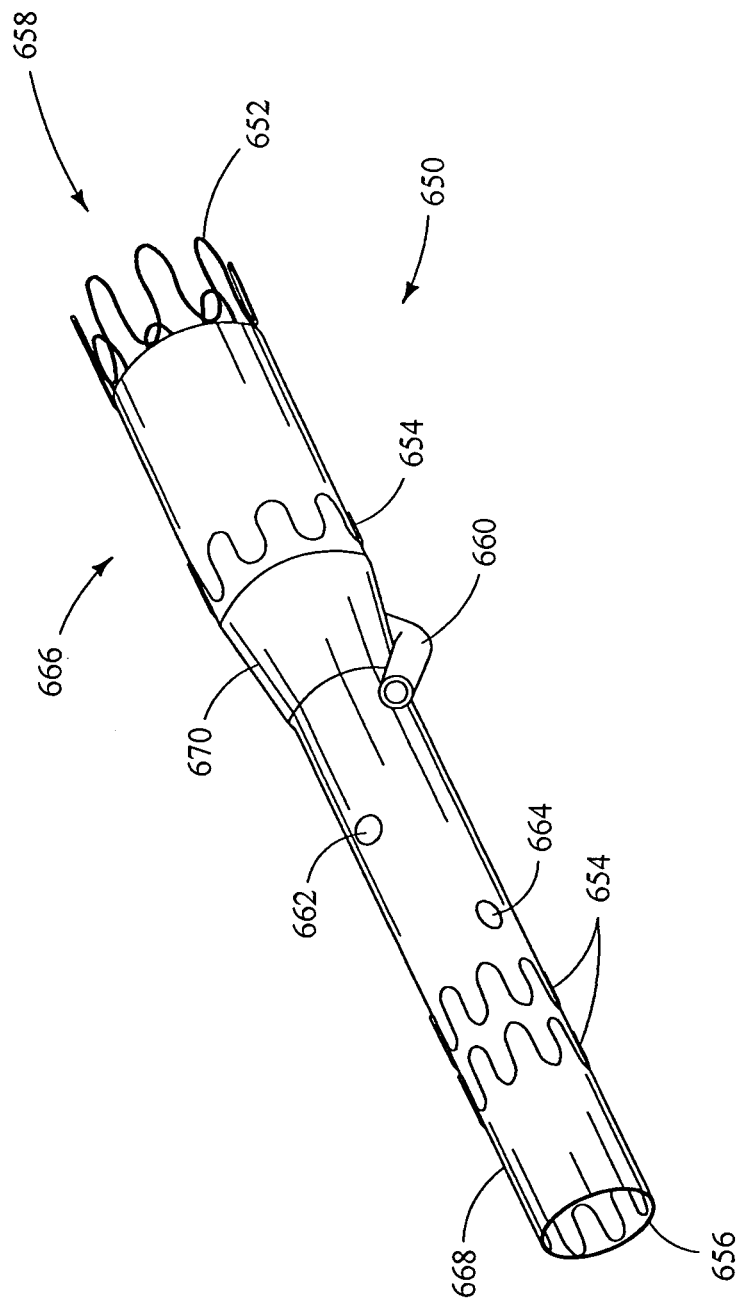
FIGS. 42a-d show various perspective views of an aortic prosthesis having a branch and fenestrations.
Figure 42B:
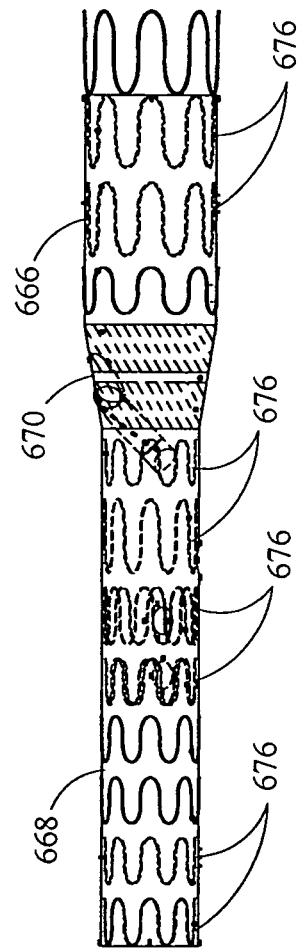
Figure 42C:
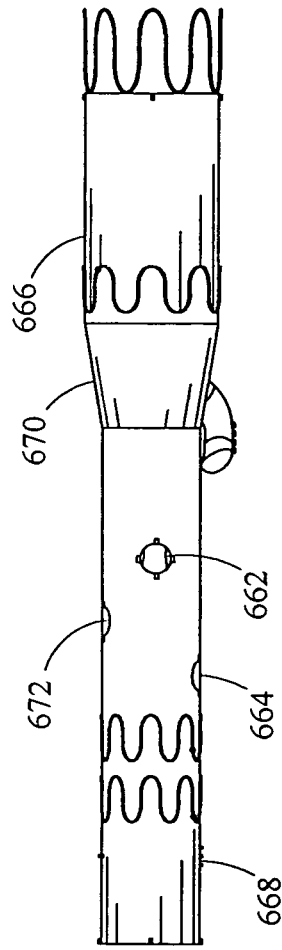
Figure 42D:

Radiopaque markers 602, 612 near the proximal 626 and distal 624 ends of the stent graft 600 help the surgeon identify the rotation of the stent graft 600 during deployment, as do the markers 620 on the helical branch 614. The helical branch 614 may have a beveled distal anastomosis 618. The stent graft 600 is supported by both externally placed stents 610 near the proximal end 626 of the stent graft 600 and internally placed stents 608. As shown in FIG. 41c, regions 632, 634 near the anastomosis 622 may be occupied by stents of any shape, preferably those designed to avoid obstructing and support the anastomosis 622, such as those of FIGS. 21a-d. FIG. 41d shows an axial view of the stent graft 600 from the distal end 624.

FIGS. 42a-d show another stent graft 650 that has both fenestrations and a helical branch graft. This stent graft 650 has a taper 670 in the middle such that the diameter is smaller at the distal end 656 and through the distal section 668 than at its proximal end 658 and through its proximal section 666. There are three fenestrations in the graft, an SMA fenestration 662, a left renal fenestration 664, and a right renal fenestration 672. The helical branch 660 provides flow to the celiac artery. The stent graft 650 is supported by external Z-stents 654 and internal Z-stents 676. The taper 670 may by supported by stents of any shape, preferably those designed to avoid obstructing the branch-trunk anastomosis 670, such as those of FIGS. 21a-d. There is an uncovered proximal stent 652 which preferably has barbs (not shown) extending from it to enhance fixation.

Since arterial anatomy and aneurysm topology vary between patients, any of the prosthesis designs described above is preferably modified to accommodate a particular patient's need. The first step is to review the patient's CT scans. The critical parameters for prosthesis design (deployment site, proximal and distal sealing points) for the device needed for each patient are defined. A three-dimensional (3-D) model of the aneurysm is created using techniques known to one of skill in the art.

The aneurysm model can be incorporated into Solid Works™ or other suitable solid and surface modeling software. With this software a 3-D endoluminal prosthesis can be designed based on the aneurysm model and the defined critical parameters. A mechanical drawing is developed from the 3-D device. The mechanical drawing specifications are then used to create the component materials for the prototype prosthesis, including the prosthesis fabric and stents. Then the material and stents are assembled to form the final prosthesis.

A Modular Prosthesis and Introducer

Modular prostheses are known for use in treating descending thoracic and abdominal aortic aneurysms, where the prosthesis at the proximal end defines a single lumen for placement within the aorta and at the other end is bifurcated for extension into the iliac arteries. Iliac extension prosthetic modules can be connected to the ends of the bifurcation. A schematic view of such a prosthesis is described in further detail in PCT application WO98/53761.

WO98/53761 discloses a prosthesis which includes a sleeve or tube of biocompatible prosthesis material such as polyester fabric or polytetrafluoroethylene (PTFE) defining a single-lumen portion and a bifurcation, and further includes several stents secured therealong. The prosthesis is designed to span an aneurysm that extends along the aorta proximally from the two iliac arteries. This reference also discloses the manner of deploying the stent prosthesis in the patient utilizing an introducer assembly.

In the WO98/53761 application, the material-covered portion of the single-lumen proximal end of the prosthesis bears against the wall of the aorta above the aneurysm to seal the aneurysm at a location that is spaced distally of the entrances to the renal arteries. Thin wire struts of a proximal attachment stent traverse the renal artery entrances without occluding them, while anchoring the prosthesis in position within the aorta.

An extension module is affixed to one of the legs of the prosthesis to extend along a respective iliac artery and, optionally, extensions may be affixed to both legs. These extension modules are attached by tromboning. The deployment of a modular endoluminal prosthesis into the lumen of a patient from a remote location by the use of a deployment device or introducer is disclosed in the same patent application. PCT application WO98/53761 is incorporated herein by reference.

One modular prosthesis similar to that described in WO98/53761, the Zenith® AM Endovascular Graft sold by Cook Incorporated, has been approved by the Food and Drug Administration (FDA) to treat aortic aneurysms. The Zenith® AAA Endovascular Graft is made up of three prosthetic modules: a main body module and two leg modules. The main body is positioned in the aorta. The legs are positioned in the iliac arteries and connect to the main body. The prosthesis thus extends from the aorta below the renal arteries into both iliac arteries. The prosthesis itself is made of a polyester material like that used in open surgical repair. Standard surgical suturing techniques are used to sew the graft material to a frame of stainless steel stents. These self-expanding stents provide support for the graft material.

Figure 43:
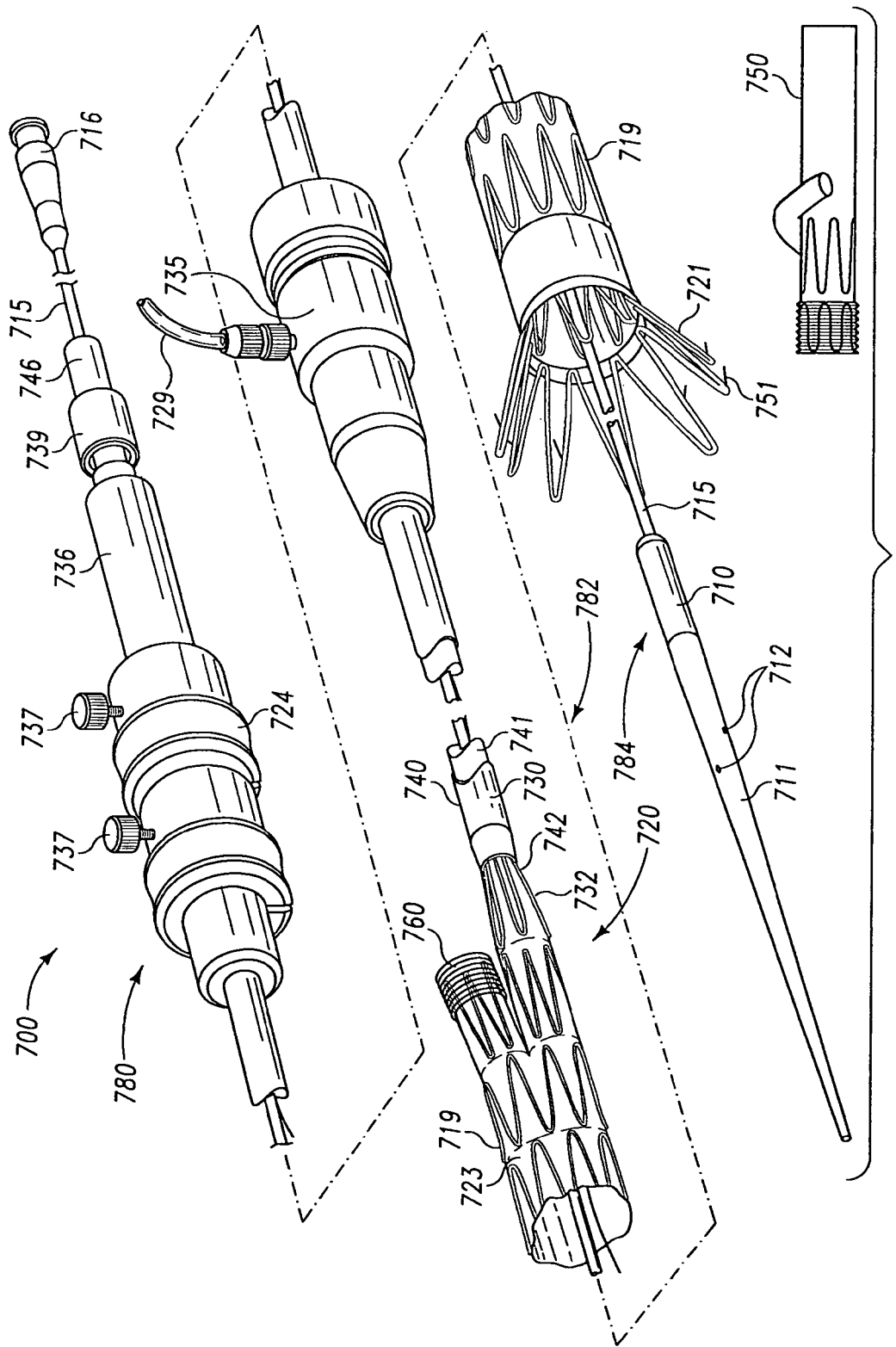
FIG. 43 shows an apparatus for deploying a bifurcated prosthesis.

FIG. 43 shows a Zenith® self-expanding bifurcated prosthesis 720 (product code TFB1 through TFB5, available from Cook Incorporated, Bloomington, Ind.), and an endovascular deployment system 700, also known as an introducer 700, for deploying the prosthesis 720 in a lumen of a patient during a medical procedure. These items are each described in greater detail in PCT application WO98/53761. A self-expanding branched prosthesis 750 similar to that described in reference to FIG. 13b is also shown.

The bifurcated prosthesis 720 has a generally inverted Y-shaped configuration. The prosthesis 720 includes a body 723, a shorter leg 760 and a longer leg 732. The bifurcated prosthesis 720 comprises a tubular graft material, such as polyester, with self-expanding stents 719 attached thereto. The self-expanding stents 719 cause the prosthesis 720 to expand following its release from the introducer 700. The prosthesis 720 also includes a self-expanding Z-stent 721 that extends from its proximal end. The self-expanding Z-stent 721 has distally extending barbs 751. When it is released from the introducer 700, the self-expanding Z-stent 721 anchors the barbs 751, and thus the proximal end of the prosthesis 720, to the lumen of the patient. As an alternative to the prosthesis 720 shown in FIG. 43, a prosthesis such as that shown in FIG. 6 could be deployed followed by renal branch extensions; this would have the added benefit of excluding any aneurysmal tissue in the renal arteries and allowing the aortic graft to extend further proximally. The self-expanding branched prosthesis 750 is similar to the branched prosthesis described in reference to FIG. 13b and is configured to form a tromboning connection with the shorter leg 760 of the bifurcated prosthesis 720 and with a branch extension. A notch or scallop may be cut into the proximal end of the branched prosthesis 750 to facilitate deployment of the module.

The introducer 700 includes an external manipulation section 780, a distal attachment region 782 and a proximal attachment region 784. The distal attachment region 782 and the proximal attachment region 784 secure the distal and proximal ends of the prosthesis 720, respectively. During the medical procedure to deploy the prosthesis 720, the distal and proximal attachment regions 782 and 784 will travel through the lumen to a desired deployment site. The external manipulation section 780, which is acted upon by a user to manipulate the introducer, remains outside of the patient throughout the procedure.

The proximal attachment region 784 of the introducer 700 includes a cylindrical sleeve 710. The cylindrical sleeve 710 has a long tapered flexible extension 711 extending from its proximal end. The flexible extension 711 has an internal longitudinal aperture (not shown). This longitudinal aperture facilitates advancement of the tapered flexible extension 711 along an insertion wire (not shown). The longitudinal aperture also provides a channel for the introduction of medical reagents. For example, it may be desirable to supply a contrast agent to allow angiography to be performed during placement and deployment phases of the medical procedure.

A thin walled metal tube 715 is fastened to the extension 711. The thin walled metal tube 715 is flexible so that the introducer 700 can be advanced along a relatively tortuous vessel, such as a femoral artery, and so that the distal attachment region 782 can be longitudinally and rotationally manipulated. The thin walled metal tube 715 extends through the introducer 700 to the manipulation section 780, terminating at a connection means 716.

The connection means 716 is adapted to accept a syringe to facilitate the introduction of reagents into the thin walled metal tube 715. The thin walled metal tube 715 is in fluid communication with the apertures 712 of the flexible extension 711. Therefore, reagents introduced into connection means 716 will flow to and emanate from the apertures 712.

A plastic tube 741 is coaxial with and radially outside of the thin walled metal tube 715. The plastic tube 741 is "thick walled"—its wall is preferably several times thicker than that of the thin walled metal tube 715. A sheath 730 is coaxial with and radially outside of the plastic tube 741. The thick walled plastic tube 741 and the sheath 730 extend distally to the manipulation region 780.

During the placement phase of the medical procedure, the prosthesis 720 is retained in a compressed condition by the sheath 730. The sheath 730 extends distally to a gripping and hemostatic sealing means 735 of the external manipulation section 780. During assembly of the introducer 700, the sheath 730 is advanced over the cylindrical sleeve 710 of the proximal attachment region 784 while the prosthesis 720 is held in a compressed state by an external force. A distal attachment (retention) section 740 is coupled to the thick walled plastic tube 741. The distal attachment section 740 retains a distal end 742 of the prosthesis 720 during the procedure. Likewise, the cylindrical sleeve 710 retains the self-expanding Z-stent 721.

The distal end 742 of the prosthesis 720 is retained by the distal attachment section 740. The distal end 742 of the prosthesis 720 has a loop (not shown) through which a distal trigger wire (not shown) extends. The distal trigger wire extends through an aperture (not shown) in the distal attachment section 740 into an annular region between the thin walled tube 715 and the thick walled tube 741. The distal trigger wire extends through the annular space to the manipulation region 780. The distal trigger wire exits the annular space at a distal wire release mechanism 725.

The external manipulation section 780 includes a hemostatic sealing means 735. The hemostatic sealing means 735 includes a hemostatic seal (not shown) and a side tube 729. The hemostatic sealing means 735 also includes a clamping collar (not shown) that clamps the sheath 730 to the hemostatic seal, and a silicone seal ring (not shown) that forms a hemostatic seal around the thick walled plastic tube 741. The side tube 729 facilitates the introduction of medical reagents between the thick walled tube 741 and the sheath 730.

A proximal portion of the external manipulation section 780 includes a release wire actuation section that has a body 736. The body 736 is mounted onto the thick walled plastic tube 741. The thin walled tube 715 passes through the body 736. The distal wire release mechanism 725 and the proximal wire release mechanism 724 are mounted for slidable movement onto the body 736.

The positioning of the proximal and distal wire release mechanisms 724 and 725 is such that the proximal wire release mechanism 724 must be moved before the distal wire release mechanism 725 can be moved. Therefore, the distal end 742 of the prosthesis 720 cannot be released until the self-expanding Z-stent 721 has been released, and the barbs 751 have been anchored to the lumen. Clamping screws 737 prevent inadvertent early release of the prosthesis 720. A hemostatic seal (not shown) is included so that the release wires can extend out through the body 736 without unnecessary blood loss during the medical procedure.

A distal portion of the external manipulation section 780 includes a pin vise 739. The pin vise 739 is mounted onto the distal end of the body 736. The pin vise 739 has a screw cap 746. When screwed in, vise jaws (not shown) of the pin vise 739 clamp against or engage the thin walled metal tube 715. When the vise jaws are engaged, the thin walled tube 715 can only move with the body 736, and hence the thin walled tube 715 can only move with the thick walled tube 741. With the screw cap 746 tightened, the entire assembly can be moved together as one piece.

Figure 44:
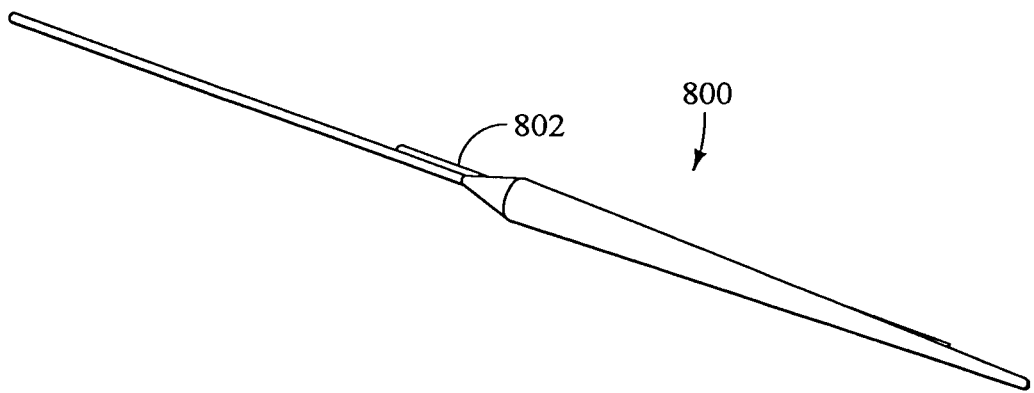
FIG. 44 shows a portion of a device used for deploying a branched vessel prosthesis.

A second introducer may be used to introduce the helical branched prosthesis 750 and create a tromboning connection. This second introducer may be based on the same principles as the introducer 700 described above, but could be less complex. For example, the second introducer may include a sheath for containing the branched prosthesis 750 in a compressed state, so that it can be introduced into a targeted anatomy and then released to either self-expand or be actively expanded with a balloon. The second introducer could be equipped with a delivery tip 800, as shown in FIG. 44, to allow for the deployment of a guide wire 802 into the aortic bifurcation. A third introducer may be used to deploy the branch extension.

Deployment

Prosthetic modules are preferably deployed seriatim. The intermodular connection between the branched prosthesis 750 and the bifurcated prosthesis 720 is formed in situ. First the bifurcated prosthesis 720 is deployed, and then the branched prosthesis 750 is deployed. For example, a bifurcated aortic prosthesis 720, as described in WO98/53761, can be deployed into the abdominal aorta. The bifurcated prosthesis 720 has a generally inverted Y-shaped configuration having a body portion 723, a shorter leg 760 and a longer leg 732. The body of the prosthesis is constructed from tubular woven polyester fabric. At the proximal end of the prosthesis 720 is a self-expanding stent 721 which extends beyond the end of the prosthesis and has distally extending barbs 751. The shorter leg 760 and the longer leg 732 have internal projections extending from their distal termini.

This bifurcated prosthesis 720 can be deployed in any method known in the art, preferably the method described in WO98/53761 in which the device is inserted by an introducer via a surgical cut-down into a femoral artery, and then advanced into the desired position over a stiff wire guide using endoluminal interventional techniques. For example, a guide wire (not shown) is first introduced into a femoral artery of the patient and advanced until its tip is beyond the desired deployment region of the prosthesis 720. At this stage, the introducer assembly 700 is fully assembled, and ready for introduction into the patient. The prosthesis 720 is retained at one end by the cylindrical sleeve 710 and the other by the distal attachment sections 740, and compressed by the sheath 730. If an aortic aneurism is to be repaired, the introducer assembly 700 can be inserted through a femoral artery over the guide wire, and positioned by radiographic techniques, which are not discussed here.

Once the introducer assembly 700 is in the desired deployment position, the sheath 730 is withdrawn to just proximal of the distal attachment section 740. This action releases the middle portion of the prosthesis 720 so that it can expand radially. The proximal self-expanding stent 721, however, is still retained within the cylindrical sleeve 710. Also, the distal end 742 of the prosthesis 720 is still retained within the external sheath 730.

Next, the pin vise 739 is released to allow small movements of the thin walled tube 715 with respect to the thick walled tube 741. These movements allow the prosthesis 720 to be lengthened or shortened or rotated or compressed for accurate placement in the desired location within the lumen. Radiopaque markers (not shown) may be placed along the prosthesis 720 to assist with placement of the prosthesis.

When the proximal end of the prosthesis 720 is in place, the proximal trigger wire is withdrawn by distal movement of the proximal wire release mechanism 724. The proximal wire release mechanism 724 and the proximal trigger wire can be completely removed by passing the proximal wire release mechanism 724 over the pin vise 739, the screw cap 746, and the connection means 716.

Next, the screw cap 746 of the pin vise 739 is then loosened. After this loosening, the thin walled tube 715 can be pushed in a proximal direction to move the cylindrical sleeve 710 in a proximal direction. When the cylindrical sleeve 710 no longer surrounds the self-expanding stent 721, the self-expanding stent 721 expands. When the self-expanding stent 721 expands, the barbs 751 grip the walls of the lumen to hold the proximal end of the prosthesis 720 in place. From this stage on, the proximal end of the prosthesis 720 cannot be moved again.

Once the proximal end of the prosthesis 720 is anchored, the external sheath 730 is withdrawn to distal of the distal attachment section 740. This withdrawal allows the contralateral limb 760 and the longer leg 732 of the prosthesis 720 to expand. At this point, the distal end 742 of the prosthesis 720 may still be moved. Consequently, the prosthesis 720 can still be rotated or lengthened or shortened for accurate positioning. Such positioning of the prosthesis 720 may ensure that the shorter leg 760 extends in the direction of a contralateral artery.

After the shorter leg 760 extends in the direction of the contra-iliac artery, the branched prosthesis 750 is deployed. The branched prosthesis 750 is deployed such that it forms a tromboning connection with the shorter leg 760 and extends from the shorter leg 760 into the contralateral artery. The coupling of the prosthesis 720 and branched prosthesis 750 is described in greater detail in other portions of this disclosure.

The method of introduction of the branched prosthetic module 750 may be as follows. A guide wire (not shown) is introduced into the contralateral femoral artery and advanced until its tip is above the region into which the prosthesis is to be deployed. The second introducer is then advanced over the guide wire with an oscillating and rotating action until the extension prosthesis is overlapped one full stent within the contralateral limb 760. A final position check may then be made before the sheath is withdrawn while holding the thick walled tube in place. A similar methodology for deployment of a hypogastric branch graft module is described and illustrated in a U.S. Patent Application Publication No. 2005/0182476, which is incorporated herein by reference.

The guide wire 602 can be deployed from the tip 600 of the second introducer captured and pulled over to the ipsilateral side to facilitate deployment of a third introducer through the ipsilateral side into the contralateral side to deploy a branch extension into the hypogastric artery. Preferably, a preloaded wire or snare within the limb of the prosthetic branch will preclude the need for complex localization, catheterization of branches and separate insertion of the wire through the sheath. This approach may be particularly important when multiple branches are present. The distal handle of the delivery system may be equipped with an additional trigger wire to accommodate this feature. The second and third introducers and the methods of using them are described in greater detail in U.S. Patent Application, "Introducer for an Iliac Side Branch Device," Ser. No. 60/510,823, filed Oct. 14, 2003, which is incorporated herein by reference.

The introducer and deployment method described above can be adapted for implantation in other regions. For example, if a first prosthetic module is placed into the aorta, a connecting prosthetic module can be placed into the renal, iliac, superior mesenteric, celiac or other artery to form a tromboning interconnection. If a first prosthetic module is placed into the thoracic aorta, a connecting prosthetic module can be placed into another portion of the thoracic aorta, the left subclavian, left common carotid, innominate or other artery. Furthermore, prosthetic modules which are implanted in the same artery can be connected to each other. The overlap region of each of these embodiments is preferably adapted to the size of the relevant anatomy and the forces to which the prostheses are exposed in the relevant anatomy.

EXAMPLE 1

The flow force on the branched limb is dependent upon the loads applied to the branch point and ultimate angulation of the prosthetic branch. Of particular interest are the forces that may cause separation of the branch extension from the prosthetic branch. Forces due to flow in the y-direction, if significant enough, can become larger than the frictional forces that hold the branch extension and the prosthetic branch together, resulting in separation. If the separation is substantial, a type III endoleak will occur and the aneurysm will no longer be excluded.

The prostheses described above may be subjected to an in vitro leak pressure test. The purpose of this test procedure is to determine the minimum internal pressure required causing leakage at the mating point between two prostheses.

The test requires a pressure transducer, a pressure monitor, water/glycerin mixture (dyed)@3.64 cP, water bath, submersible heater, water pump, temperature controller, mating surface thermocouple, and mercury thermometer.

The prosthetic branch and branch extension are mated such that there is a suitable tromboning connection, preferably with a 1.5-2 cm overlap and a 1 mm or less difference in diameter at the interconnection. The devices may be ballooned for 30 seconds using a suitably sized balloon dilation catheter.

Internal pressure in the mated devices is measured utilizing a pressure transducer and pressure monitor. These instruments are connected to a syringe providing manually controlled pressure into the mated devices. The pressure liquid is a glycerin/water mixture to 3.64 centipoise (cP) dyed with blue food coloring. The device was placed in a 37° C. water bath and the presence of a leak would be defined and identified by leakage of the blue-dyed glycerin/water mixture. Visual accounts of leakage and a recording of peak pressures were manually recorded.

EXAMPLE 2

The prostheses described above may be subjected to an in vivo test, preferably in non-human mammals. One animal that is suitable for implantation of the prosthesis for testing and therapeutic purposes is the domestic cow. For testing purposes, six- to ten-week-old male calves were used.

As presurgical preparation, each animal was given a daily dose of 325 mg of aspirin beginning on the day prior to the procedure for the purpose of platelet inhibition. Each animal was kept without food for approximately 8-12 hours and without water for approximately 2 hours preceding each procedure. A pre-operative baseline ACT was measured in a Hemochron Jr. Signature Series Machine® (available from ITC in Edison, N.J.).

Each calf was sedated with Xylazine (1.0 mg/10 lbs, IM). Once the animal was lightly sedated, an induction mask was used to deliver Isofluorane (2-4%). The calf's face was placed into the mask while the inhalation anaesthetic was delivered.

The animal may be intubated in standard fashion. Once the endotracheal tube was placed, it was secured. The ventilator was turned on and connected to the animal to increase the depth of anesthesia and mechanically ventilate the animals. Isofluorane dosages ranged from approximately 0.8-1.25%, although may be any percentage based on relevant factors. During this pre-surgical preparation, each animal may also receive an injection of benzathine procaine penicillin (30,000-50,000 U/kg IM).

The animal was placed on its left side with its right hind leg extended up and secured with gauze ties. A ground pad and EKG leads were placed on the animal. An intravenous catheter (IV) was placed in the peripheral leg vein and secured with tape. Lactate Ringers (LR) was infused through the catheter for the duration of the procedure to provide adequate hydration. Both groins were shaved and sterilely prepped with 70% alcohol and betadine.

The implantation of this branched vessel device involved basic endovascular techniques. A femoral cutdown was performed on the left leg to gain access to a femoral vessel. A retroperitoneal incision was performed to provide access to the right iliac artery. A third access point was gained via a cutdown exposing the right carotid artery. Hemostatic vessel loops were placed proximally and distally on the arteries. A single wall puncture needle was used to access the left femoral artery, and conformation of the cannulation was confirmed by the presence of pulsatile arterial flow from the needle hub.

Once the pulsatile flow was observed, a wire was placed in the descending abdominal aorta. The animal was heparinized with 200 IU of porcine heparin/kg. An activated clotting time was obtained within 3-10 minutes following heparin administration to ensure adequate anti-coagulation, to achieve a preferred minimum of 1.5-2 times the baseline ACT. An 8 French introducer sheath was advanced into the left arterial lumen. Before and after placement, the side port of each sheath was flushed with 0.9% normal saline.

A 5 French pigtail catheter was inserted over the wire through the introducer sheath and advanced into to the region of the aortic arch using fluoroscopic guidance. A baseline digital subtraction angiogram of the descending thoracic aorta was obtained utilizing an appropriate dose of contrast. Once the baseline angiogram had been achieved, a wire was placed through the pigtail catheter and advanced into the thoracic aorta. The catheter was then removed. A 12.5 MHz Boston Scientific IVUS (intravenous ultrasound) probe was inserted over the wire in a monorail fashion, and baseline IVUS measurements were obtained. These measurements included cross-sectional diameters of the distal abdominal aorta approximately 9 cm proximal to the trifurcation.

An external helical device similar to that shown in and described in reference to FIG. 11 was employed. This particular prosthesis was manufactured from a Viabahn® Endoprosthesis (W. L. Gore & Associates, Inc., Newark, Del.), which is made from expanded PTFE. It was loaded into an 18 French cartridge with a 4 French catheter providing 0.035 inch wire access through the man device and a preloaded 0.018 inch wire within the branched limb.

A single wall puncture needle was used to access the right iliac artery. Once an Amplatz guide wire was placed, a 20 French Check-Flo® (Cook Incorporated, Bloomington, Ind.) introducer sheath was advanced to 9 cm above the aortic bifurcation and utilized as the delivery system. The preloaded 0.018 inch wire was advanced through the valve of the Check-Flo® sheath using a peal-away sheath. The loaded device cartridge was then inserted into the 20 French Check-Flo® using the dilators as pushers. The 0.018 inch wire was snared from the carotid artery to provide through-and-through access for the branch vessel wire. The prosthesis was then deployed to the point that the ostium of the prosthetic branch was exposed. The prosthesis was then advanced through the contralateral femoral artery.

The prosthesis was deployed with a 2.0 cm overlap within the prosthetic branch. The entire length of the prosthesis was ballooned with a 7 mm×4 cm balloon. Post implant angiographic and IVUS assessments were performed. The final IVUS assessment measured the proximal, mid and distal points of the stent graft along with the ostium, while the angiogram assessed the presence of any endoleaks, as well as the location of the stent graft. If desirable, the prosthesis may be explanted and subjected to post-explant analysis.

EXAMPLE 3

One helical branch vessel stent graft is deployed such that the branch is properly oriented with respect to the internal iliac artery. Four markers on the distal end of the branch are placed approximately 5 mm above the internal iliac artery. The sheath housing the device is withdrawn to expose the branch limb, leaving the distal end constrained within the sheath in the external iliac artery. The wire dwelling within the contralateral limb is replaced with a steerable guidewire, which is then advanced into the distal aorta and snared with a snare device introduced from the contralateral femoral artery. This provides access from the contralateral groin, through the proximal aspect of the iliac branch, into the iliac limb, and then alongside the outer portion of the distal segment (external iliac artery segment) to the ipsilateral groin.

Over this through-and-through wire, a 10 F or 12 F Balkin sheath (Cook Incorporated, Bloomington, Ind.) is introduced and advanced into the side branch limb. Alongside the through-and-through guidewire, a steerable catheter and wire combination is advanced and utilized to selectively cannulate the internal iliac artery.

Once a reasonable purchase is established, a stiffer wire is placed and the mating component is advanced into the desired position. The mating component may be a Viabahn® graft which is advanced into the hypogastric artery so that it has preferably a 2 cm minimum overlap with the helical branch. Once the mating graft is deployed and appropriately ballooned, the remainder of the external iliac limb is deployed. The component is then mated to the remainder of the Zenith® graft with the modified 12 mm extension described in FIG. 3c.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

The invention claimed is:

1. An endoluminal prosthesis comprising:
   a prosthetic trunk having a first end and a second end and comprising a trunk lumen extending therethrough, a wall, and an anastomosis in the wall between the first and second ends;
   a stent attached to the prosthetic trunk adjacent the anastomosis, where the stent comprises a generally tubular stent body that provides radial support to the prosthetic trunk, where the stent body alternates endlessly about a longitudinal axis of the prosthetic trunk between a first stent pattern and a second stent pattern;

where the first stent pattern comprises a loop having a contour that contacts and supports the entire perimeter of the anastomosis.

2. The prosthesis of claim 1, where the second stent pattern has a generally zigzag shape.

3. The prosthesis of claim 1, where the loop comprises an ovoid shape.

4. An endoluminal prosthesis comprising:
a prosthetic trunk comprising a trunk lumen extending therethrough;
a prosthetic branch comprising a branch lumen extending therethrough;
a stent having a stent pattern that alternates endlessly about the perimeter of the stent between a first tubular stent region disposed about a first axis and a second tubular stent region disposed about a second axis;
where the first stent region is attached to and supports at least a portion of the prosthetic trunk and the second stent region is attached to and supports at least a portion of the prosthetic branch, and
where the stent has a figure-8 shape.

5. The prosthesis of claim 4, where the stent pattern includes a generally zigzag shape.

6. The prosthesis of claim 4, where the first stent region has a different diameter than the second stent region.

7. The prosthesis of claim 4, where the first stent axis is generally collinear with the second stent axis.

8. The prosthesis of claim 4, where the prosthetic branch is disposed, at least in part, inside the prosthetic trunk lumen.

9. The prosthesis of claim 4, where the prosthetic branch is disposed, at least in part, outside the prosthetic trunk lumen.

10. The prosthesis of claim 4 where at least a portion of the first stent region is disposed on an interior surface of the prosthetic trunk.

11. The prosthesis of claim 10, where at least a portion of the first stent region is disposed on an exterior surface of the prosthetic branch.

12. The prosthesis of claim 4, where at least a portion of the second stent region is disposed on an exterior surface of the prosthetic branch.

13. The prosthesis of claim 4, further comprising any two or more of the following:
the stent pattern includes a generally zigzag shape;
the first stent region has a different diameter than the second stent region;
the first stent axis is generally collinear with the second stent axis;
the prosthetic branch is disposed, at least in part, inside the prosthetic trunk lumen;
the prosthetic branch is disposed, at least in part, outside the prosthetic trunk lumen;
the stent has a figure-8 shape;
at least a portion of the first stent region is disposed on an interior surface of the prosthetic trunk;
at least a portion of the first stent region is disposed on an exterior surface of the prosthetic branch; and
at least a portion of the second stent region is disposed on an exterior surface of the prosthetic branch.

* * * * *